United States Patent
Oishi et al.

(10) Patent No.: US 7,638,540 B2
(45) Date of Patent: Dec. 29, 2009

(54) BENZOFURAN COMPOUND AND MEDICINAL COMPOSITION CONTAINING THE SAME

(75) Inventors: Yoshitaka Oishi, Uji (JP); Shigekatsu Kohno, Gifu (JP); Takehiko Yokomizo, Koshigaya (JP)

(73) Assignee: The New Industry Research Organization, Hyogo (JP)

( * ) Notice: Subject to any disclaimer, the term of this patent is extended or adjusted under 35 U.S.C. 154(b) by 395 days.

(21) Appl. No.: 10/558,557

(22) PCT Filed: May 28, 2004

(86) PCT No.: PCT/JP2004/007802

§ 371 (c)(1),
(2), (4) Date: Mar. 1, 2006

(87) PCT Pub. No.: WO2004/106317

PCT Pub. Date: Dec. 9, 2004

(65) Prior Publication Data

US 2006/0194851 A1      Aug. 31, 2006

(30) Foreign Application Priority Data

May 29, 2003     (JP) .............................. 2003-153563

(51) Int. Cl.
   *A61K 31/426* (2006.01)
   *C07D 277/20* (2006.01)
(52) U.S. Cl. ...................... 514/365; 548/203
(58) Field of Classification Search ................. 548/203
   See application file for complete search history.

(56) References Cited

U.S. PATENT DOCUMENTS

| | | | |
|---|---|---|---|
| 4,259,338 A | 3/1981 | Paioni et al. | |
| 4,863,958 A | 9/1989 | Belanger et al. | |
| 5,089,514 A | 2/1992 | Hulin | |
| 5,296,495 A * | 3/1994 | Matsuo et al. | 514/365 |
| 5,504,213 A | 4/1996 | Fischer et al. | |
| 5,981,572 A | 11/1999 | Ellis et al. | |

OTHER PUBLICATIONS

Inflammation [online], [retrieved on Oct. 25, 2007]. Retrieved from the Internet, URL; http://en.wikipedia.org/wiki/Inflammation>.*
Allergies [online], [retrieved on Oct. 25, 2007]. Retrieved from the Internet, URL; http://www.nlm.nih.gov/medlineplus/ency/article/000812.htm>.*
Fujiwara et al., "Palladium-Catalyzed Alkenylation of Aromatic Heterocycles with Olefins. Synthesis of Functionalized Aromatic Heterocycles", *Journal of Organic Chemistry*, vol. 46, No. 5, pp. 851-855, 1981.

* cited by examiner

*Primary Examiner*—Rebecca L Anderson
*Assistant Examiner*—Shawquia Young
(74) *Attorney, Agent, or Firm*—Wenderoth, Lind & Ponack, L.L.P.

(57) ABSTRACT

The present invention relates to a benzofuran compound of the formula (I)

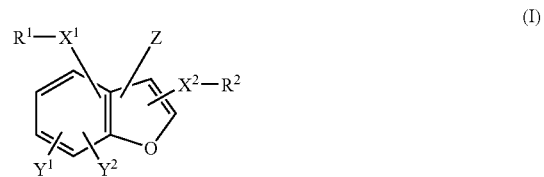

(I)

wherein each symbol is as defined in the description, a pharmaceutically acceptable salt thereof and the like. The compound of the present invention has superior leukotriene inhibitory action, BLT2 competitive inhibitory action, BLT2 blocking action, action for the prophylaxis or treatment of allergy, action for the prophylaxis or treatment of asthma and action for the prophylaxis or treatment of inflammation, and is useful as an agent for the prophylaxis or treatment of diseases such as allergic disease, asthma, inflammation and the like, and other diseases.

8 Claims, No Drawings

BENZOFURAN COMPOUND AND MEDICINAL COMPOSITION CONTAINING THE SAME

This application is a U.S. national stage of International Application No. PCT/JP2004/007802 filed May 28, 2004.

TECHNICAL FIELD

The present invention relates to a benzofuran compound having a leukotriene (particularly leukotriene B4) inhibitory action and a pharmaceutically acceptable salt thereof. Moreover, the present invention relates to a pharmaceutical composition comprising the above-mentioned benzofuran compound or a pharmaceutically acceptable salt thereof. Furthermore, the present invention relates to a leukotriene inhibitor, a BLT2 competitive inhibitor, an agent for the prophylaxis or treatment of allergy, an agent for the prophylaxis or treatment of asthma or an agent for the prophylaxis or treatment of inflammation, which comprises the above-mentioned benzofuran compound or a pharmaceutically acceptable salt thereof, and the like.

BACKGROUND ART

Leukotriene B4 (LTB4) is one kind of arachidonic acid metabolites and one of the most potent activation substances of neutrophil and macrophage (see e.g., Samuelsson et al., "science", (US), (1987), vol. 237, p. 1171-1176 and Shimizu et al., "Journal of Neurochemistory", (UK), (1990), vol. 55, p. 1-15). It is known that action of LTB4 on neutrophil or macrophage results in the induction of various responses important for biological defense, such as adhesion to vascular endothelial cells, degranulation of lysosome enzymes, production of active oxygen, chemotaxis into inflammatory tissues and the like. However, overproduction of LTB4 is deeply involved in the formation and aggravation of various diseases accompanied by inflammations or allergic responses, psoriasis (see e.g., Iversen et al., "Skin Pharmacology", (US), (1997), vol. 10, p. 169-177), bronchial asthma (see e.g., Turner et al., "The Journal of Clinical Investigation", (US), (1996), vol. 97, p. 381-387), rheumatoid arthritis (see e.g., Griffiths et al., "Proceedings of the National Academy of Science of the USA", (US), (1995), vol. 92, p. 517-521), inflammatory bowel disease (see e.g., Sharon et al., "Gastroenterology", (US), (1984), vol. 86, p. 453-460), ischemic renal failure (see e.g., Noiri et al., "Proceedings of the National Academy of Science of the USA", (US), (2000), vol. 97, 823-828) and the like. Therefore, the development of a therapeutic agent capable of selectively inhibiting the production or action of LTB4 in various ways has been desired for the prophylaxis or treatment of these diseases. In recent years, it has been clarified that LTB4 receptors include two kinds of receptors (BLT1, BLT2) having different expression distributions and affinities (see e.g., Yokomizo et al., "Nature", (UK), (1997), vol. 387, p. 620-624 and Yokomizo et al., "The Journal of the Experimental Medicine", (2000), vol. 192, p. 421-431). Therefore, broadening of the range of selection of LTB4 inhibitor has been desired more than ever.

On the other hand, while benzofuran derivatives having a leukotriene inhibitory action have been disclosed (e.g., JP-A-61-17579, JP-A-5-202040, JP-A-5-317024 etc.), the selectivity to LTB4 has not been disclosed.

An object of the present invention is to increase diversity of and broaden the selection range of leukotriene inhibitors, BLT2 competitive inhibitors, agents for the prophylaxis or treatment of allergy, agents for the prophylaxis or treatment of asthma and agents for the prophylaxis or treatment of inflammation, by providing novel compounds having a potent leukotriene (particularly leukotriene B4) inhibitory action and a BLT2 competitive inhibitory action as well as high safety.

DISCLOSURE OF THE INVENTION

The present inventors have conducted intensive studies in an attempt to solve the above-mentioned problems and found that a benzofuran compound having a novel structure or a pharmaceutically acceptable salt thereof possesses a potent leukotriene (particularly leukotriene B4) inhibitory action, particularly superior in a BLT2 competitive inhibitory action and a BLT2 blocking action, as well as high safety, which resulted in the completion of the present invention.

Accordingly, the present invention relates to the following.

(1) A compound represented by the formula (I)

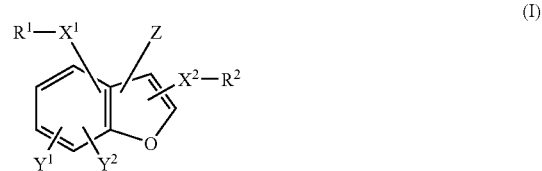

wherein
Z is a group selected from the following formulas $Z^a$, $Z^b$ and $Z^d$

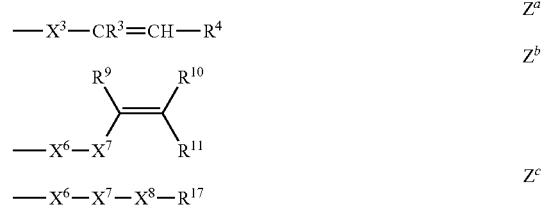

wherein
$X^3$ is a bond or

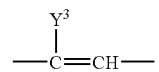

wherein $Y^3$ is a hydrogen atom or a halogen atom;
$R^3$ is a hydrogen atom or a $C_{1-6}$ alkyl group;
$R^4$ is a cyano group, —COOAlk (Alk is hereinafter independently a hydrogen atom or a $C_{1-6}$ alkyl group), —CHO, a $C_{6-14}$ aryl group (the aryl group is optionally substituted by one or more halogen atoms),

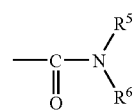

wherein $R^5$ and $R^6$ are the same or different and each is a hydrogen atom, a $C_{1-6}$ alkyl group (the alkyl group is optionally substituted by one or more —COOAlk), a $C_{6-14}$ aryl group (the aryl group is optionally substituted by one or more substituents selected from the group consisting of hydroxyl group, $C_{1-6}$ alkoxy group and —COOAlk), or $R^5$ and $R^6$ optionally form, together with the nitrogen atom bonded thereto, a 5- to 7-membered heterocycle (the heterocycle optionally further has a hetero atom selected from N and O, and is optionally substituted by one or more substituents selected from the group consisting of $C_{1-6}$ alkyl group, $C_{6-14}$ aryl group and $C_{6-14}$ aryl-$C_{1-6}$ alkyl group, or

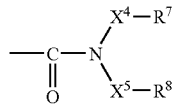

wherein $X^4$ and $X^5$ are the same or different and each is a bond or a $C_{1-6}$ alkylene group (the alkylene group is optionally substituted by one or more —COOAlk); and $R^7$ and $R^8$ are the same or different and each is a hydrogen atom, a $C_{6-14}$ aryl group (the $C_{6-14}$ aryl group is optionally substituted by one or more substituents selected from the group consisting of hydroxyl group and $C_{1-6}$ alkoxy group) or a $C_{1-6}$ alkylthio group (the alkylthio group is optionally substituted by one or more $C_{6-14}$ aryl groups);

$X^6$ is a bond, a $C_{1-6}$ alkylene group or

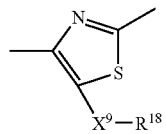

wherein $R^{18}$ is a hydrogen atom, a hydroxyl group, —CHO, —COOAlk or a $C_{1-6}$ alkyl group (the alkyl group is optionally substituted by one or more hydroxyl groups), and $X^9$ is a bond, —CH=N— or —CO—NH—;

$X^7$ is a bond, —HN—CO— or —N=CH—;

$R^9$ is a hydrogen atom or a cyano group;

$R^{10}$ is a hydrogen atom, a hydroxyl group, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group, or $R^9$ and $R^{10}$ optionally form, together with the carbon atoms bonded thereto, a heteroaromatic ring, whereby $Z^b$ becomes

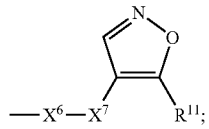

$R^{11}$ is a hydrogen atom, a hydroxyl group, a $C_{1-6}$ alkyl group, a $C_{6-14}$ aryl group (the aryl group is optionally substituted by one or more substituents selected from the group consisting of hydroxyl group and $C_{1-6}$ alkoxy group) or a $C_{6-14}$ aryl-$C_{1-6}$ alkyl group;

$X^8$ is a bond or a $C_{1-6}$ alkylene group; and $R^{17}$ is a hydrogen atom, a halogen atom, —COOAlk, a cyano group, a $C_{1-6}$ alkyl group (the alkyl group is optionally substituted by one or more substituents selected from the group consisting of halogen atom and cyano group), a $C_{6-14}$ aryl group (the aryl group is optionally substituted by one or more substituents selected from the group consisting of hydroxyl group and $C_{1-6}$ alkoxy group) or an amino group (the amino group is optionally mono- or di-substituted by $C_{1-6}$ alkyl group(s) (the alkyl group is optionally substituted by one or more $C_{6-14}$ aryl groups));

$X^1$ is a bond, —O—,

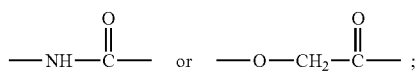

$R^1$ is a hydrogen atom, a halogen atom, a cyano group, an amino group, a $C_{1-6}$ alkoxy group, a $C_{6-14}$ aryl group (the aryl group is optionally substituted by one or more substituents selected from the group consisting of hydroxyl group, halogen atom and $C_{1-6}$ alkoxy group) or a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group(s)), sulfanyl group, $C_{6-14}$ arylsulfanyl group (the aryl of the arylsulfanyl group is optionally substituted by one or more halogen atoms) and $C_{6-14}$ aryl group (the aryl group is optionally substituted by one or more substituents selected from the group consisting of hydroxyl group and $C_{1-6}$ alkoxy group)], or $R^1$ is optionally $Z^a$;

$X^2$ is a bond, a $C_{1-6}$ alkylene group,

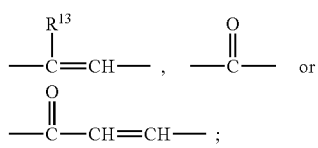

$R^{13}$ is a hydrogen atom, a halogen atom or a $C_{1-6}$ alkyl group;

$R^2$ is a hydrogen atom, a halogen atom, a cyano group, an amino group (the amino group is optionally mono- or di-substituted by substituent(s) selected from the group consisting of $C_{1-6}$ alkyl group and $C_{6-14}$ aryl group (the aryl group is optionally substituted by one or more substituents selected from the group consisting of hydroxyl group and $C_{1-6}$ alkoxy group)), a hydroxyl group,

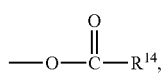

—COOAlk, —CHO, a $C_{1-6}$ alkoxy group, a $C_{1-6}$ alkyl group (the alkyl group is optionally substituted by one or more halogen atoms) or a $C_{6-14}$ aryl group (the aryl group is optionally substituted by one or more substituents selected from the group consisting of halogen atom, cyano group, hydroxyl group, $C_{1-6}$ alkoxy group and $Z^a$ (when Z is $Z^b$));

$R^{14}$ is a hydrogen atom or a $C_{1-6}$ alkyl group; and $Y^1$ and $Y^2$ are the same or different and each is a hydrogen atom, a halogen atom, a hydroxyl group, a $C_{1-6}$ alkoxy group, a $C_{6-14}$ aryl group (the aryl group is optionally substituted by one or more halogen atoms) or

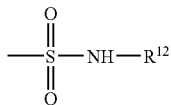

wherein $R^{12}$ is a hydrogen atom, a $C_{1-6}$ alkyl group, a $C_{6-14}$ aryl group (the aryl group is optionally substituted by one or more substituents selected from the group consisting of hydroxyl group and $C_{1-6}$ alkoxy group) or a $C_{6-14}$ aryl-$C_{1-6}$ alkyl group (the aryl group of the arylalkyl group is optionally substituted by one or more substituents selected from the group consisting of hydroxyl group and $C_{1-6}$ alkoxy group)

or a pharmaceutically acceptable salt thereof.

(2) The compound of the above-mentioned (1), wherein, in the formula (I)

Z is $$—X^3—CR^3=CH—R^4 \qquad Z^a$$

wherein $X^3$ is a bond or

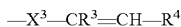

wherein $Y^3$ is a hydrogen atom or a halogen atom;
$R^3$ is a hydrogen atom or a $C_{1-6}$ alkyl group; and
$R^4$ is a cyano group, —COOAlk (the Alk is hereinafter independently a hydrogen atom or a $C_{1-6}$ alkyl group),

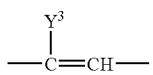

wherein $R^5$ and $R^6$ are the same or different and each is a hydrogen atom, a $C_{1-6}$ alkyl group (the alkyl group is optionally substituted by one or more —COOAlk), a $C_{6-14}$ aryl group (the aryl group is optionally substituted by one or more substituents selected from the group consisting of hydroxyl group, $C_{1-6}$ alkoxy group and —COOAlk), or $R^5$ and $R^6$ optionally form, together with the nitrogen atom bonded thereto, a 5- to 7-membered heterocycle (the heterocycle optionally further has a hetero atom selected from N and O, and is optionally substituted by one or more substituents selected from the group consisting of $C_{1-6}$ alkyl group, $C_{6-14}$ aryl group and $C_{6-14}$ aryl-$C_{1-6}$ alkyl group), or

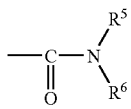

wherein $X^4$ and $X^5$ are the same or different and each is a bond or a $C_{1-6}$ alkylene group (the alkylene group is optionally substituted by one or more —COOAlk); and $R^7$ and $R^8$ are the same or different and each is a hydrogen-atom, a $C_{6-14}$ aryl group (the $C_{6-14}$ aryl group is optionally substituted by one or more substituents selected from the group consisting of hydroxyl group and $C_{1-6}$ alkoxy group) or a $C_{1-6}$ alkylthio group (the alkylthio group is optionally substituted by one or more $C_{6-14}$ aryl groups), or Z is

wherein
$X^6$ is a bond or a $C_{1-6}$ alkylene group;
$X^7$ is —HN—CO—;
$R^9$ is a hydrogen atom or a cyano group;
$R^{10}$ is a hydrogen atom, a hydroxyl group, a $C_{1-6}$ alkyl group or a $C_{6-14}$ aryl group, or $R^9$ and $R^{10}$ optionally form, together with the carbon atoms bonded thereto, a heteroaromatic ring, whereby $Z^b$ becomes

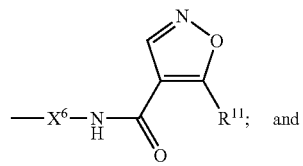

$R^{11}$ is a hydrogen atom, a hydroxyl group or a $C_{1-6}$ alkyl group,
$X^1$ is a bond, —O—,

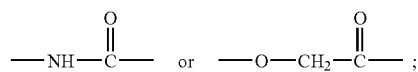

$R^1$ is a hydrogen atom, a halogen atom, a cyano group, an amino group, a $C_{1-6}$ alkoxy group, a $C_{6-14}$ aryl group (the aryl group is optionally substituted by one or more substituents selected from the group consisting of hydroxyl group and $C_{1-6}$ alkoxy group) or a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group(s)) and $C_{6-14}$ aryl group (the aryl group is optionally substituted by one or more substituents selected from the group consisting of hydroxyl group and $C_{1-6}$ alkoxy group)], or $R^1$ is optionally $Z^a$ when Z is $Z^b$;
$X^2$ is a bond, a $C_{1-6}$ alkylene group,

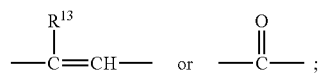

$R^{13}$ is a hydrogen atom or a $C_{1-6}$ alkyl group;
$R^2$ is a hydrogen atom, a halogen atom, a cyano group, an amino group, a hydroxyl group,

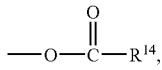

—COOAlk, a $C_{1-6}$ alkoxy group, a $C_{1-6}$ alkyl group, a $C_{6-14}$ aryl group (the aryl group is optionally substituted by one or more substituents selected from the group consisting of halogen atom, cyano group and $Z^a$ (when Z is $Z^b$));
$R^{14}$ is a hydrogen atom or a $C_{1-6}$ alkyl group;
$Y^1$ and $Y^2$ are the same or different and each is a hydrogen atom, a halogen atom or

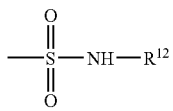

wherein $R^{12}$ is a hydrogen atom, a $C_{1-6}$ alkyl group, a $C_{6-14}$ aryl group (the aryl group is optionally substituted by one or more substituents selected from the group consisting of hydroxyl group and $C_{1-6}$ alkoxy group) or a $C_{6-14}$ aryl-$C_{1-6}$ alkyl group (the aryl group of the arylalkyl group is optionally substituted by one or more substituents selected from the group consisting of hydroxyl group and $C_{1-6}$ alkoxy group), or a pharmaceutically acceptable salt thereof.

(3) The compound of the above-mentioned (1), wherein, in the formula (I),
Z is $Z^a$,
$X^3$ is a bond or

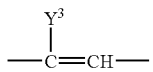

wherein $Y^3$ is a hydrogen atom or halogen atom;
$R^3$ is a hydrogen atom or a $C_{1-6}$ alkyl group; and
$R^4$ is a cyano group, —COOAlk (the Alk is hereinafter independently a hydrogen atom or a $C_{1-6}$ alkyl group), —CHO, a $C_{6-14}$ aryl group (the aryl group is optionally substituted by one or more halogen atoms),

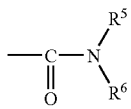

wherein $R^5$ and $R^6$ are the same or different and each is a hydrogen atom, a $C_{1-6}$ alkyl group (the alkyl group is optionally substituted by one or more —COOAlk), a $C_{6-14}$ aryl group (the aryl group is optionally substituted by one or more substituents selected from the group consisting of hydroxyl group, $C_{1-6}$ alkoxy group and —COOAlk), or $R^5$ and $R^6$ optionally form, together with the nitrogen atom bonded thereto, a 5- to 7-membered heterocycle (the heterocycle optionally further has a hetero atom selected from N and O, and is optionally substituted by one or more substituents selected from the group consisting of $C_{1-6}$ alkyl group, $C_{6-14}$ aryl group and $C_{6-14}$ aryl-$C_{1-6}$ alkyl group), or

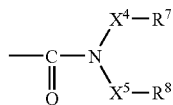

wherein $X^4$ and $X^5$ are the same or different and each is a bond or a $C_{1-6}$ alkylene group (the alkylene group is optionally substituted by one or more —COOAlk), and $R^7$ and $R^8$ are the same or different and each is a hydrogen atom, a $C_{6-14}$ aryl group (the $C_{6-14}$ aryl group is optionally substituted by one or more substituents selected from the group consisting of hydroxyl group and $C_{1-6}$ alkoxy group) or a $C_{1-6}$ alkylthio group (the alkylthio group is optionally substituted by one or more $C_{6-14}$ aryl groups)];
$X^1$ is a bond, —O—,

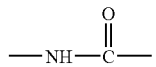

or

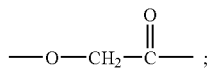

$R^1$ is a hydrogen atom, a halogen atom, a cyano group, an amino group, a $C_{1-6}$ alkoxy group, a $C_{6-14}$ aryl group (the aryl group is optionally substituted by one or more substituents selected from the group consisting of hydroxyl group, halogen atom and $C_{1-6}$ alkoxy group) or a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group(s)), sulfanyl group, $C_{6-14}$ arylsulfanyl group (the aryl of the arylsulfanyl group is optionally substituted by one or more halogen atoms) and $C_{6-14}$ aryl group (the aryl group is optionally substituted by one or more substituents selected from the group consisting of hydroxyl group and $C_{1-6}$ alkoxy group)], or $R^1$ is optionally $Z^a$;
$X^2$ is a bond,

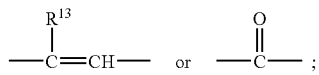

$R^{13}$ is a hydrogen atom, a halogen atom or a $C_{1-6}$ alkyl group;
$R^2$ is a hydrogen atom, a halogen atom, an amino group (the amino group is optionally mono- or di-substituted by substituent(s) selected from the group consisting of $C_{1-6}$ alkyl group and $C_{6-14}$ aryl group (the aryl group is optionally substituted by one or more substituents selected from the group consisting of hydroxyl group and $C_{1-6}$ alkoxy group)), —COOAlk, —CHO, a $C_{1-6}$ alkoxy group, a $C_{1-6}$ alkyl group (the alkyl group is optionally substituted by one or more halogen atoms) or a $C_{6-14}$ aryl group (the aryl group is optionally substituted by one or more substituents selected from the group consisting of halogen atom and cyano group); and $Y^1$ and $Y^2$ are the same or different and each is a hydrogen atom, a halogen atom, a hydroxyl group, a $C_{1-6}$ alkoxy group, a $C_{6-14}$ aryl group (the aryl group is optionally substituted by one or more halogen atoms) or

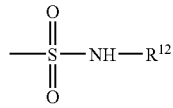

wherein $R^{12}$ is a hydrogen atom, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group (the aryl group of the aryl-alkyl group is optionally substituted by one or more substituents selected from the group consisting of hydroxyl group and $C_{1-6}$ alkoxy group), or a pharmaceutically acceptable salt thereof.

(4) The compound of the above-mentioned (1), wherein, in the formula (I)

$Z$ is $Z^b$ or $Z^d$, $X^6$ is a bond, a $C_{1-6}$ alkylene group or

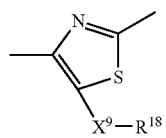

wherein $R^{18}$ is a hydrogen atom, a hydroxyl group, —CHO, —COOAlk or a $C_{1-6}$ alkyl group (the alkyl group is optionally substituted by one or more hydroxyl groups), and $X^9$ is a bond, —CH=N— or —CO—NH—;

$X^7$ is a bond, —HN—CO— or —N=CH—;

$R^9$ is a hydrogen atom or a cyano group;

$R^{10}$ is a hydrogen atom, a hydroxyl group, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group, or $R^9$ and $R^{10}$ optionally form, together with the carbon atoms bonded thereto, a heteroaromatic ring, whereby $Z^b$ becomes

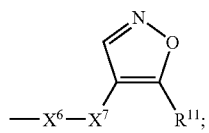

$R^{11}$ is a hydrogen atom, a hydroxyl group, a $C_{1-6}$ alkyl group, a $C_{6-14}$ aryl group (the aryl group is optionally substituted by one or more substituents selected from the group consisting of hydroxyl group and $C_{1-6}$ alkoxy group) or a $C_{6-14}$ aryl-$C_{1-6}$ alkyl group;

$X^8$ is a bond or a $C_{1-6}$ alkylene group;

$R^{17}$ is a hydrogen atom, a halogen atom, —COOAlk, a cyano group, a $C_{1-6}$ alkyl group (the alkyl group is optionally substituted by one or more substituents selected from the group consisting of halogen atom and cyano group), a $C_{6-14}$ aryl group (the aryl group is optionally substituted by one or more substituents selected from the group consist-ing of hydroxyl group and $C_{1-6}$ alkoxy group) or an amino group (the amino group is optionally mono- or di-substituted by $C_{1-6}$ alkyl group(s) (the alkyl group is optionally substituted by one or more $C_{6-14}$ aryl groups));

$X^1$ is a bond or —O—;

$R^1$ is a hydrogen atom, a halogen atom, a cyano group, a $C_{6-14}$ aryl group (the aryl group is optionally substituted by one or more halogen atoms), a $C_{1-6}$ alkyl group (the alkyl group is optionally substituted by one or more substituents selected from the group consisting of halogen atom and —COOAlk) or $Z^a$ as defined in the above-mentioned (1);

$X^2$ is a bond, a $C_{1-6}$ alkylene group,

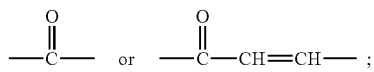

$R^2$ is a hydrogen atom, a halogen atom, a cyano group, an amino group (the amino group is optionally mono- or di-substituted by substituent(s) selected from the group consisting of $C_{1-6}$ alkyl group and $C_{6-14}$ aryl group (the aryl group is optionally substituted by one or more substituents selected from the group consisting of hydroxyl group and $C_{1-6}$ alkoxy group)), a hydroxyl group,

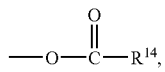

—COOAlk, a $C_{1-6}$ alkoxy group, a $C_{1-6}$ alkyl group (the alkyl group is optionally substituted by one or more halogen atoms), a $C_{6-14}$ aryl group (the aryl group is optionally substituted by one or more substituents selected from the group consisting of halogen atom, cyano group, $C_{1-6}$ alkoxy group and $Z^a$ as defined in the above-mentioned (1));

$R^{14}$ is a hydrogen atom or a $C_{1-6}$ alkyl group; and $Y^1$ and $Y^2$ are the same or different and each is a hydrogen atom, a halogen atom, a hydroxyl group, a $C_{1-6}$ alkoxy group, a $C_{6-14}$ aryl group (the aryl group is optionally substituted by one or more halogen atoms) or

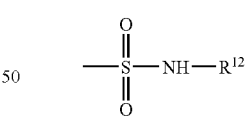

wherein $R^{12}$ is a hydrogen atom or a $C_{1-6}$ alkyl group, or a pharmaceutically acceptable salt thereof.

(5) The compound of the above-mentioned (1), wherein, in the formula (I), $Z$ is $Z^b$ or $Z^d$, $X^6$ is a bond or a $C_{1-6}$ alkylene group;

$X^7$ is —NH—CO—;

$R^9$ is a hydrogen atom or a cyano group;

$R^{10}$ is a hydrogen atom, a hydroxyl group, a $C_{1-6}$ alkyl group or a $C_{6-14}$ aryl group, or $R^9$ and $R^{10}$ optionally form, together with the carbon atoms bonded thereto, a heteroaromatic ring, whereby $Z^b$ becomes

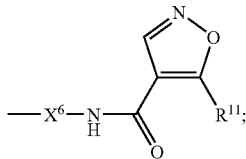

$R^{11}$ is a hydrogen atom, a hydroxyl group or a $C_{1-6}$ alkyl group;

$X^8$ is a bond;

$R^{17}$ is a $C_{1-6}$ alkyl group;

$X^1$ is a bond or —O—;

$R^1$ is a hydrogen atom or a $C_{1-6}$ alkyl group (the alkyl group is optionally substituted one or more substituents selected from the group consisting of halogen atom and —COOAlk);

$X^2$ is a bond;

$R^2$ is a hydrogen atom; and $Y^1$ and $Y^2$ are the same or different and each is a hydrogen atom or

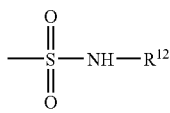

wherein $R^{12}$ is a hydrogen atom or a $C_{1-6}$ alkyl group, or a pharmaceutically acceptable salt thereof.

(6) The compound of the above-mentioned (1), wherein, in the formula (I),

Z is $Z^b$ or $Z^d$, $X^6$ is

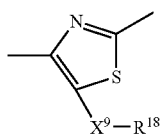

wherein $R^{18}$ is a hydrogen atom, a hydroxyl group, —CHO, —COOAlk or a $C_{1-6}$ alkyl group (the alkyl group is optionally substituted by one or more hydroxyl groups), and $X^9$ is a bond, —CH=N— or —CO—NH—;

$X^7$ is a bond, —HN—CO— or —N=CH—;

$R^9$ is a hydrogen atom or a cyano group;

$R^{10}$ is a hydrogen atom, a hydroxyl group, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group, or $R^9$ and $R^{10}$ optionally form, together with the carbon atoms bonded thereto, a heteroaromatic ring, whereby $Z_b$ becomes

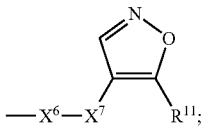

$R^{11}$ is a hydrogen atom, a hydroxyl group, a $C_{1-6}$ alkyl group, a $C_{6-14}$ aryl group (the aryl group is optionally substituted by one or more substituents selected from the group consisting of a hydroxyl group and $C_{1-6}$ alkoxy group) or a $C_{6-14}$ aryl-$C_{1-6}$ alkyl group;

$X^8$ is a bond or a $C_{1-6}$ alkylene group;

$R^{17}$ is a hydrogen atom, a $C_{1-6}$ alkyl group, a $C_{6-14}$ aryl group or an amino group (the amino group is optionally mono- or di-substituted by $Cl_6$ alkyl group(s));

$X^1$ is a bond or —O—;

$R^1$ is a hydrogen atom, a halogen atom, a $C_{6-14}$ aryl group (the aryl group is optionally substituted by one or more halogen atoms) or a $C_{1-6}$ alkyl group;

$X^2$ is a bond;

$R^2$ is a hydrogen atom or a $C_{6-14}$ aryl group (the aryl group is optionally substituted by one or more halogen atoms); and $Y^1$ and $Y^2$ are the same or different and each is a hydrogen atom, a halogen atom, a hydroxyl group, a $C_{1-6}$ alkoxy group or a $C_{6-14}$ aryl group (the aryl group is optionally substituted by one or more halogen atoms) or a pharmaceutically acceptable salt thereof.

(7) The compound of the above-mentioned (1), wherein, in the formula (I)

Z is a group selected from the group consisting of the following formulas $Z^a$, $Z^b$ and $Z^d$;

$X^3$ is a bond or

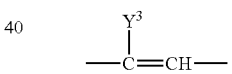

wherein $Y^3$ is a hydrogen atom or a halogen atom;

$R^3$ is a hydrogen atom or a $C_{1-6}$ alkyl group;

$R^4$ is

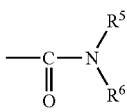

wherein $R^5$ and $R^6$ are the same or different and each is a hydrogen atom, a $C_{1-6}$ alkyl group (the alkyl group is optionally substituted by one or more —COOAlk), a $C_{6-14}$ aryl group (the aryl group is optionally substituted by one or more substituents selected from the group consisting of hydroxyl group, $C_{1-6}$ alkoxy group and —COOAlk), or $R^5$ and $R^6$ optionally form, together with the nitrogen atom bonded thereto, a 5- to 7-membered heterocycle (the heterocycle optionally further has a hetero atom selected from N and O, and is optionally substituted by one or more substituents selected from the group consisting of $C_{1-6}$ alkyl group, $C_{6-14}$ aryl group and $C_{6-14}$ aryl-$C_{1-6}$ alkyl group);

$X^6$ is a bond, a $C_{1-6}$ alkylene group or

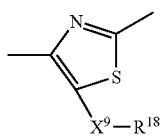

wherein $R^{18}$ is a hydrogen atom, and $X^9$ is a bond;
$X^7$ is a bond, —HN—CO— or —N═CH—;
$R^9$ is a hydrogen atom or a cyano group;
$R^{10}$ is a hydrogen atom, a hydroxyl group, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group;
$R^{11}$ is a hydrogen atom, a hydroxyl group, a $C_{1-6}$ alkyl group;
$X^8$ is a bond;
$R^{17}$ is a hydrogen atom or an amino group (the amino group is optionally mono- or di-substituted by $C_{1-6}$ alkyl group(S) (the alkyl group is optionally substituted by one or more $C_{6-14}$ aryl groups));
$X^1$ is a bond or —O—;
$R^1$ is a hydrogen atom, a $C_{1-6}$ alkoxy group or a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group(s)), sulfanyl group, $C_{6-14}$ arylsulfanyl group (the aryl of the arylsulfanyl group is optionally substituted by one or more halogen atoms) and $C_{6-14}$ aryl group (the aryl group is optionally substituted by one or more substituents selected from the group consisting of hydroxyl group and $C_{1-6}$ alkoxy group)], or $R^1$ is optionally $Z^a$;
$X^2$ is a bond or

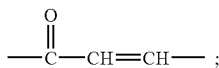

$R^{13}$ is a hydrogen atom, a halogen atom or a $C_{1-6}$ alkyl group;
$R^2$ is a hydrogen atom, a hydroxyl group, a $C_{1-6}$ alkyl group (the alkyl group is optionally substituted by one or more halogen atoms) or a $C_{6-14}$ aryl group (the aryl group is optionally substituted by one or more substituents selected from the group consisting of halogen atom, cyano group, hydroxyl group, $C_{1-6}$ alkoxy group and $Z^a$ (when $Z$ is $Z^b$)); and
$Y^1$ and $Y^2$ are the same or different and each is a hydrogen atom or a halogen atom, or a pharmaceutically acceptable salt thereof.
(8) The compound of the above-mentioned (1), wherein, in the formula (I)
$Z$ is $Z^a$;
$X^3$ is a bond or

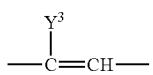

wherein $Y^3$ is a hydrogen atom or a halogen atom;
$R^3$ is a hydrogen atom or a $C_{1-6}$ alkyl group;
$R^4$ is a cyano group, —COOAlk,

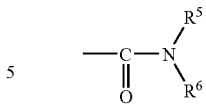

wherein $R^5$ and $R^6$ are the same or different and each is a hydrogen atom, a $C_{1-6}$ alkyl group (the alkyl group is optionally substituted by one or more —COOAlk), a $C_{6-14}$ aryl group (the aryl group is optionally substituted by one or more substituents selected from the group consisting of hydroxyl group, $C_{1-6}$ alkoxy group and —COOAlk), or $R^5$ and $R^6$ optionally form, together with the nitrogen atom bonded thereto, a 5- to 7-membered heterocycle (the heterocycle optionally further has a hetero atom selected from N and O, and is optionally substituted by one or more substituents selected from the group consisting of $C_{1-6}$ alkyl group, $C_{6-14}$ aryl group and $C_{6-14}$ aryl-$C_{1-6}$ alkyl group), or

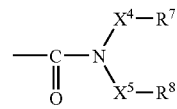

wherein $X^4$, $X^5$ are the same or different and each is a bond or a $C_{1-6}$ alkylene group (the alkylene group is optionally substituted by one or more —COOAlk), and $R^7$ and $R^8$ are the same or different and each is a hydrogen atom, a $C_{6-14}$ aryl group (the $C_{6-14}$ aryl group is optionally substituted by one or more substituents selected from the group consisting of a hydroxyl group and a $C_{1-6}$ alkoxy group) or a $C_{1-6}$ alkylthio group (the alkylthio group is optionally substituted by one or more $C_{6-14}$ aryl groups);
$X^1$ is a bond, —O—,

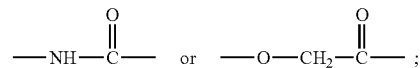

$R^1$ is a hydrogen atom, a halogen atom, an amino group, a $C_{1-6}$ alkoxy group, a $C_{6-14}$ aryl group (the aryl group is optionally substituted by one or more substituents selected from the group consisting of hydroxyl group and $C_{1-6}$ alkoxy group) or a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group(s)) and $C_{6-14}$ aryl group (the aryl group is optionally substituted by one or more substituents selected from the group consisting of hydroxyl group and $C_{1-6}$ alkoxy group)];
$X^2$ is a bond,

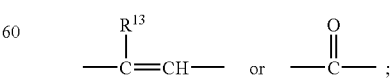

$R^{13}$ is a hydrogen atom or a $C_{1-6}$ alkyl group;
$R^2$ is a hydrogen atom, —COOAlk, a $C_{1-6}$ alkoxy group, a $C_{1-6}$ alkyl group or a $C_{6-14}$ aryl group (the aryl group is optionally substituted by one or more cyano groups); and $Y^1$ and $Y^2$ are the same or different and each is a hydrogen atom, a halogen atom or

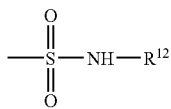

wherein $R^{12}$ is a hydrogen atom, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group (the aryl group of the aryl-alkyl group is optionally substituted by one or more substituents selected from the group consisting of hydroxyl group and $C_{1-6}$ alkoxy group), or a pharmaceutically acceptable salt thereof.

(9) The compound of the above-mentioned (1), wherein, in the formula (I), $Z$ is $Z^b$, $X^6$ is a bond or a $C_{1-6}$ alkylene group;

$X^7$ is —HN—CO—;

$R^9$ is a hydrogen atom or a cyano group;

$R^{10}$ is a hydrogen atom, a hydroxyl group, a $C_{1-6}$ alkyl group or a $C_{6-14}$ aryl group, or $R^9$ and $R^{10}$ optionally form, together with the carbon atoms bonded thereto, a heteroaromatic ring, whereby $Z^b$ becomes

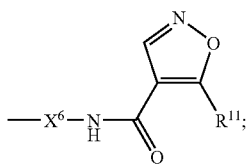

$R^{11}$ is a hydrogen atom, a hydroxyl group or a $C_{1-6}$ alkyl group;

$X^1$ is a bond or —O—;

$R^1$ is a hydrogen atom, a halogen atom, a cyano group, a $C_{1-6}$ alkyl group (the alkyl group is optionally substituted by one or more substituents selected from the group consisting of halogen atom and —COOAlk) or $Z^a$ as defined in the above-mentioned (1);

$X^2$ is a bond, a $C_{1-6}$ alkylene group or

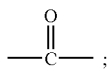

$R^2$ is a hydrogen atom, a cyano group, an amino group, a hydroxyl group,

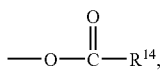

—COOAlk, a $C_{1-6}$ alkoxy group, a $C_{1-6}$ alkyl group, a $C_{6-14}$ aryl group (the aryl group is optionally substituted by one or more substituents selected from the group consisting of halogen atom, cyano group and $Z^a$ as defined in the above-mentioned (1));

$R^{14}$ is a hydrogen atom or a $C_{1-6}$ alkyl group; and $Y^1$ and $Y^2$ are the same or different and each is a hydrogen atom, a halogen atom or

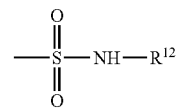

wherein $R^{12}$ is a hydrogen atom or a $C_{1-6}$ alkyl group, or a pharmaceutically acceptable salt thereof.

(10) The compound of the above-mentioned (1), wherein, in the formula (I), $Z$ is $Z^b$, $X^6$ is a bond or a $C_{1-6}$ alkylene group;

$X^7$ is —HN—CO—;

$R^9$ is a hydrogen atom or a cyano group;

$R^{10}$ is a hydrogen atom, a hydroxyl group or a $C_{1-6}$ alkyl group, or $R^9$ and $R^{10}$ optionally form, together with the carbon atoms bonded thereto, a heteroaromatic ring, whereby $Z^b$ becomes

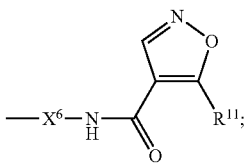

$R^{11}$ is a hydrogen atom, a hydroxyl group or a $C_{1-6}$ alkyl group;

$X^1$ is a bond or —O—;

$R^1$ is a hydrogen atom, a halogen atom, a cyano group, a $C_{1-6}$ alkyl group or $Z^a$ as defined in the above-mentioned (1);

$X^2$ is a bond, a $C_{1-6}$ alkylene group or

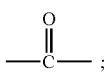

$R^2$ is a hydrogen atom, a cyano group, an amino group, a hydroxyl group,

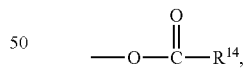

—COOAlk, a $C_{1-6}$ alkoxy group, a $C_{1-6}$ alkyl group, a $C_{6-14}$ aryl group (the aryl group is optionally substituted by one or more substituents selected from the group consisting of halogen atom, cyano group and $Z^a$ as defined in the above-mentioned (1));

$R^{14}$ is a hydrogen atom or a $C_{1-6}$ alkyl group; and $Y^1$ and $Y^2$ are the same or different and each is a hydrogen atom or a halogen atom, or a pharmaceutically acceptable salt thereof.

(11) The compound of the above-mentioned (1), wherein, in the formula (I), $Z$ is $Z^b$, $X^6$ is a bond or a $C_{1-6}$ alkylene group;

$X^7$ is —HN—CO—;

$R^9$ is a hydrogen atom or a cyano group;

$R^{10}$ is a hydrogen atom, a hydroxyl group, a $C_{1-6}$ alkyl group or a $C_{6-14}$ aryl group, or $R^9$ and $R^{10}$ optionally form, together with the carbon atoms bonded thereto, a heteroaromatic ring, whereby $Z^b$ becomes

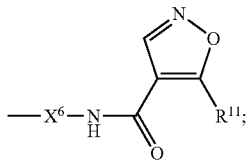

$R^{11}$ is a hydrogen atom, a hydroxyl group or a $C_{1-6}$ alkyl group;

$X^1$ is a bond or —O—;

$R^1$ is a hydrogen atom or a $C_{1-6}$ alkyl group (the alkyl group is optionally substituted one or more substituents selected from the group consisting of halogen atom and —COOAlk);

$X^2$ is a bond;

$R^2$ is a hydrogen atom; and $Y^1$ and $Y^2$ are the same or different and each is a hydrogen atom or

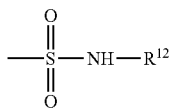

wherein $R^{12}$ is a hydrogen atom or a $C_{1-6}$ alkyl group, or a pharmaceutically acceptable salt thereof.

(12) A prodrug of a compound of the above-mentioned (1) or a pharmaceutically acceptable salt thereof.

(13) A pharmaceutical composition comprising a compound of the above-mentioned (1) or a pharmaceutically acceptable salt thereof or prodrug thereof, and a pharmaceutically acceptable carrier.

(14) The pharmaceutical composition of the above-mentioned (13) which is a leukotriene inhibitor.

(15) The pharmaceutical composition of the above-mentioned (13) which is a BLT2 competitive inhibitor.

(16) The pharmaceutical composition of the above-mentioned (13) which is an agent for the prophylaxis or treatment of allergy.

(17) The pharmaceutical composition of the above-mentioned (13) which is an agent for the prophylaxis or treatment of asthma.

(18) The pharmaceutical composition of the above-mentioned (13) which is an agent for the prophylaxis or treatment of inflammation.

(19) A compound represented by the formula (II)

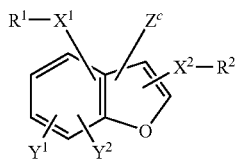

wherein $Z^c$ is a halogen atom,

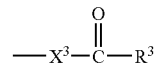

or —$X^6$—$NH_2$;

$R^1$, $R^2$, $R^3$, $X^1$, $X^2$, $X^3$, $X^6$, $Y^1$, $Y^2$ are as defined in the above-mentioned (1), or a salt thereof.

(20) A method for inhibiting leukotriene, which comprises administering an effective amount of a compound of the above-mentioned (1) or a pharmaceutically acceptable salt thereof or a prodrug thereof to a mammal.

(21) Use of a compound of the above-mentioned (1) or a pharmaceutically acceptable salt thereof or a prodrug thereof, for the production of a leukotriene inhibitor.

(22) Use of a compound of the above-mentioned (1) or a pharmaceutically acceptable salt thereof or a prodrug thereof, for the production of an agent for the prophylaxis or treatment of allergy.

The benzofuran compound of the present invention and a pharmaceutically acceptable salt thereof have a superior leukotriene inhibitory action, a BLT2 competitive inhibitory action, a BLT2 blocking action, a prophylactic or therapeutic action on allergy, a prophylactic or therapeutic action on asthma, and a prophylactic or therapeutic action on inflammation, and are useful as agents for the prophylaxis or treatment of diseases such as allergic diseases, asthma, inflammation and the like, and other diseases.

DETAILED DESCRIPTION OF THE INVENTION

The leukotriene inhibitory action in the present invention includes, for example, an action to inhibit binding of leukotriene to leukotriene receptor (e.g., competitive inhibitory action etc.), an action to inhibit production of leukotriene, an action to inhibit leukotriene metabolism, an action to inhibit reaction caused by the action of leukotriene and the like. The leukotriene inhibitory action preferably includes an action to inhibit binding of leukotriene to leukotriene receptor, an action to inhibit reaction caused by the action of leukotriene and the like, more preferably an action to inhibit binding of leukotriene to leukotriene receptor.

In addition, the inhibitory action may be any of an inhibitory action in a molecule unit, an inhibitory action in a cell unit, an inhibitory action in a tissue unit and an inhibitory action in an individual unit.

Leukotriene in the present invention includes, for example, leukotriene A4 (LTA4), leukotriene B4 (LTB4), leukotriene C4 (LTC4), leukotriene D4 (LTD4), metabolites thereof and the like, and includes any compound capable of binding to a leukotriene receptor (leukotriene receptor ligand). Leukotriene is preferably leukotriene B4.

As the leukotriene B4 receptor, BLT1, BLT2 and the like can be mentioned, which are free of any particular limitation. Leukotriene B4 receptor is preferably BLT2.

That is, the compound of the present invention is superior in the action of inhibiting binding of LTB4 to BLT2 (BLT2 competitive inhibitory action) or inhibiting reactions caused by the action of LTB4 via BLT2 (BLT2 blocking action).

That the above-mentioned BLT2 competitive inhibitory action is BLT2 specific means that the action of inhibiting binding of LTB4 to BLT2 is stronger than the action of inhibiting LTB4 from binding to other LTB4 receptor (e.g., BLT1).

That the BLT2 blocking action is BLT2 specific means that the action of inhibiting reactions caused by the action of LTB4 via BLT2 is stronger than the action of inhibiting reactions caused by the action via other LTB4 receptor (e.g., BLT1).

Each symbol used in the present description is explained in the following.

In the formula (I), substituent Z may substitute at any substitutable position on the benzofuran ring, and the substitutable position is, for example, the 2-, 3-, 4-, 5-, 6- or 7-position, preferably the 2-, 3-, 4-, 5- or 7-position, more preferably the 2-, 3-, 4- or 5-position.

Here, when Z is $Z^a$, the substitutable position is preferably the 2-, 4-, 5- or 7-position, more preferably the 2-, 4- or 5-position.

When Z is $Z^b$, the substitutable position is preferably the 2-, 3- or 4-position.

When Z is $Z^d$, the substitutable position is preferably the 2-, 3- or 4-position.

Substituent —$X^1$—$R^1$ may substitute at any substitutable position on the benzofuran ring, and the substitutable position is, for example, the 2-, 3-, 4-, 5-, 6- or 7-position, preferably the 3-, 5-, 6- or 7-position.

Substituent —$X^2$—$R^2$ can substitute at the 2- or 3-position on the benzofuran ring.

Substituent $Y^1$ or $Y^2$ may substitute at any substitutable position on the benzofuran ring, and the substitutable position is, for example, the 2-, 3-, 4-, 5-, 6- or 7-position, preferably is the 2-, 3-, 4-, 5- or 6-positoin.

In a different aspect, substituent $Y^1$ or $Y^2$ can substitute at the 4-, 5-, 6- or 7-position, preferably the 4-, 5- or 6-position.

In the present invention, unless particularly specified, the position of the substituent is not particularly limited as long as it is a substitutable position.

As the halogen atom for $Y^3$, a fluorine atom, a chlorine atom, a bromine atom, an iodine atom and the like can be mentioned. Preferred is a chlorine atom.

As the $C_{1-6}$ alkyl group for $R^3$, for example, methyl, ethyl, propyl, isopropyl, butyl, isobutyl, sec-butyl, tert-butyl, pentyl, isopentyl, neopentyl, hexyl and the like can be mentioned. Preferred are methyl and ethyl, and more preferred is methyl.

As preferable —COOAlk for $R^4$, —COOH, —COOCH$_3$, —COOC$_2$H$_5$ and the like can be mentioned. More preferred are —COOH and —COOC$_2$H$_5$, and still more preferred is —COOC$_2$H$_5$.

As the $C_{6-14}$ aryl group for $R^4$, for example, phenyl, naphthyl and the like can be mentioned. Preferred is phenyl. The aryl group is optionally substituted by one or more halogen atoms. As the halogen atom, a fluorine atom, a chlorine atom, a bromine atom, an iodine atom and the like can be mentioned. Preferred is a chlorine atom. The number of substituents is, for example, 0-3, preferably 0-2, more preferably 0-1. As used herein, the number of substituents of 0 means that $R^4$ is an unsubstituted $C_{6-14}$ aryl group.

As the $C_{1-6}$ alkyl group for $R^5$ or $R^6$, for example, methyl, ethyl, propyl, isopropyl, butyl, isobutyl, sec-butyl, tert-butyl, pentyl, isopentyl, neopentyl, hexyl and the like can be mentioned. Preferred are methyl, ethyl, propyl and isopropyl.

The aforementioned $C_{1-6}$ alkyl group is optionally substituted by one or more —COOAlk. As preferable —COOAlk, —COOH, —COOCH$_3$, —COOC$_2$H$_5$ and the like can be mentioned, and more preferred is —COOC$_2$H$_5$. The number of substituents is preferably 0-1. As used herein, the number of substituents of 0 means that $R^5$ and $R^6$ are unsubstituted $C_{1-6}$ alkyl groups.

As the $C_6r_{14}$ aryl group for $R^5$ or $R^6$, for example, phenyl, naphthyl and the like can be mentioned. Preferred is phenyl. The $C_{6-14}$ aryl group is optionally substituted by one or more substituents selected from the group consisting of hydroxyl group, $C_{1-6}$ alkoxy group and —COOAlk. The $C_{1-6}$ alkoxy group is a linear or branched chain alkoxy group, which may have one oxygen, such as methoxy, ethoxy and propoxy, or two oxygens, such as methylenedioxy, with preference given to methoxy. As the aforementioned —COOAlk, —COOH, —COOCH$_3$, —COOC$_2$H$_5$ and the like can be mentioned, and preferred is —COOC$_2$h$_5$. The number of substituents is preferably 0-2. As used herein, the number of substituents of 0 means that $R^5$ and $R^6$ are unsubstituted $C_{6-14}$ aryl groups.

The number of N or O that may be further contained in the 5- to 7-membered heterocycle which $R^5$ and $R^6$ optionally form, together with the nitrogen atom bonded thereto, is, for example, 0-2, preferably 0 or 1. As the heterocycle, for example, pyrrolidine, piperidine, azepane, piperazine, hexahydropyrimidine, hexahydropyridazine, imidazolidine, pyrazolidine, [1,4]diazepan, [1,3]diazepan, [1,2]diazepan, morpholine, [1,3]oxazinan, [1,2]oxazinan, oxazolidine, isoxazolidine, [1,4]oxazepan, [1,3]oxazepan, [1,2]oxazepan and the like can be mentioned. Preferred are piperidine, piperazine and morpholine.

The heterocycle is optionally substituted by one or more substituents selected from the group consisting of $C_{1-6}$ alkyl group, $C_{6-14}$ aryl group and $C_{6-14}$ aryl-$C_{1-6}$ alkyl group. As the aforementioned $C_{1-6}$ alkyl group, for example, methyl, ethyl, propyl, isopropyl, butyl, isobutyl, sec-butyl, tert-butyl, pentyl, isopentyl, neopentyl, hexyl and the like can be mentioned. Preferred is methyl. As the aforementioned $C_{6-14}$ aryl group, for example, phenyl, naphthyl and the like can be mentioned, and preferred is phenyl. As the $C_{6-14}$ aryl moiety of the aforementioned $C_{6-14}$ aryl-$C_{1-6}$ alkyl group, for example, phenyl, naphthyl and the like can be mentioned, and preferred is phenyl. As the $C_{1-6}$ alkyl moiety, for example, methyl, ethyl, propyl, isopropyl, butyl, isobutyl, sec-butyl, tert-butyl, pentyl, isopentyl, neopentyl, hexyl and the like can be mentioned, and preferred is methyl. The number of substituents on the heterocycle is, for example, 0-3, preferably 0 or 1. As used herein, the number of substituents of 0 means that $R^5$ and $R^6$ form, together with the nitrogen atom bonded thereto, an unsubstituted heterocycle. While the position(s) of substituents on the heterocycle is not particularly limited, when the heterocycle further contains N, N is preferably substituted.

The $C_{1-6}$ alkylene group for $X^4$ or $X^5$ is a linear or a branched chain alkylene group, and, for example, methylene, ethylene, —CH(CH$_3$)—, trimethylene, propylene, tetramethylene, pentamethylene, hexamethylene and the like can be mentioned. Preferred are methylene and ethylene.

The aforementioned $C_{1-6}$ alkylene group is optionally substituted by one or more —COOAlk. As preferable —COOAlk, —COOH, —COOCH$_3$, —COOC$_2$H$_5$ and the like can be mentioned, and more preferred is —COOC$_2$H$_5$. The number of substituents is, for example, 0-3, preferably 0 or 1. As used herein, the number of substituents of 0 means that $X^4$ and $X^5$ are unsubstituted $C_{1-6}$ alkylene groups.

As the $C_{6-14}$ aryl group for $R^7$ or $R^8$, for example, phenyl, naphthyl and the like can be mentioned, and preferred is phenyl. The $C_{6-14}$ aryl group is optionally substituted by one or more substituents selected from the group consisting of hydroxyl group and $C_{1-6}$ alkoxy group. The aforementioned $C_{1-6}$ alkoxy group is a linear or branched chain alkoxy group, which may have one oxygen, such as methoxy, ethoxy and propoxy, or two oxygens, such as methylenedioxy. Preferred are methoxy and methylenedioxy, and more preferred is methoxy. The number of substituents is, for example, 0-3, preferably 0-2. As used herein, the number of substituents of 0 means that $R^7$ and $R^8$ are unsubstituted $C_{6-14}$ aryl groups.

As the $C_{1-6}$ alkylthio group for $R^7$ or $R^8$, for example, methylthio, ethylthio, propylthio, isopropylthio, butylthio, isobutylthio, sec-butylthio, tert-butylthio, pentylthio, isopentylthio, neopentylthio, hexylthio and the like can be mentioned, and preferred is methylthio.

The alkylthio group is optionally substituted by one or more $C_{6-14}$ aryl groups. As the aforementioned $C_{6-14}$ aryl group, for example, phenyl, naphthyl and the like can be mentioned, and preferred is phenyl. The number of substituents is, for example, 0-3, preferably 0 or 1. As used herein, the number of substituents of 0 means that $R^7$ and $R^8$ are unsubstituted alkylthio groups.

The $C_{1-6}$ alkylene group for $X^6$ is a linear or branched chain alkylene group, and, for example, methylene, ethylene, —CH(CH$_3$)—, trimethylene, propylene, tetramethylene, pentamethylene, hexamethylene and the like can be mentioned. Preferred are methylene, ethylene and —CH(CH$_3$)—, and more preferred is —CH(CH$_3$)—.

As —COOAlk for $R^{18}$, —COOH, —COOCH$_3$, —COOC$_2$H$_5$ and the like can be mentioned. Preferred are —COOH and —COOC$_2$H$_5$.

As the $C_{1-6}$ alkyl group for $R^{18}$, for example, methyl, ethyl, propyl, isopropyl, butyl, isobutyl, sec-butyl, tert-butyl, pentyl, isopentyl, neopentyl, hexyl and the like can be mentioned. Preferred are methyl and ethyl. The alkyl group is optionally substituted by one or more hydroxyl groups. The number of substituents is not particularly limited, and, is for example, 0-3, preferably 0 or 1. As used herein, the number of substituents of 0 means that $R^{18}$ is an unsubstituted $C_{1-6}$ alkyl group.

As the $C_{1-6}$ alkyl group for $R^{10}$, for example, methyl, ethyl, propyl, isopropyl, butyl, isobutyl, sec-butyl, tert-butyl, pentyl, isopentyl, neopentyl, hexyl and the like can be mentioned. Preferred are methyl and ethyl, and more preferred is methyl.

As the $C_{6-14}$ aryl group for $R^{10}$, for example, phenyl, naphthyl and the like can be mentioned, and preferred is phenyl. The aryl group is optionally substituted by one or more substituents selected from the group consisting of hydroxyl group and $C_{1-6}$ alkoxy group. The alkoxy group as a substituent is a linear or branched chain alkoxy group, which may have one oxygen, such as methoxy, ethoxy and propoxy, or two oxygens, such as methylenedioxy, with preference given to methoxy. The number of substituents is not particularly limited, and, is for example, 0-3, preferably 0 or 1. As used herein, the number of substituents of 0 means that $R^{10}$ is an unsubstituted $C_{6-14}$ aryl group.

As the $C_{6-14}$ aryl moiety of the $C_{6-14}$ aryl-$C_{1-6}$ alkyl group for $R^{10}$, for example, phenyl, naphthyl and the like can be mentioned, and preferred is phenyl. As the $C_{1-6}$ alkyl moiety, for example, methyl, ethyl, propyl, isopropyl, butyl, isobutyl, sec-butyl, tert-butyl, pentyl, isopentyl, neopentyl, hexyl and the like can be mentioned, and preferred are methyl and ethyl.

As the $C_{1-6}$ alkyl group for $R^{11}$, for example, methyl, ethyl, propyl, isopropyl, butyl, isobutyl, sec-butyl, tert-butyl, pentyl, isopentyl, neopentyl, hexyl and the like can be mentioned. Preferred are methyl and ethyl, and more preferred is methyl.

As the $C_{6-14}$ aryl group for $R^{11}$, for example, phenyl, naphthyl and the like can be mentioned, and preferred is phenyl. The aryl group is optionally substituted by one or more substituents selected from the group consisting of hydroxyl group and $C_{1-6}$ alkoxy group. The alkoxy group as a substituent is a linear or branched chain alkoxy group, which may have one oxygen, such as methoxy, ethoxy and propoxy, or two oxygens, such as methylenedioxy, with preference given to methoxy. The number of substituents is not particularly limited, and, is for example, 0-3, preferably 0 or 1. As used herein, the number of substituents of 0 means that $R^{11}$ is an unsubstituted $C_{6-14}$ aryl group.

As the $C_{6-14}$ aryl moiety of the $C_{6-14}$ aryl-$C_{1-6}$ alkyl group for $R^{11}$, for example, phenyl, naphthyl and the like can be mentioned, and preferred is phenyl. As the $C_{1-6}$ alkyl moiety, for example, methyl, ethyl, propyl, isopropyl, butyl, isobutyl, sec-butyl, tert-butyl, pentyl, isopentyl, neopentyl, hexyl and the like can be mentioned, and preferred are methyl and ethyl.

The $C_{1-6}$ alkylene group for $X^8$ is a linear or branched chain alkylene group, and, for example, methylene, ethylene, —CH(CH$_3$)—, trimethylene, propylene, tetramethylene, pentamethylene, hexamethylene and the like can be mentioned, and preferred are methylene and ethylene.

As the halogen atom for $R^{17}$, a fluorine atom, a chlorine atom, a bromine atom, an iodine atom and the like can be mentioned, and preferred is a chlorine atom.

As preferable —COOAlk for $R^{17}$, —COOH, —COOCH$_3$, —COOC$_2$H$_5$ and the like can be mentioned. More preferred are —COOH and —COOC$_2$H$_5$, and still more preferred is —COOC$_2$H$_5$.

As the $C_{1-6}$ alkyl group for $R^{17}$, for example, methyl, ethyl, propyl, isopropyl, butyl, isobutyl, sec-butyl, tert-butyl, pentyl, isopentyl, neopentyl, hexyl and the like can be mentioned, and preferred are methyl and ethyl. The alkyl group is optionally substituted by one or more substituents selected from the group consisting of halogen atom and cyano group. The number of substituents is not particularly limited, and, is for example, 0-3, preferably 0 or 1. As used herein, the number of substituents of 0 means that R is an unsubstituted $C_{1-6}$ alkyl group.

As the $C_{6-14}$ aryl group for $R^{17}$, for example, phenyl, naphthyl and the like can be mentioned, and preferred is phenyl. The aryl group is optionally substituted by one or more substituents selected from the group consisting of hydroxyl group and $C_{1-6}$ alkoxy group. The alkoxy group as a substituent is a linear or branched chain alkoxy group, which may have one oxygen, such as methoxy, ethoxy and propoxy, or two oxygens, such as methylenedioxy, with preference given to methoxy. The number of substituents is not particularly limited, and, is for example, 0-3. As used herein, the number of substituents of 0 means that $R^{17}$ is an unsubstituted $C_{6-14}$ aryl group.

When $R^{17}$ is an amino group, the amino group is optionally mono- or di-substituted by $C_{1-6}$ alkyl group(s). As the alkyl group as a substituent, for example, methyl, ethyl, propyl, isopropyl, butyl, isobutyl, sec-butyl, tert-butyl, pentyl, isopentyl, neopentyl, hexyl and the like can be mentioned, and preferred are methyl and ethyl.

The alkyl group as a substituent is optionally substituted by one or more $C_{6-14}$ aryl groups. As the aryl group, for example, phenyl, naphthyl and the like can be mentioned, and preferred is phenyl. The number of substituents is not particularly limited, and, is for example, 0-3, preferably 0 or 1. As used herein, the number of substituents of 0 means that the $C_{1-6}$ alkyl group as a substituent is not substituted.

As the $C_{1-6}$ alkoxy group for $R^1$, methoxy, ethoxy, propoxy, isopropoxy, butoxy, isobutoxy, sec-butoxy, tert-butoxy, pentyloxy, isopentyloxy, neopentyloxy and the like can be mentioned, and preferred are methoxy and ethoxy.

As the $C_{6-14}$ aryl group for $R^1$, for example, phenyl, naphthyl and the like can be mentioned, and preferred is phenyl. The $C_{6-14}$ aryl group is optionally substituted by one or more substituents selected from the group consisting of hydroxyl group, halogen atom and $C_{1-6}$ alkoxy group. The aforementioned $C_{1-6}$ alkoxy group is a linear or branched chain alkoxy group, which may have one oxygen, such as methoxy, ethoxy and propoxy, or two oxygens, such as methylenedioxy. Preferred are methoxy and methylenedioxy, and more preferred is methoxy. The number of substituents is, for example, 0-3, preferably 0-2. As used herein, the number of substituents of 0 means that $R^1$ is an unsubstituted $C_{6-14}$ aryl group.

As the $C_{1-6}$ alkyl group for $R^1$, for example, methyl, ethyl, propyl, isopropyl, butyl, isobutyl, sec-butyl, tert-butyl, pentyl, isopentyl, neopentyl, hexyl and the like can be mentioned, and preferred are methyl, ethyl, propyl and isopropyl.

The alkyl group is optionally substituted by one or more substituents selected from the group consisting of halogen atom, —COOAlk, amino group, sulfanyl group, $C_{6-14}$ arylsulfanyl group and $C_{6-14}$ aryl group. As the halogen atom which may substitute the alkyl group, a fluorine atom, a chlorine atom, a bromine atom, an iodine atom and the like can be mentioned, and preferred is a chlorine atom.

As preferable —COOAlk that may substitute the alkyl group, —COOH, —COOCH$_3$, —COOC$_2$H$_5$ and the like can be mentioned.

The amino group which may substitute the alkyl group is optionally mono- or di-substituted by $C_{1-6}$ alkyl group(s). As the $C_{1-6}$ alkyl group which may substitute the amino group, for example, methyl, ethyl, propyl, isopropyl, butyl, isobutyl, sec-butyl, tert-butyl, pentyl, isopentyl, neopentyl, hexyl and the like can be mentioned, and preferred are methyl and ethyl. That is, as the amino group, —NH$_2$, —NH(CH$_3$), —N(CH$_3$)$_2$, —N(C$_2$H$_5$)$_2$ and the like are preferable.

As the $C_{6-14}$ aryl moiety of the $C_{6-14}$ arylsulfanyl group which may substitute the $C_{1-6}$ alkyl group for $R^1$, for example, phenyl, naphthyl and the like can be mentioned, and preferred is phenyl. The aryl is optionally substituted by one or more halogen atoms. As the halogen atom, a fluorine atom, a chlorine atom, a bromine atom, an iodine atom and the like can be mentioned, and preferred is a chlorine atom. The number of the halogen atoms which substitute the aryl is not particularly limited and is, for example, 0-3, preferably 0 or 1. As used herein, the number of substituents of 0 means that $C_{6-14}$ aryl moiety of the $C_{6-14}$ arylsulfanyl group which may substitute the $C_{1-6}$ alkyl group for $R^1$, is not substituted.

As the $C_{6-14}$ aryl group which may substitute the $C_{1-6}$ alkyl group for $R^1$, for example, phenyl, naphthyl and the like can be mentioned, and preferred is phenyl. The aforementioned $C_{6-14}$ aryl group is optionally substituted by one or more substituents selected from the group consisting of hydroxyl group and $C_{1-6}$ alkoxy group. The aforementioned $C_{1-6}$ alkoxy group is a linear or branched chain alkoxy group, which may have one oxygen, such as methoxy, ethoxy and propoxy, or two oxygens, such as methylenedioxy, with preference given to methoxy. The number of substituents for the aryl group is, for example, 0-3, preferably 0 or 1. As used herein, the number of substituents of 0 means that the aforementioned $C_{6-14}$ aryl group is an unsubstituted $C_{6-14}$ aryl group.

The number of substituents for the $C_{1-6}$ alkyl group for $R^1$ is, for example, 0-3, preferably 0-2. As used herein, the number of substituents of 0 means that $R^1$ is an unsubstituted alkyl group.

In the formula (I), when Z is $Z^b$, then $R^1$ may be $Z^a$ In this case, the substituents $Z^a$ and $Z^b$ are simultaneously present in the side chain bonded to the benzofuran skeleton in the formula (I). In this case, $X^1$ is preferably a bond, $X^3$ in $Z^a$ for $R^1$, is preferably a bond, and $R^3$ is preferably a methyl group. $R^4$ is preferably

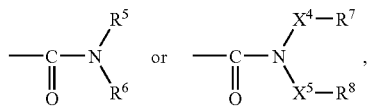

wherein $R^5$ and $R^6$ are each preferably a hydrogen atom or an ethyl group, or $R^5$ and $R^6$ form, together with the nitrogen atom bonded thereto, piperazine or morpholine, each optionally substituted by phenyl(s), $X^4$ and $X^5$ are each preferably a bond, a methylene group or an ethylene group, and $R^7$ and $R^8$ are each preferably a hydrogen atom or a phenyl group optionally mono- or di-substituted by methoxy group(s).

In a different aspect, $R^1$ may be $Z^a$. In this case, the substituents Z ($Z^a$, $Z^b$ or $Z^d$) and $Z^a$ are simultaneously present in the side chain bonded to the benzofuran skeleton in the formula (I). Here, $Z^a$ for the substituent Z and $Z^a$ for $R^1$ in the formula (I) may be the same or different, within the scope of the aforementioned definitions. In this case, $X^1$ is preferably a bond, $X^3$ in $Z^a$ for $R^1$, is preferably a bond, and $R^3$ is preferably a methyl group. $R^4$ is preferably —COOAlk (e.g., —COOH, —COOCH$_3$, —COOC$_2$H$_5$ and the like),

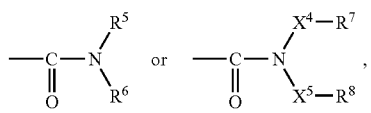

wherein $R^5$ and $R^6$ are each preferably a hydrogen atom or an ethyl group, or $R^5$ and $R^6$ form, together with the nitrogen atom bonded thereto, piperazine or morpholine, each optionally substituted by phenyl(s), $X^4$ and $X^5$ are each preferably a bond, a methylene group or an ethylene group, and $R^7$ and $R^8$ are each preferably a hydrogen atom or a phenyl group optionally mono- or di-substituted by methoxy group(s).

The $C_{1-6}$ alkylene group for $X^2$ is a linear or branched chain alkylene group, and, for example, methylene, ethylene, —CH(CH$_3$)—, trimethylene, propylene, butylene, tetramethylene, pentamethylene, hexamethylene and the like can be mentioned. Preferred are methylene, ethylene, propylene, butylenes and —CH(CH$_3$)—, and more preferred is —CH(CH$_3$)—.

As the $C_{1-6}$ alkyl group for $R^{13}$, for example, methyl, ethyl, propyl, isopropyl, butyl, isobutyl, sec-butyl, tert-butyl, pentyl, isopentyl, neopentyl, hexyl and the like can be mentioned, and preferred is methyl.

As the halogen atom for $R^{13}$, a fluorine atom, a chlorine atom, a bromine atom, an iodine atom and the like can be mentioned, and preferred is a chlorine atom.

When $R^2$ is an amino group, the amino group is optionally mono- or di-substituted by substituent(s) selected from the group consisting of $C_{1-6}$ alkyl group and $C_{6-14}$ aryl group. As the $C_{1-6}$ alkyl group as a substituent, for example, methyl, ethyl, propyl, isopropyl, butyl, isobutyl, sec-butyl, tert-butyl, pentyl, isopentyl, neopentyl, hexyl and the like can be mentioned, and preferred are methyl and ethyl.

As the $C_{6-14}$ aryl group which is a substituent of the amino group for $R^2$, for example, phenyl, naphthyl and the like can be mentioned, and preferred is phenyl. The $C_{6-14}$ aryl group is optionally substituted by one or more substituents selected from the group consisting of hydroxyl group and $C_{1-6}$ alkoxy group. The aforementioned $C_{1-6}$ alkoxy group is a linear or branched chain alkoxy group, which may have one oxygen, such as methoxy, ethoxy and propoxy, or two oxygens, such as methylenedioxy, with preference given to methoxy. The number of the substituents for the aryl group is, for example, 0-3, preferably 0 or 1. As used herein, the number of substituents of 0 means that the aforementioned $C_{6-14}$ aryl group is an unsubstituted $C_{6-14}$ aryl group.

As preferable —COOAlk for $R^2$, —COOH, —COOCH$_3$, —COOC$_2$H$_5$ and the like can be mentioned, and more preferred are —COOH and —COOC$_2$H$_5$.

As the $C_{1-6}$ alkoxy group for $R^2$, methoxy, ethoxy, propoxy, isopropoxy, butoxy, isobutoxy, sec-butoxy, tert-butoxy, pentyloxy, isopentyloxy, neopentyloxy and the like can be mentioned, and preferred are methoxy and ethoxy.

As the $C_{1-6}$ alkyl group for $R^2$, for example, methyl, ethyl, propyl, isopropyl, butyl, isobutyl, sec-butyl, tert-butyl, pentyl, isopentyl, neopentyl, hexyl and the like can be mentioned, and preferred is methyl. The alkyl group is optionally substituted by one or more halogen atoms. As the halogen atom, a fluorine atom, a chlorine atom, a bromine atom, an iodine atom and the like can be mentioned, and preferred are a chlorine atom and a bromine atom. The number of substituents of the alkyl group is, for example, 0-3, preferably 0 or 1. As used herein, the number of substituents of 0 means that $R^2$ is an unsubstituted $C_{1-6}$ alkyl group.

As the $C_{6-14}$ aryl group for $R^2$, for example, phenyl, naphthyl and the like can be mentioned, with preference given to phenyl. The aryl group is optionally substituted by one or more substituents selected from the group consisting of halogen atom, cyano group, hydroxyl group, $C_{1-6}$ alkoxy group and $Z^a$ (when Z is $Z^b$) As the halogen atom as a substituent, a fluorine atom, a chlorine atom, a bromine atom, an iodine atom and the like can be mentioned, with preference given to a chlorine atom and a bromine atom.

As the $C_{1-6}$ alkoxy group as a substituent, methoxy, ethoxy, propoxy, isopropoxy, butoxy, isobutoxy, sec-butoxy, tert-butoxy, pentyloxy, isopentyloxy, neopentyloxy and the like can be mentioned, with preference given to methoxy and ethoxy.

When Z in the formula (I) is $Z^b$, $Z^a$ optionally substitutes aryl group for $R^2$, wherein $X^2$ is preferably

and the aryl group is phenyl. $X^3$ in $Z^a$ for $R^2$ is preferably a bond, and $R^3$ is preferably a methyl group. Preferable $R^4$ is

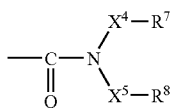

wherein $X^4$ and $X^5$ are each preferably a bond, a methylene group or an ethylene group, and $R^7$ and $R^8$ are each preferably a hydrogen atom or a phenyl group optionally mono- or di-substituted by methoxy group(s).

While the number of substituents of $C_{6-14}$ aryl group for $R^2$ is not particularly limited, it is, for example, 0-3, preferably 0 or 1. The number of substituents of 0 means that the aryl group for $R^2$ is a unsubstituted aryl group.

As the $C_{1-6}$ alkyl group for $R^{14}$, for example, methyl, ethyl, propyl, isopropyl, butyl, isobutyl, sec-butyl, tert-butyl, pentyl, isopentyl, neopentyl, hexyl and the like can be mentioned, with preference given to methyl.

As the halogen atom for $Y^1$ or $Y^2$, a fluorine atom, a chlorine atom, a bromine atom, an iodine atom and the like can be mentioned, with preference given to a bromine atom.

As the $C_{1-6}$ alkoxy group for $Y^1$ or $Y^2$, methoxy, ethoxy, propoxy, isopropoxy, butoxy, isobutoxy, sec-butoxy, tert-butoxy, pentyloxy, isopentyloxy, neopentyloxy and the like can be mentioned, with preference given to methoxy and ethoxy.

As the $C_{6-14}$ aryl group for $Y^1$ or $Y^2$, for example, phenyl, naphthyl and the like can be mentioned, with preference given to phenyl. The aryl group is optionally substituted by one or more halogen atoms. As the halogen atom as a substituent, a fluorine atom, a chlorine atom, a bromine atom, an iodine atom and the like can be mentioned, with preference given to a chlorine atom and a bromine atom. While the number of substituents of the $C_{6-14}$ aryl group is not particularly limited, it is, for example, 0-3, preferably 0 or 1. The number of substituents of 0 means that aryl group for $R^2$ is an unsubstituted aryl group.

As the $C_{1-6}$ alkyl group for $R^{12}$, for example, methyl, ethyl, propyl, isopropyl, butyl, isobutyl, sec-butyl, tert-butyl, pentyl, isopentyl, neopentyl, hexyl and the like can be mentioned, with preference given to methyl and ethyl.

As the $C_{6-14}$ aryl group for $R^{12}$, for example, phenyl, naphthyl and the like can be mentioned, with preference given to phenyl. The aryl group is optionally substituted by one or more substituents selected from the group consisting of hydroxyl group and $C_{1-6}$ alkoxy group. The aforementioned $C_{1-6}$ alkoxy group is a linear or branched chain alkoxy group, which may have one oxygen, such as methoxy, ethoxy and propoxy, or two oxygens, such as methylenedioxy, with preference given to methoxy. The number of substituents of the aryl group is, for example, 0-3, preferably 0-2. As used herein, the number of substituents of 0 means that $R^{12}$ is an unsubstituted $C_{6-14}$ aryl group.

As the $C_{6-14}$ aryl moiety of the $C_{6-14}$ aryl-$C_{1-6}$ alkyl group for $R^{12}$, for example, phenyl, naphthyl and the like can be mentioned, with preference given to phenyl. The $C_{6-14}$ aryl moiety is optionally substituted by one or more substituents selected from the group consisting of hydroxyl group and $C_{1-6}$ alkoxy group, and the aforementioned $C_{1-6}$ alkoxy group is a linear or branched chain alkoxy group, which may have one oxygen, such as methoxy, ethoxy and propoxy, or two oxygens, such as methylenedioxy, with preference given to methoxy. The number of substituents of the $C_{6-14}$ aryl moiety is, for example, 0-3, preferably 0-2. As used herein, the number of substituents of 0 means that the $C_{6-14}$ aryl moiety is an unsubstituted $C_{6-14}$ aryl. As the $C_{1-6}$ alkyl moiety of the aryl-alkyl group, for example, methyl, ethyl, propyl, isopropyl, butyl, isobutyl, sec-butyl, tert-butyl, pentyl, isopentyl, neopentyl, hexyl and the like can be mentioned, with preference given to methyl and ethyl.

In the formula (II), as the halogen atom for $Z^c$, a fluorine atom, a chlorine atom, a bromine atom, an iodine atom and the like can be mentioned, with preference given to a bromine atom.

The benzofuran compound of the present invention preferably contains at least one —NH—CO— or —CO—NH— in Z to enhance its leukotriene inhibitory action, its BLT2 competitive inhibitory action or BLT2 blocking action.

Furthermore, it is preferable to have, in the compound, at least one double bond capable of conjugating with the —NH—CO— or —CO—NH—.

In a still another aspect, to achieve potent leukotriene inhibitory activity, or potent BLT2 competitive inhibitory activity or BLT2 blocking action, or specificity for BLT2, the compound of the present invention may be a compound of the above-mentioned formula (I), wherein Z is a group selected from the group consisting of the following formulas $Z^a$, $Z^b$ and $Z^d$;

$X^3$ is a bond or

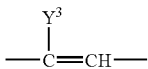

($Y^3$ is a hydrogen atom or a halogen atom)
$R^3$ is a hydrogen atom or a $C_{1-6}$ alkyl group;
$R^4$ is

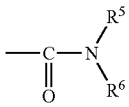

[$R^5$ and $R^6$ are the same or different and each is a hydrogen atom, a $C_{1-6}$ alkyl group (the alkyl group is optionally substituted by one or more —COOAlk), a $C_{6-14}$ aryl group (the aryl group is optionally substituted by one or two or more substituents selected from the group consisting of hydroxyl group, $C_{1-6}$ alkoxy group and —COOAlk), or $R^5$ and $R^6$ optionally form, together with the nitrogen atom bonded thereto, a 5- to 7-membered heterocycle (the heterocycle optionally further has a hetero atom selected from N and O, and is optionally substituted by one or more substituents selected from the group consisting of $C_{1-6}$ alkyl group, $C_{6-14}$ aryl group and $C_{6-14}$ aryl-$C_{1-6}$ alkyl group)];
$X^6$ is a bond, a $C_{1-6}$ alkylene group or

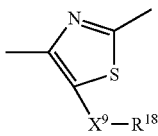

[$R^{18}$ is a hydrogen atom and $X^9$ is a bond];
$X^7$ is a bond, —HN—CO— or —N=CH—;
$R^9$ is a hydrogen atom or a cyano group;
$R^{10}$ is a hydrogen atom, a hydroxyl group, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group;
$R^{11}$ is a hydrogen atom, a hydroxyl group or a $C_{1-6}$ alkyl group;
$X^8$ is a bond;
$R^{17}$ is a hydrogen atom or an amino group (the amino group is optionally mono- or di-substituted by $C_{1-6}$ alkyl group(s) (the alkyl group is optionally substituted by one or more $C_{6-14}$ aryl groups));
$X^1$ is a bond or —O—;
$R^1$ is a hydrogen atom, a $C_{1-6}$ alkoxy group or a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group(s)), sulfanyl group, $C_{6-14}$ arylsulfanyl group (the aryl of the arylsulfanyl group is optionally substituted by one or more halogen atoms) and $C_{6-14}$ aryl group (the aryl group is optionally substituted by one or more substituents selected from the group consisting of hydroxyl group and $C_{1-6}$ alkoxy group)], or $R^1$ is optionally $Z^a$;

$X^2$ is a bond or

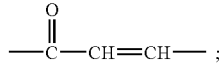

$R^{13}$ is a hydrogen atom, a halogen atom or a $C_{1-6}$ alkyl group;
$R^2$ is a hydrogen atom, a hydroxyl group, a $C_{1-6}$ alkyl group (the alkyl group is optionally substituted by one or more halogen atoms), a $C_{6-14}$ aryl group (the aryl group is optionally substituted by one or more substituents selected from the group consisting of halogen atom, cyano group, hydroxyl group, $C_{1-6}$ alkoxy group and $Z^a$ (when Z is $Z^b$));
$Y^1$ and $Y^2$ are the same or different and each is a hydrogen atom or a halogen atom.

Specific examples of preferable benzofuran compound (I) and a pharmaceutically acceptable salt thereof include (1) (E)-3-[2-acetyl-7-(1-phenylethoxy)benzofuran-4-yl]-N,N-diethyl-2-butenamide
(2) (E)-3-[7-(3-carboxypropoxy)-4-(2-diethylcarbamoyl-1-methylvinyl)benzofuran-2-yl]-2-butenoic acid
(3) (E,E)-3-[4-(2-diethylcarbamoyl-1-methylvinyl)-7-(3-ethoxycarbonylpropoxy)benzofuran-2-yl]-2-butenoic acid
(4) (E)-3-(2-acetyl-7-benzhydryloxybenzofuran-4-yl)-N,N-diethyl-2-butenamide
(5) (E)-3-[2-acetyl-7-(1-phenylethoxy)benzofuran-4-yl]-1-(4-phenylpiperazin-1-yl)-2-buten-1-one
(6) (E)-3-(2-acetyl-7-benzhydryloxybenzofuran-4-yl)-1-(4-phenylpiperazin-1-yl)-2-buten-1-one
(7) (E)-3-(2-acetyl-7-benzhydryloxybenzofuran-4-yl)-1-morpholino-2-buten-1-one
(8) (E)-3-[2-acetyl-7-(l-phenylethoxy)benzofuran-4-yl]-N-[2-(3,4-dimethoxyphenyl)ethyl]-2-butenamide
(9) (E)-3-[2-acetyl-7-(1-phenylethoxy)benzofuran-4-yl]-1-morpholino-2-buten-1-one
(10) (E)-3-[2-acetyl-7-(1-phenylethoxy)benzofuran-4-yl]-1-(4-benzylpiperazin-1-yl)-2-buten-1-one
(11) (E)-3-(2-acetyl-7-benzhydryloxybenzofuran-4-yl)-N-[2-,(3,4-dimethoxyphenyl)ethyl]-2-butenamide
(12) (E)-3-(2-acetyl-7-benzhydryloxybenzofuran-4-yl)-1-(4-benzylpiperazin-1-yl)-2-buten-1-one
(13) (E)-3-[2-acetyl-7-(2-benzo[1,3]dioxol-5-yloxoethoxy)benzofuran-4-yl]-N,N-diethyl-2-butenamide
(14) Ethyl (E)-4-[2-acetyl-4-(2-diethylcarbamoyl-1-methylvinyl)benzofuran-7-yloxy]butyrate
(15) Ethyl (E)-3-amino-5-(2-diethylcarbamoyl-1-methylvinyl)benzofurane-2-carboxylate
(16) Ethyl (E)-3-[3-(2-acetyl-3-aminobenzofuran-5-yl)-2-butenoylamino]-4-methoxybenzoate
(17) (E)-3-(2-acetyl-3-aminobenzofuran-5-yl)-N-[2-(3,4-dimethoxyphenyl)ethyl]-2-butenamide
(18) (E)-3-(2-acetyl-3-aminobenzofuran-5-yl)-1-(4-phenylpiperazin-1-yl)-2-buten-1-one
(19) (E)-3-(2-acetyl-3-aminobenzofuran-5-yl)-1-(4-benzylpiperazin-1-yl)-2-buten-1-one
(20) (E)-N-[2-acetyl-5-(1-methyl-3-morpholino-3-oxo-1-propenyl)benzofuran-3-yl]-2-(4-methoxyphenyl)acetamide
(21) (E)-3-{2-acetyl-3-[2-(4-methoxyphenyl)acetylamino]-benzofuran-5-yl}-N,N-diethyl-2-butenamide
(22) (E)-3-[3-amino-2-(4-cyanobenzoyl)benzofuran-5-yl]-N,N-diethyl-2-butenamide

(23) (E)-3-(2-acetyl-3-aminobenzofuran-5-yl)-1-morpholino-2-buten-1-one
(24) (E)-3-(2-benzoylbenzofuran-5-yl)-N-[2-(3,4-dimethoxyphenyl)ethyl]-2-butenamide
(25) (E)-3-(2-benzoylbenzofuran-5-yl)-1-morpholino-2-buten-1-one
(26) (E)-3-(2-acetylbenzofuran-5-yl)-N-[2-(3,4-dimethoxyphenyl)ethyl]-2-butenamide
(27) (E)-3-(2-acetylbenzofuran-5-yl)-1-morpholino-2-buten-1-one
(28) Ethyl (E)-4-{2-[2-(4-methoxyphenylcarbamoyl)-1-methylvinyl]benzofuran-7-yloxy}butyrate
(29) (E)-4-{2-[2-(3-methoxyphenylcarbamoyl)-1-methylvinyl]benzofuran-7-yloxy}butyric acid
(30) Ethyl (E)-4-[2-(1-methyl-3-morpholino-3-oxo-1-propenyl)benzofuran-7-yloxy]butyrate
(31) (E)-4-[4,6-dibromo-2-(2-diethylcarbamoyl-1-methylvinyl)benzofuran-7-yloxy]butyric acid
(32) Ethyl (E)-[2-(2-diethylcarbamoyl-1-methylvinyl)-4-ethylsulfamoylbenzofuran-7-yloxy]acetate
(33) (E)-3-(7-isopropoxybenzofuran-2-yl)-N,N-diethyl-2-butenamide
(34) (Z)-3-(7-isopropoxybenzofuran-2-yl)-N,N-diethyl-2-butenamide
(35) Ethyl (E)-4-[4-bromo-2-(2-diethylcarbamoyl-1-ethylvinyl)benzofuran-7-yloxy]butyrate
(36) (E)-4-[4-bromo-2-(2-diethylcarbamoyl-1-methylvinyl)benzofuran-7-yloxy]butyric acid
(37) (E)-3-(7-benzhydryloxybenzofuran-2-yl)-N,N-diethyl-2-butenamide
(38) (E)-3-(7-benzhydryloxybenzofuran-2-yl)-N-(3-methoxyphenyl)-2-butenamide
(39) (E)-3-[4-bromo-7-(2-dimethylaminoethoxy)benzofuran-2-yl]-N-(3-methoxyphenyl)-2-butenamide
(40) Ethyl (E)-4-{2-[2-(ethoxycarbonylmethylcarbamoyl)-1-methylvinyl]benzofuran-7-yloxy}butyrate
(41) (E)-3-(7-benzhydryloxybenzofuran-2-yl)-N-(4-methoxyphenyl)-2-butenamide
(42) (E)-3-(7-benzhydryloxybenzofuran-2-yl)-1-morpholino-2-buten-1-one
(43) (Z)-3-(7-benzhydryloxybenzofuran-2-yl)-N-(3,4-dimethoxyphenyl)-2-butenamide
(44) (E)-3-(7-benzhydryloxybenzofuran-2-yl)-1-morpholino-2-buten-1-one
(45) (E)-3-(7-benzhydryloxybenzofuran-2-yl)-N-(3,4-dimethoxyphenyl)-2-butenamide
(46) Ethyl (Z)-4-{2-[2-(3,4-dimethoxyphenylcarbamoyl)-1-methylvinyl]benzofuran-7-yloxy}butyrate
(47) (E)-3-(7-benzhydryloxybenzofuran-2-yl)-N-[2-(3,4-dimethoxyphenyl)ethyl]-2-butenamide
(48) Ethyl (Z)-4-[2-(2-diethylcarbamoyl-1-methylvinyl)-4-ethylsulfamoylbenzofuran-7-yloxy]butyrate
(49) Ethyl (E)-4-(2-{2-[2-(3,4-dimethoxyphenyl)ethylcarbamoyl]-1-methylvinyl}benzofuran-7-yloxy)butyrate
(50) 3-{7-(3-chloropropoxy)-4-[2-(3,4-dimethoxyphenyl)ethylsulfamoyl]benzofuran-2-yl}-N,N-diethyl-2-butenamide
(51) (E)-3-{7-(3-chloropropoxy)-4-[2-(3,4-dimethoxyphenyl)ethylsulfamoyl]benzofuran-2-yl}-N-(3-methoxyphenyl)-2-butenamide
(52) (Z)-3-{7-(3-chloropropoxy)-4-[2-(3,4-dimethoxyphenyl)ethylsulfamoyl]benzofuran-2-yl}-N-(3-methoxyphenyl)-2-butenamide
(53) (2E,4Z)-5-chloro-5-[7-(3-chloropropoxy)benzofuran-2-yl]penta-2,4-dienoic acid (3,4-dimethoxyphenyl)amide
(54) (2E,4Z)-5-(5-bromobenzofuran-2-yl)-5-chloropenta-2,4-dienoic acid (3-methoxyphenyl)amide
(55) (2E,4Z)-5-(5-bromobenzofuran-2-yl)-5-chloropenta-2,4-dienoic acid [2-(3,4-dimethoxyphenyl)ethyl]amide
(56) (2E,4Z)-5-chloro-5-(7-methoxybenzofuran-2-yl)-penta-2,4-dienoic acid [2-(3,4-dimethoxyphenyl)ethyl]amide
(57) (2E,4Z)-5-chloro-5-(7-methoxybenzofuran-2-yl)penta-2,4-dienoic acid (3-methoxyphenyl)amide
(58) (2E,4Z)-5-chloro-5-[7-(3-chloropropoxy)benzofuran-2-yl]penta-2,4-dienoic acid diethylamide
(59) (2E,4Z)-5-chloro-5-[7-(3-chloropropoxy)benzofuran-2-yl]-penta-2,4-dienoic acid diethylamide
(60) (2E,4Z)-5-chloro-5-[7-(3-chloropropoxy)benzofuran-2-yl]penta-2,4-dienoic acid [2-(3,4-dimethoxyphenyl)ethyl]amide
(61) (2E,4Z)-5-chloro-5-(7-methoxybenzofuran-2-yl)penta-2,4-dienenitrile
(62) Ethyl (2E,4Z)-5-chloro-5-(7-methoxybenzofuran-2-yl)penta-2,4-dienoate
(63) Ethyl (2E,4Z)-3-benzylsulfanyl-2-{5-chloro-5-[7-(3-chloropropoxy)benzofuran-2-yl]penta-2,4-dienoylamino}propionate
(64) Ethyl (2E,4Z)-3-benzylsulfanyl-2-[5-(5-bromobenzofuran-2-yl)-5-chloropenta-2,4-dienoylamino]propionate
(65) N-(2-acetyl-5-bromobenzofuran-3-yl)-5-methylisoxazole-4-carboxamide
(66) (Z)-N-(2-acetylbenzofuran-3-yl)-2-cyano-3-hydroxy-2-butenamide
(67) Ethyl 5-bromo-3-[(5-methylisoxazole-4-carbonyl)amino]benzofurane-2-carboxylate
(68) Ethyl 3-[(5-methylisoxazole-4-carbonyl)amino]benzofurane-2-carboxylate
(69) N-(2-acetylbenzofuran-3-yl)-5-methylisoxazole-4-carboxamide
(70) N-[5-bromo-2-(1-hydroxyethyl)benzofuran-3-yl]-5-methylisoxazole-4-carboxamide
(71) N-(2-acetyl-5-cyanobenzofuran-3-yl)-5-methylisoxazole-4-carboxamide
(72) (E)-N-(2-acetyl-5-(2-[2-(3,4-dimethoxyphenyl)ethylcarbamoyl]-1-methylvinyl)benzofuran-3-yl)-5-methylisoxazole-4-carboxamide
(73) N-[5-bromo-2-(4-cyanobenzoyl)benzofuran-3-yl]-5-methylisoxazole-4-carboxamide
(74) (E)-N-[2-acetyl-5-(2-diethylcarbamoyl-1-methylvinyl)benzofuran-3-yl]-5-methylisoxazole-4-carboxamide
(75) (E)-N-{2-acetyl-5-[1-methyl-3-oxo-3-(4-phenylpiperazin-1-yl)-1-propenyl]benzofuran-3-yl}-5-methylisoxazole-4-carboxamide
(76) 1-{3-[(5-methylisoxazole-4-carbonyl)amino]benzofuran-2-yl}ethyl acetate
(77) N-[5-bromo-2-(4-chlorobenzoyl)benzofuran-3-yl]-5-methylisoxazole-4-carboxamide
(78) N-[2-(4-bromobenzoyl)-7-methoxybenzofuran-3-yl]-5-methylisoxazole-4-carboxamide
(79) N-(2-carbamoylbenzofuran-3-yl)-5-methylisoxazole-4-carboxamide
(80) N-(2-acetyl-7-methoxybenzofuran-3-yl)-5-methylisoxazole-4-carboxamide
(81) (E)-N-[2-(4-cyanobenzoyl)-5-(1-methyl-3-morpholino-3-oxo-1-propenyl)benzofuran-3-yl]-5-methylisoxazole-4-carboxamide
(82) N-[2-(4-chlorobenzoyl)-7-methoxybenzofuran-3-yl]-5-methylisoxazole-4-carboxamide
(83) N-(2-acetyl-6-methoxybenzofuran-3-yl)-5-methylisoxazole-4-carboxamide
(84) (E)-N-[2-(4-{2-[2-(3,4-dimethoxyphenyl)ethylcarbamoyl]-1-methylvinyl}benzoyl)-7-methoxybenzofuran-3-yl]-5-methylisoxazole-4-carboxamide

(85) N-(5-bromo-2-cyanobenzofuran-3-yl)-5-methylisoxazole-4-carboxamide
(86) N-(2-cyanobenzofuran-3-yl)-5-methylisoxazole-4-carboxamide
(87) N-[2-(4-chlorobenzoyl)-7-methoxybenzofuran-3-yl]-5-methylisoxazole-4-carboxamide
(88) Ethyl 3-[(5-methylisoxazole-4-carbonyl)amino]benzofurane-2-carboxylate
(89) (E)-N-[2-(4-cyanobenzoyl)-5-(2-diethylcarbamoyl-1-methylvinyl)benzofuran-3-yl]-5-methylisoxazole-4-carboxamide
(90) (E)-N-(2-(4-cyanobenzoyl)-5-{2-[2-(3,4-dimethoxyphenyl)ethylcarbamoyl]-1-methylvinyl}benzofuran-3-yl)-5-methylisoxazole-4-carboxamide
(91) Ethyl (E)-5-(2-diethylcarbamoyl-1-methylvinyl)-3-[(5-methylisoxazole-4-carbonyl)amino]benzofurane-2-carboxylate
(92) (Z)-3-(2-cyano-3-hydroxy-2-butenoylamino)benzofurane-2-carboxylic acid
(93) (Z)-N-(2-acetyl-5-cyanobenzofuran-3-yl)-2-cyano-3-hydroxy-2-butenamide
(94) N-{2-acetyl-5-[(E)-2-diethylcarbamoyl-1-methylvinyl]benzofuran-3-yl}-2-cyano-3-hydroxy-(Z)-2-butenamide
(95) N-{2-acetyl-5-[1-methyl-3-oxo-3-(4-phenylpiperazin-1-yl)-(E)-1-propenyl]benzofuran-3-yl}-2-cyano-3-hydroxy-(Z)-2-butenamide
(96) (Z)-N-(2-acetyl-5-bromobenzofuran-3-yl)-2-cyano-3-hydroxy-2-butenamide
(97) Ethyl (Z)-5-bromo-3-(2-cyano-3-hydroxy-2-butenoylamino)benzofurane-2-carboxylate
(98) (Z)-N-[5-bromo-2-(4-chlorobenzoyl)benzofuran-3-yl]-2-cyano-3-hydroxy-2-butenamide
(99) (Z)-N-[2-(4-bromobenzoyl)-7-methoxybenzofuran-3-yl]-2-cyano-3-hydroxy-2-butenamide
(100) (Z)-N-[5-bromo-2-(4-cyanobenzoyl)benzofuran-3-yl]-2-cyano-3-hydroxy-2-butenamide
(101) (Z)-3-(2-cyano-3-hydroxy-2-butenoylamino)benzofurane-2-carboxamide
(102) (Z)-N-(2-acetyl-7-methoxybenzofuran-3-yl)-2-cyano-3-hydroxy-2-butenamide
(103) N-(2-acetyl-5-{(E)-2-[2-(3,4-dimethoxyphenyl)ethylcarbamoyl]-1-methylvinyl}benzofuran-3-yl)-2-cyano-3-hydroxy-(Z)-2-butenamide
(104) (Z)-N-(5-bromo-2-cyanobenzofuran-3-yl)-2-cyano-3-hydroxy-2-butenamide
(105) (Z)-N-(2-cyanobenzofuran-3-yl)-2-cyano-3-hydroxy-2-butenamide
(106) N-[2-(4-{(E)-2-[2-(3,4-dimethoxyphenyl)ethylcarbamoyl]-1-methylvinyl}benzoyl)-7-methoxybenzofuran-3-yl]-2-cyano-3-hydroxy-(Z)-2-butenamide
(107) Ethyl (Z)-3-(2-cyano-3-hydroxy-2-butenoylamino)benzofurane-2-carboxylate
(108) N-[2-acetyl-5-(1-methyl-3-morpholino-3-oxo-(E)-1-propenyl)benzofuran-3-yl]-2-cyano-3-hydroxy-(Z)-2-butenamide
(109) N-[2-(4-cyanobenzoyl)-5-((E)-2-diethylcarbamoyl-1-methylvinyl)benzofuran-3-yl]-2-cyano-3-hydroxy-(Z)-2-butenamide
(110) (Z)-N-(2-acetyl-7-methoxybenzofuran-3-yl)-2-cyano-3-hydroxy-2-butenamide
(111) N-(2-acetyl-7-methoxybenzofuran-4-yl)-5-methylisoxazole-4-carboxamide
(112) (Z)-N-(2-acetyl-7-methoxybenzofuran-4-yl)-2-cyano-3-hydroxy-2-butenamide
(113) (E)-N-[5-bromo-2-(4-chlorobenzoyl)benzofuran-3-yl]-3-phenylacrylamide
(114) (E)-N-(2-acetyl-5-bromobenzofuran-3-yl)-3-phenylacrylamide
(115) (E)-N-[5-bromo-2-(4-chlorobenzoyl)benzofuran-3-yl]-2-butenamide
(116) (E)-N-(2-acetyl-6-methoxybenzofuran-3-yl)-2-butenamide
(117) (E)-N-(5-bromo-2-cyanobenzofuran-3-yl)-2-butenamide
(118) Ethyl (E)-3-methyl-acryloylaminobenzofurane-2-carboxylate
(119) Ethyl (E)-3-(3-phenylacryloylamino)benzofurane-2-carboxylate
(120) (E)-N-(2-acetyl-6-methoxybenzofuran-3-yl)-3-phenylacrylamide
(121) (E)-3-(3-phenylacryloylamino)benzofurane-2-carboxylic acid
(122) (E)-N-(5-bromo-2-cyanobenzofuran-3-yl)-3-phenylacrylamide
(123) (E)-N-(2-acetyl-5-bromobenzofuran-3-yl)-2-butenamide
(124) Methyl (2-{1-[(5-methylisoxazole-4-carbonyl)amino]ethyl}benzofuran-7-yloxy)acetate
(125) Ethyl 4-(4-ethylsulfamoyl-2-{1-[(5-methylisoxazole-4-carbonyl)amino]ethyl}benzofuran-7-yloxy)butyrate
(126) (Z)-4-{2-[1-(2-cyano-3-hydroxy-2-butenoylamino)ethyl]benzofuran-7-yloxy}butyric acid
(127) (E)-{2-[1-(2-cyano-3-hydroxy-2-butenoylamino)ethyl]benzofuran-7-yloxy}acetic acid
(128) Ethyl (E)-4-{2-[1-(2-cyano-3-hydroxy-2-butenoylamino)ethyl]-4-ethylsulfamoylbenzofuran-7-yloxy}butyrate
(129) (E)-4-{2-[1-(2-cyano-3-hydroxy-2-butenoylamino)ethyl]-4-ethylsulfamoylbenzofuran-7-yloxy}butyric acid
(130) (E)-[1-(7-methoxybenzofuran-2-yl)ethyl]-2-butenamide p0 (131) (E)-N-{1-[7-(3-chloropropoxy)benzofuran-2-yl]ethyl}-3-phenylacrylamide
(132) (E)-N-[1-(7-methoxybenzofuran-2-yl)ethyl]-3-phenylacrylamide
(133) (E)-N-{1-[7-(3-chloropropoxy)benzofuran-2-yl]ethyl}-2-butenamide
(134) (E)-3-(2-acetylbenzofuran-5-yl)-2-butenoic acid
(135) (2E,4Z)-5-(2-butylbenzofuran-3-yl)-5-chloropenta-2,4-dienoic acid (4-methoxyphenyl)amide
(136) (E,E)-3-[5-(1-methyl-3-morpholin-4-yl-3-oxopropenyl)benzofuran-2-yl]-2-butenoic acid
(137) (E)-3-[2-acetyl-7-(3-chloropropoxy)benzofuran-4-yl]-2-butenoic acid diethylamide
(138) (2E,4Z)-5-chloro-5-(7-methoxybenzofuran-2-yl)-1-morpholin-4-ylpenta-2,4-dien-1-one
(139) (E)-3-{2-acetyl-7-(3-(4-chlorophenylsulfanyl)propoxy)benzofuran-4-yl}-2-butenoic acid diethylamide
(140) Ethyl 4-[2-(1-chloro-3-oxopropenyl)benzofuran-7-yloxy]-butyrate
(141) (E)-3-[3-(4-chlorophenyl)-5-methoxybenzofuran-2-yl]-N-(4-methoxyphenyl)acrylamide
(142) (2E,4Z)-5-chloro-5-(7-methoxybenzofuran-2-yl)penta-2,4-dienoic acid diisopropylamide
(143) (E)-3-[7-chloro-3-(4-chlorophenyl)benzofuran-2-yl]-2-butenoic acid (4-methoxyphenyl)-amide
(144) (2E,4Z)-5-chloro-5-(7-methoxybenzofuran-2-yl)-1-piperidin-1-ylpenta-2,4-dien-1-one
(145) Ethyl 4-[2-(1-chloro-5-morpholin-4-yl-5-oxo-penta-(1Z,3E)-1,3-dienyl)benzofuran-7-yloxy]butyrate
(146) Ethyl 3-[2-(1-chloro-3-oxo-(Z)-propenyl)benzofuran-5-yl]-(E)-2-butenoate
(147) (2E,4Z)-4-[2-(1-chloro-5-morpholin-4-yl-5-oxopenta-1,3-dienyl)benzofuran-7-yloxy]butyric acid (148) Ethyl 3-[2-(1-chloro-5-morpholin-4-yl-5-oxo-penta-(1Z,3E)-1,3-dienyl)benzofuran-5-yl]-(E)-2-butenoate
(149) (E)-3-(2-butylbenzofuran-3-yl)-2-methyl-1-morpholin-4-ylpropenone
(151) (Z)-3-(5-bromo-2-methylbenzofuran-3-yl)-3-chloropropenal
(152) (E)-3-(5-bromo-3-methylbenzofuran-2-yl)-2-butenoic acid diethylamide
(153) (Z)-3-(5-bromo-3-methylbenzofuran-2-yl)-2-butenoic acid diethylamide
(154) (2E,4Z)-5-(5-bromobenzofuran-2-yl)-5-chloropenta-2,4-dienenitrile
(155) (E)-3-(2-butylbenzofuran-3-yl)-2-butenoic acid diethylamide
(157) (E)-3-(2-butylbenzofuran-3-yl)-2-butenoic acid [2-(3,4-dimethoxyphenyl)ethyl]amide
(158) (E)-3-amino-5-(2-diethylcarbamoyl-1-methylvinyl)benzofurane-2-carboxylic acid (3-methoxyphenyl)amide
(159) Ethyl (2E,4Z)-5-(5-bromobenzofuran-2-yl)-5-chloro-penta-2,4-dienoate
(160) (E)-3-[7-(1-phenylethoxy)benzofuran-2-yl]-2-butenoic acid (3-methoxyphenyl)amide
(161) (Z)-3-[7-(1-phenylethoxy)benzofuran-2-yl]-2-butenoic acid (3-methoxyphenyl)amide
(162) (E)-1-morpholin-4-yl-3-[7-(1-phenylethoxy)benzofuran-2-yl]-2-buten-1-one
(163) (Z)-1-morpholin-4-yl-3-[7-(1-phenylethoxy)benzofuran-2-yl]-2-buten-1-one
(164) (E)-3-[7-(1-phenylethoxy)benzofuran-2-yl]-2-butenoic acid [2-(3,4-dimethoxyphenyl)ethyl]amide
(165) (Z)-3-[7-(1-phenylethoxy)benzofuran-2-yl]-2-butenoic acid [2-(3,4-dimethoxyphenyl)ethyl]amide
(166) (E)-3-(3-ethylbenzofuran-2-yl)-1-morpholin-4-yl-2-buten-1-one
(167) 3-(3-ethylbenzofuran-2-yl)-2-butenoic acid [2-(3,4-dimethoxyphenyl)ethyl]amide
(169) 3-(5-bromo-2-methylbenzofuran-3-yl)-2-butenoic acid diethylamide
(170) (E)-3-(2-acetyl-5-chloro-benzofuran-7-yl)-2-butenoic acid diethylamide
(171) (E)-1-(4-benzylpiperazin-1-yl)-3-(2-butylbenzofuran-3-yl)-2-buten-1-one
(172) (E)-3-[7-(1-phenylethoxy)benzofuran-2-yl]-2-butenoic acid (4-methoxyphenyl)amide
(173) (E)-5-methylisoxazole-4-carboxylic acid [5-bromo-2-(3-phenylacryloyl)benzofuran-3-yl]amide
(174) 2-cyano-3-hydroxy-(Z)-2-butenoic acid [5-bromo-2-((E)-3-phenylacryloyl)benzofuran-3-yl]amide
(175) (E)-5-phenyl-2-pentenoic acid (2-acetyl-5-bromobenzofuran-3-yl)amide
(176) (E,E)-N-[5-bromo-2-(3-dimethylaminoacryloyl)-benzofuran-3-yl]-3-phenylacrylamide
(177) (E)-2-butenoic acid [5-bromo-2-(3-dimethylamino-(E)-acryloyl)benzofuran-3-yl]amide
(178) (E)-N-(2-acetyl-5-bromobenzofuran-3-yl)-3-(4-methoxyphenyl)acrylamide
(179) (E)-N-[2-(4-bromobenzoyl)-7-methoxybenzofuran-3-yl]-3-phenylacrylamide
(180) (E)-N-(5-bromo-2-chlorobenzofuran-3-yl)-3-phenylacrylamide
(181) (E)-N-(2-chloro-7-methoxybenzofuran-3-yl)-3-phenylacrylamide
(182) (E)-N-(2-acetyl-7-methoxybenzofuran-3-yl)-3-phenylacrylamide
(183) 5-methyl-isoxazole-4-carboxylic acid [5-bromo-2-(3-methoxyphenylcarbamoyl)benzofuran-3-yl]amide
(184) (E)-2-butenoic acid (5-bromo-2-chlorobenzofuran-3-yl)amide
(185) (E)-2-butenoic acid (2-acetyl-7-methoxybenzofuran-3-yl)amide
(186) (E)-5-methyl-isoxazole-4-carboxylic acid [5-((E)-2-diethylcarbamoyl-1-methylvinyl)-2-(3-methoxyphenylcarbamoyl)benzofuran-3-yl]amide
(187) (E)-2-butenoic acid (2-chloro-7-methoxybenzofuran-3-yl)amide
(188) (Z)-5-bromo-3-(2-cyano-3-hydroxy-2-butenoylamino)benzofurane-2-carboxylic acid (3-methoxyphenyl)amide
(189) 3-(2-cyano-3-hydroxy-(Z)-2-butenoylamino)-5-((E)-2-diethylcarbamoyl-1-methylvinyl)-benzofurane-2-carboxylic acid(3-methoxyphenyl)amide
(190) N-(1-benzofuran-2-ylethyl)acetamide
(191) N-[1-(7-methoxybenzofuran-2-yl)ethyl]acetamide
(192) (E)-2-butenoic acid (1-(benzofuran-2-yl)ethyl)amide
(193) N-(2-acetyl-5-bromobenzofuran-3-yl)-2-cyanoacetamide
(194) (E)-N-[5-bromo-2-(3-dimethylaminoacryloyl)benzofuran-3-yl]acetamide
(195) (E)-N-{5-bromo-2-[3-(4-methoxyphenyl)-acryloyl]benzofuran-3-yl}-3-chloropropionamide
(196) (E)-2-benzylamino-N-{5-bromo-2-[3-(4-methoxyphenyl)acryloyl]benzofuran-3-yl}acetamide
(197) N-[5-bromo-2-(4-chlorobenzoyl)benzofuran-3-yl]-2-cyanoacetamide
(198) N-[2-(4-bromobenzoyl)-7-methoxybenzofuran-3-yl]-2-cyanoacetamide
(199) Ethyl N-(2-acetyl-5-bromobenzofuran-3-yl)oxamic acid
(200) N-(5-bromo-2-chlorobenzofuran-3-yl)-4-methoxybenzamide
(201) (E)-N-[5-bromo-2-(3-phenylacryloyl)-benzofuran-3-yl]-3-chloropropionamide
(202) N-[1-(3-acetylbenzofuran-2-yl)ethyl]acetamide
(203) (E)-3-benzylamino-N-{5-bromo-2-[3-(4-methoxyphenyl)acryloyl]benzofuran-3-yl}propionamide
(204) N-(2-acetyl-7-methoxybenzofuran-3-yl)-3-chloropropionamide
(205) N-(2-acetyl-7-methoxybenzofuran-3-yl)-2-chloroacetamide
(207) Ethyl N-[5-bromo-2-(4-chlorobenzoyl)-benzofuran-3-yl]oxamic acid
(208) N-(2-acetyl-7-methoxybenzofuran-3-yl)acetamide
(209) N-(2-acetyl-5-bromobenzofuran-3-yl)-2-ethoxybenzamide
(210) N-(2-acetyl-5-bromobenzofuran-3-yl)-3,4,5-trimethoxybenzamide
(211) N-(2-acetyl-4-bromo-7-methoxybenzofuran-3-yl)acetamide
(212) 4-(5-bromobenzofuran-2-yl)-2-phenylthiazole
(213) 4-[7-chloro-3-(4-chlorophenyl)benzofuran-2-yl]-2-phenylthiazole (214) 4-[7-chloro-3-(4-chlorophenyl)benzofuran-2-yl]-2-methylthiazole
(215) 4-[3-(4-chlorophenyl)-5-methoxybenzofuran-2-yl]-2-phenylthiazole
(216) 4-(5-bromobenzofuran-2-yl)-2-methylthiazole
(217) 4-[3-(4-chlorophenyl)-5-methoxybenzofuran-2-yl]-2-methylthiazole
(218) 4-[3-(4-chlorophenyl)-5-methoxybenzofuran-2-yl]thiazol-2-ylamine
(219) N'-{4-[3-(4-chlorophenyl)-5-methoxybenzofuran-2-yl]thiazol-2-yl}-N,N-dimethylformamidine
(220) 5-methylisoxazole-4-carboxylic acid {4-[3-(4-chlorophenyl)-5-methoxybenzofuran-2-yl]thiazol-2-yl}amide
(221) N'-{4-[3-(4-chlorophenyl)-5-methoxybenzofuran-2-yl]-5-formylthiazol-2-yl}-N,N-dimethylformamidine
(222) (Z)-2-cyano-3-hydroxy-2-butenoic acid {4-[3-(4-chlorophenyl)-5-methoxybenzofuran-2-yl]thiazol-2-yl}amide
(223) N'-{4-[3-(4-chlorophenyl)-5-methoxybenzofuran-2-yl]-5-[(2-hydroxyethylimino)methyl]thiazol-2-yl}-N,N-dimethylformamidine
(224) Ethyl (E)-4-[2-(2-diethylcarbamoyl-1-methylvinyl)benzofuran-7-yloxy]butyrate
(225) Ethyl (Z)-4-[2-(2-diethylcarbamoyl-1-methylvinyl)benzofuran-7-yloxy]butyrate
(226) 3-chloro-3-(7-methoxy-benzofuran-2-yl)-propenal
(227) Ethyl 4-{2-[2-(3,4-dimethoxyphenylcarbamoyl)-1-methylvinyl]benzofuran-7-yloxy}butyrate and pharmaceutically acceptable salts of these.

When substituent Z in the formula (I) is $Z^a$, stereoisomers (cis form and trans form or Z form and E form) are present in the double bond moiety, all of which isomers are encompassed in the present invention.

In addition, when stereoisomers (cis form and trans form or Z form and E form) are present in the double bond moiety the compound of the present invention, all of such isomers are encompassed in the present invention, unless otherwise specified.

The benzofuran compound of the present invention represented by the formula (I) (benzofuran compound (I)) may form a pharmaceutically acceptable salt. When benzofuran compound (I) has a basic group, it can form an acid addition salt. The acid to form such acid addition salt is not particularly limited as long as it can form a salt with a basic moiety and is pharmaceutically acceptable. As such acid, inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, toluenesulfonic acid and the like can be mentioned.

When the benzofuran compound (I) has an acidic group such as carboxyl group and the like, it can form, for example, alkali metal salts (e.g., sodium salt, potassium salt and the like), alkaline earth metal salts (e.g., calcium salt, magnesium salt and the like) or organic base salts (e.g., triethylamine salt, dicyclohexylamine salt, pyridine salt, tert-butylamine salt and the like).

The benzofuran compound (I) of the present invention and a pharmaceutically acceptable salt thereof can be produced from a compound of the formula (II) (compound (II)) and the like by any of the following production methods or a method analogous thereto.

(Production Method 1)

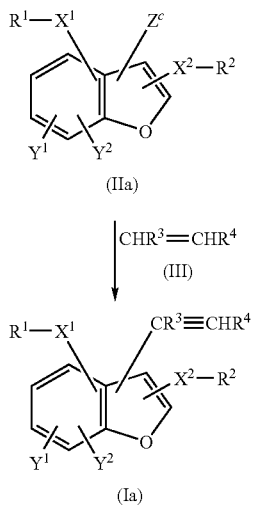

wherein $R^1$, $R^2$, $R^3$, $R^4$, $X^1$, $X^2$, $Y^1$ and $Y^2$ are as defined in the aforementioned (1), and $Z^c$ is a halogen atom (a fluorine atom, a chlorine atom, a bromine atom or an iodine atom etc.).

Production Method 1 is a method to produce a compound of the formula (Ia) (compound (Ia)), which is a compound of the formula (I), wherein Z is $Z^a$ and $X^3$ is a bond, by reacting a compound of the formula (IIa) (compound (IIa)), which is a compound of the formula (II), wherein $Z^c$ is a halogen atom, with a compound of the formula (III) (compound (III)).

This production method is generally performed by subjecting the compounds to a reaction exemplified by the Heck reaction (Organic Reactions, vol. 27, p. 345 (1982)). The reaction is generally carried out in a solvent in the presence of a palladium catalyst.

The solvent to be used in Production Method 1 is not particularly limited as long as it does not inhibit the reaction and, for example, triethylamine, acetonitrile, dimethylformamide (DMF) and the like; a mixture thereof and the like can be mentioned.

While the amount of compound (III) to be used in Production Method 1 is not particularly limited, it is generally 1-5 mol, preferably 1-3 mol, per 1 mol of compound (IIa).

As the palladium catalyst in Production Method 1, for example, palladium acetate, palladium carbon, palladium alumina, palladium zeolite, palladium silica, oxidized palladium and the like can be mentioned. The amount of the catalyst to be used is generally 0.001-0.5 mol, preferably 0.001-0.1 mol, per 1 mol of compound (IIa).

In Production Method 1, a phosphine ligand may also be added to maintain catalyst activity. As the phosphine ligand, for example, tri-o-tolylphosphine and the like can be mentioned. The amount of the phosphine ligand to be used is generally 1-5 mol, preferably 1-3 mol, per 1 mol of the palladium catalyst.

While the reaction conditions in Production Method 1, such as reaction temperature, reaction time and the like, vary depending on the reaction reagent, reaction solvent and the like to be used, −30-150° C., 30 min-24 hr are generally employed. Where necessary, a sealed tube may be used to carry out the reaction in a closed system.

The compound (IIa) can be produced by any of the following methods.

(Production Method a-1)

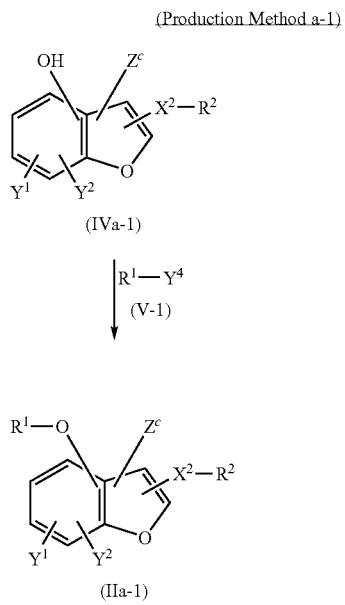

wherein $R^2$, $X^2$, $Y^1$ and $Y^2$ are as defined in the aforementioned (1), $R^1$ is a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group) and $C_{6-14}$ aryl group (the aryl group is optionally substituted by one or more substituents selected from the group consisting of hydroxyl group and $C_{1-6}$ alkoxy group)], and $Y^4$ and $Z^c$ are each a halogen atom (a fluorine atom, a chlorine atom, a bromine atom, an iodine atom etc.).

Production Method a-1 is a method to produce a compound of the formula (IIa-1) (compound (IIa-1)), which is a compound of the formula (IIa), wherein $X^1$ is an oxygen atom, by reacting a compound of the formula (IVa-1) (compound (IVa-1)) with a compound of the formula (V-1) (compound (V-1)). The reaction of Production Method a-1 is generally performed in a solvent in the presence of a base.

The solvent to be used in Production Method a-1 is not particularly limited as long as it does not inhibit the reaction and, for example, acetone, dioxane, acetonitrile, tetrahydrofuran, chloroform, methylene chloride,.ethylene chloride, benzene, toluene, xylene, ethyl acetate, N,N-dimethylformamide, dimethyl sulfoxide and the like; a mixture thereof and the like can be mentioned.

The base to be used in Production Method a-1 is not particularly limited, inorganic bases such as alkali metal carbonate salts (e.g., sodium carbonate, sodium hydrogen carbonate, potassium carbonate, potassium hydrogen carbonate and the like), alkali metal hydroxide salts (e.g., sodium hydroxide, potassium hydroxide and the like), metal hydride compounds (e.g., sodium hydride, potassium hydride, calcium hydride and the like) and the like; organic bases such as alkali metal alkoxides (e.g., sodium methoxide, sodium ethoxide, potassium-t-butoxide and the like), amines (e.g., triethylamine, diisopropylethylamine and the like) and the like can be mentioned.

While the amount of compound (V-1) to be used in Production Method a-1 is not particularly limited, it is generally 1-5 mol, preferably 1-3 mol, per 1 mol of compound (IVa-1).

While the reaction conditions in Production Method a-1 such as reaction temperature, reaction time and the like vary depending on the reaction reagent, reaction solvent and the like to be used, −30-150° C., 30 min-24 hr are generally employed.

(Production Method a-2)

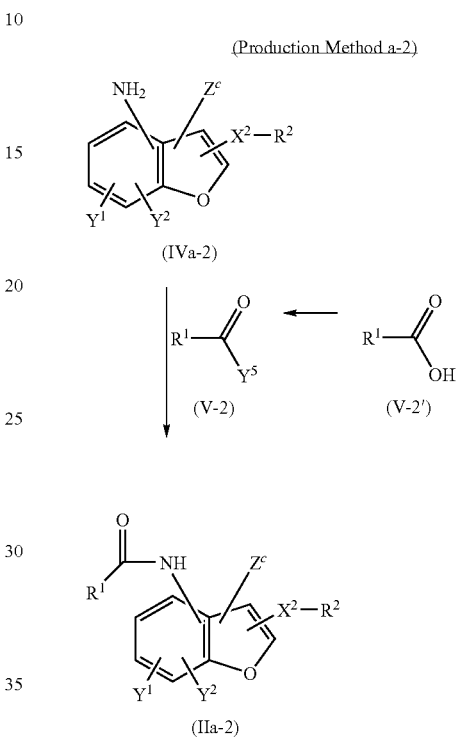

wherein $R^2$, $X^2$, $Y^1$ and $Y^2$ are as defined in the aforementioned (1), $R^1$ is a $C_{6-14}$ aryl group (the aryl group is optionally substituted by one or more substituents selected from the group consisting of hydroxyl group and $C_{1-6}$ alkoxy group) or a $C_{1-6}$ alkyl group [the alkyl group is optionally substituted by one or more substituents selected from the group consisting of halogen atom, —COOAlk, amino group (the amino group is optionally mono- or di-substituted by $C_{1-6}$ alkyl group) and $C_{6-14}$ aryl group (the aryl group is optionally substituted by one or more substituents selected from the group consisting of hydroxyl group and $C_{1-6}$ alkoxy group)], and $Y^5$ and $Z^c$ are each a halogen atom (a fluorine atom, a chlorine atom, a bromine atom, an iodine atom etc.).

Production Method a-2 is a method to produce a compound of the formula (IIa-2) (compound (IIa-2)), which is a compound of the formula (IIa), wherein $X^1$ is

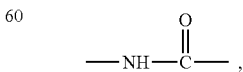

by reacting a compound of the formula (IVa-2) (compound (IVa-2)) with a compound of the formula (V-2) (compound (V-2).

In Production Method a-2, compound (V-2), which is an acid halide, is first produced from compound (V-2') by a conventional method. The reagent to be used for the preparation of the acid halide is not particularly limited and, for example, thionyl chloride, phosphorus pentachloride, phosphorus trichloride and the like can be mentioned. While the amount of the reagent to be used is not particularly limited, it is generally 1-30 mol, preferably 1-15 mol, per 1 mol of compound (V-2). While the reaction conditions for acid halide preparation such as reaction temperature, reaction time and the like vary depending on the reaction reagent to be used, −30-150° C., 30 min-12 hr are generally employed. Excess reagent is removed by evaporation and the like.

Then, compound (V-2) and compound (IVa-2) are reacted. The reaction is generally carried out in a solvent. The solvent to be used for the reaction is not particularly limited as long as it does not inhibit the reaction and, for example, acetone, dioxane, acetonitrile, tetrahydrofuran, chloroform, methylene chloride, ethylene chloride, benzene, toluene, xylene, ethyl acetate, N,N-dimethylformamide, dimethyl sulfoxide and the like; a mixture thereof and the like can be mentioned.

While the amount of compound (V-2) to be used in the reaction is not particularly limited, it is generally 1-5 mol, preferably 1-3 mol, per 1 mol of compound (IVa-2).

While the reaction conditions in this reaction such as reaction temperature, reaction time and the like vary depending on the reaction reagent, reaction solvent and the like to be used, −30-150° C, 30 min-24 hr are generally employed.

The compound (IVa-1) can be produced by the method shown in Production Method b.

(Production Method b)

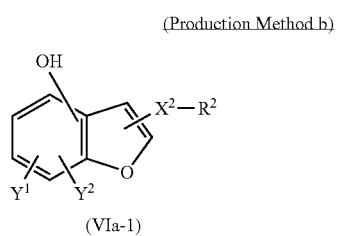

(VIa-1)

↓

(IVa-1)

wherein $R^2$, $X^2$, $Y^1$ and $Y^2$ are as defined in the aforementioned (1), and $Z^c$ is a halogen atom (a fluorine atom, a chlorine atom, a bromine atom, an iodine atom etc.).

In Production Method b, compound (IVa-1) can be produced by halogenizing the benzofuran ring of compound (VIa-1) at a substitutable position by a method known per se.

The compound (IVa-2) can also be produced according to Production Method b.

(Production Method 2)

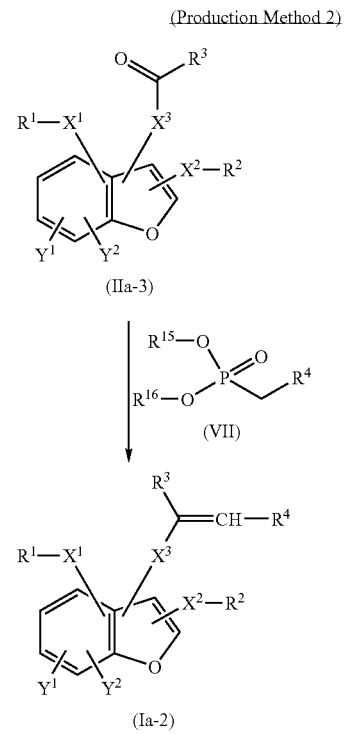

(Ia-2)

wherein $R^1$, $R^2$ $R^3$, $R^4$, $X^1$, $X^2$, $X^3$, Y and $Y^2$ are as defined in the aforementioned (1), and $R^{15}$ and $R^{16}$ are the same or different and each is a $C_{1-6}$ alkyl group, a $C_{6-14}$ aryl group and the like.

Production Method 2 is a method to produce a compound of the formula (Ia-2) (compound (Ia-2)), which is a compound of the formula (I), wherein Z is $Z^a$, by reacting a compound of the formula (IIa-3) (compound (IIa-3)), which is a compound of the formula (II), wherein $Z^c$ is

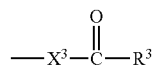

with a compound of the formula (VII) (compound (VII)).

This production method can be generally performed by subjecting to a reaction exemplified by the Wittig-Horner-Emmons reaction (Chemistry Review, vol. 74, p. 87 (1974)). The reaction is generally carried out in a solvent.

The solvent to be used in Production Method 2 is not particularly limited as long as it does not inhibit the reaction and, for example, dioxane, acetonitrile, tetrahydrofuran, chloroform, methylene chloride, ethylene chloride, benzene, toluene, xylene, ethyl acetate, dimethyl sulfoxide and the like; a mixture thereof and the like can be mentioned.

While the amount of compound (VII) to be used in Production Method 2 is not particularly limited, it is generally 1-5 mol, preferably 1-3 mol, per 1 mol of compound (IIa-3).

While the reaction conditions in Production Method 2 such as reaction temperature, reaction time and the like vary depending on the reaction reagent, reaction solvent and the like to be used, −30-150° C., 30 min-24 hr are generally employed.

The compound (IIa-3) can be produced according to (Production Method a-1) or (Production Method a-2) in (Production Method 1).

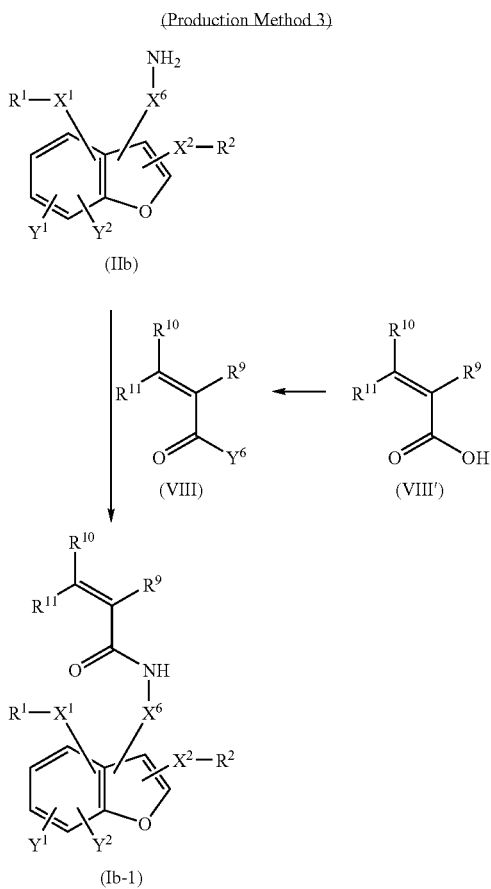

wherein $R^1$, $R^2$, $R^9$, $R^{10}$, $R^{11}$, $X^1$, $X^2$, $X^6$, $Y^1$ and $Y^2$ are as defined in the aforementioned (1), and $Y^6$ is a halogen atom (a fluorine atom, a chlorine atom, a bromine atom, an iodine atom etc.).

Production Method 3 is a method to produce a compound of the formula (Ib-1) (compound (Ib-1)), which is a compound of the formula (I), wherein Z is $Z^b$, by reacting a compound of the formula (IIb) (compound (IIb)), which is a compound of the formula (II), wherein $Z^c$ is —$X^6$—$NH_2$, with a compound of the formula (VIII) (compound (VIII)).

In Production Method 3, compound (VIII), which is an acid halide, is first produced from compound (VIII') by a conventional method. The reagent to be used for the preparation of the acid halide is not particularly limited and, for example, thionyl chloride, phosphorus pentachloride, phosphorus trichloride and the like can be mentioned. While the amount of the reagent to be used is not particularly limited, it is generally 1-30 mol, preferably 1-15 mol, per 1 mol of compound (VIII'). While the reaction conditions for acid halide preparation such as reaction temperature, reaction time and the like vary depending on the reaction reagent to be used, −30-150° C., 30 min-12 hr are generally employed. Excess reagent is removed by evaporation and the like.

Then, compound (VIII) and compound (IIb) are reacted. The reaction is generally carried out in a solvent. The solvent to be used for the reaction is not particularly limited as long as it does not inhibit the reaction and, for example, acetone, dioxane, acetonitrile, tetrahydrofuran, chloroform, methylene chloride, ethylene chloride, benzene, toluene, xylene, ethyl acetate, N,N-dimethylformamide, dimethyl sulfoxide and the like; a mixture thereof and the like can be mentioned.

While the amount of compound (VIII) to be used in the reaction is not particularly limited, it is generally 1-5 mol, preferably 1-3 mol, per 1 mol of compound (IIb).

While the reaction conditions of this reaction such as reaction temperature, reaction time and the like vary depending on the reaction reagent, reaction solvent and the like to be used, −30-150° C., 30 min-24 hr are generally employed.

The compound (IIb) can be produced according to (Production Method a-1) or (Production Method a-2) in (Production Method 1).

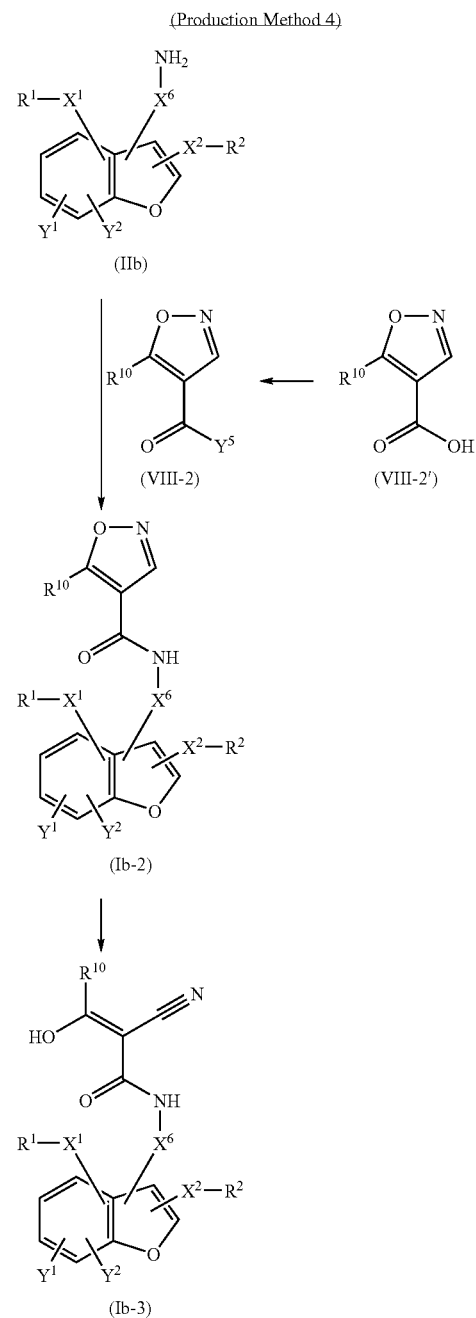

wherein $R^1$, $R^2$, $R^{10}$, $X^1$, $X^2$, $X^6$, $Y^1$ and $Y^2$ are as defined in the aforementioned (1), and $Y^5$ is as defined in Production Method 3.

Production Method 4 is a method to produce a compound of the formula (Ib-3) (compound (Ib-3)) by first reacting compound (IIb) with a compound of the formula (VIII-2) (compound (VIII-2)) by a method according to Production Method 3 to give a compound of the formula (Ib-2) (compound (Ib-2)), and hydrolyzing compound (Ib-2).

In the hydrolysis in Production Method 4, compound (Ib-2) is reacted in a solvent in the presence of a base.

The solvent to be used for the hydrolysis in lo Production Method 4 is not particularly limited as long as it does not inhibit the reaction and, for example, acetone, dioxane, acetonitrile, tetrahydrofuran, chloroform, methylene chloride, ethylene chloride, benzene, toluene, xylene, ethyl acetate, N,N-dimethylformamide, dimethyl sulfoxide and the like; a mixture thereof and the like can be mentioned.

As the base to be used for the hydrolysis in Production Method 4, organic bases such as amines (e.g., triethylamine, diisopropylethylamine and the like) and the like can be mentioned.

While the amount of the base to be used for the hydrolysis in Production Method 4 is not particularly limited, it is generally 1-30 mol, preferably 1-15 mol, per 1 mol of compound (Ib-2).

While the reaction conditions of hydrolysis in Production Method 4 such as reaction temperature, reaction time and the like vary depending on the reaction reagent, reaction solvent and the like to be used, −30-150° C., 30 min-24 hr are generally employed.

The benzofuran compound (I) obtained in the above-mentioned Production Method 1-4 can be isolated by a conventional method and purified as necessary by, for example, recrystallization, preparative thin layer chromatography, column chromatography and the like.

The benzofuran compound (I) can be converted to a pharmaceutically acceptable salt thereof by a method known per se.

A pharmaceutical composition comprising the benzofuran compound of the present invention (I) or a pharmaceutically acceptable salt thereof can contain additive and the like. As the additive, for example, excipients (e.g., starch, gum arabic, carboxymethylcellulose, hydroxypropylcellulose, crystalline cellulose and the like), lubricants (e.g., magnesium stearate, talc and the like), disintegrants (e.g., carboxymethylcellulose calcium, talc and the like) and the like can be mentioned.

After mixing with the above-mentioned various components, the mixture can be processed to give, for example, a preparation for oral administration such as capsule, tablet, fine granules, granules, dry syrup and the like or a preparation for parenteral administration such as injection, suppository and the like by a method known per se.

While the dose of the benzofuran compound (I) or a pharmaceutically acceptable salt thereof varies depending on the subject of administration, condition and other factors, a dose of about 0.01-500 mg is administered 1-3 times a day for oral administration to an adult patients with, for example, allergy, asthma or inflammation.

The benzofuran compound of the present invention (I) and a pharmaceutically acceptable salt thereof show superior leukotriene inhibitory action, BLT2 competitive inhibitory action, BLT2 blocking action, action for the prophylaxis or treatment of allergy, action for the prophylaxis or treatment of asthma, and action for the prophylaxis or treatment of inflammation for mammals (human, horse, bovine, dog, cat, rat, mouse, hamster and the like), and are useful for the prophylaxis or treatment-of allergic diseases (e.g., allergic dermatitis, allergic rhinitis and the like), atopic dermatitis, asthma, chronic obstructive pulmonary disease (COPD), inflammation, inflammatory eye disease, inflammatory pulmonary diseases (e.g., chronic pneumonia, silicosis, pulmonary sarcoidosis, pulmonary tuberculosis and the like), arthritis (e.g., chronic rheumatoid arthritis, osteoarthritis, rheumatoid spondylitis, gout arthritis, synovitis and the like), inflammatory bowel diseases (e.g., Crohn's disease, ulcerative colitis and the like), psoriasis, rheumatism, meningitis, hepatitis, ischemic renal failure, nephritis, Addison's disease, systemic lupus erythematosus, osteoporosis, toxemia, cachexia, central nervous disorders (e.g., cerebrovascular disorders such as cerebral hemorrhage, cerebral infarction etc., head trauma, spinal trauma, brain edema and the like), arteriosclerosis, tumor and the like, prophylaxis or treatment of leukotriene-related diseases, prophylaxis or treatment of BLT2-related diseases and the like.

Particularly, since involvement of BLT2 in the onset and progress of arthritis (e.g., chronic rheumatoid arthritis and the like) is strongly suggested, the benzofuran compound of the present invention and a pharmaceutically acceptable salt thereof are useful for the prophylaxis or treatment of arthritis (e.g., chronic rheumatoid arthritis and the like) and the like.

The present invention is explained in detail by referring to Examples and Experimental Examples, which are not to be construed as limitative.

EXAMPLES

Example 1

Synthesis of (E)-3-[2-acetyl-7-(1-phenylethoxy)benzofuran-4-yl]-N,N-diethyl-2-butenamide (1) 1-(4-Bromo-7-hydroxybenzofuran-2-yl)ethanone (compound 2) (3 g, 0.012 mol), 1-bromoethylbenzene (2.0 ml, 0.144 mol) and $K_2CO_3$ (5.5 g, 0.036 mol) were dissolved or suspended in dry acetone, and the mixture was stirred with heating at 58° C. for 12 hr. After confirmation of disappearance of the starting materials by TLC, the mixture was air-cooled and filtered, and the solvent was evaporated. The obtained crystals were recrystallized from ethanol to give 1-[4-bromo-7-(1-phenylethoxy)benzofuran-2-yl]ethanone (compound 3) (3.3 g, yield 56.51%) as pale-yellow crystals.

Rf=0.45 (hexane:AcOEt=7:3) melting point: 128.8-131.8° C. $^1$H-NMR(CDCl$_3$, 60 MHz) (1.80(3H, d, J=7.0 Hz, OCHC$\underline{H}_3$), 2.68(3H, s, COC$\underline{H}_3$), 5.00-6.00(1H, m, OC$\underline{H}$(CH$_3$)), 7.21-7.69(8H, m, 3-H, 5-H, 6-H, Ar—H) EIMS(70 eV) m/s (rel. int. %) 358(M$^+$, 6.25) 239(14.89) 105(100.00) 77(27.76) HREIMS m/z 358.0205 (calcd for $C_{18}H_{15}O_3Br$, 358.0206)

(2) 1-[4-Bromo-7-(1-phenylethoxy)benzofuran-2-yl]ethanone (compound 3) (1.0 g, 2.79 mmol) and (E)-N,N-diethyl-2-butenamide (0.47 g, 3.35 mmol) were dissolved in triethylamine (10 ml), and the inside of the system was replaced by nitrogen gas. Palladium acetate (0.031 g, 0.14 mmol) and tri-o-tolylphosphine (0.085 g, 0.28 mmol) were added and the mixture was stirred with heating at 78-90° C. for 16 hr. After confirmation of the completion of the reaction by TLC, 5% HCl aqueous solution was added and the mixture was extracted with ethyl acetate. The mixture was washed with saturated brine, dried over $MgSO_4$, and the solvent was evaporated to give a brown oil. Purification by silica gel column chromatography (hexane:acetone=5:1) was performed to give (E)-3-[2-acetyl-7-(1-phenylethoxy)benzofuran-4-yl]-N,N-diethyl-2-butenamide (0.51 g, yield 43.6%) as a pale-yellow crystal.

m.p. 70.8-73.0° C. $^1$H-NMR (CDCl$_3$, 500 MHz) (1.16(3H, t, J=6.9Hz, —NCH$_2$C$\underline{H}_3$), 1.20(3H, t, J=6.9Hz, —NCH$_2$C$\underline{H}_3$), 1.76(3H, d, J=6.4 Hz, —O—CH(C$\underline{H}_3$)), 2.34(3H, d, J=1.0 Hz, —C=C$\underline{H}_3$), 2.64(3H, s, —COC$\underline{H}_3$), 3.37(2H, q, J=6.9 Hz, —C$\underline{H}_2$CH$_3$), 3.47(2H, q, J=6.8 Hz, —C$\underline{H}_2$CH$_3$), 5.57(1H, s, OC$\underline{H}$(CH$_3$)), 6.20(1H, d, J=0.9 Hz, —C=C—$\underline{H}$), 6.80(1H, d, J=8.2 Hz, benzofuran 5-H), 7.40(1H, d, J=8.2 Hz, benzofuran 6-H), 7.25-7.45(5H, m, Ar—H), 7.62(1H, s, benzofuran 3-H) EIMS(70 eV) m/s(rel. int. %) 419(M$^+$, 14.72) 315(100.00) 243(49.32) 105(92.11)

The compounds of Examples 2-27 were synthesized according to Example 1.

Example 2

(E)-3-[7-(3-carboxypropoxy)-4-(2-diethylcarbamoyl-1-methylvinyl)benzofuran-2-yl]-2-butenoic acid melting point: 199.5-201.9° C.

Example 3

(E,E)-3-[4-(2-diethylcarbamoyl-1-methylvinyl)-7-(3-ethoxycarbonylpropoxy)benzofuran-2-yl]-2-butenoic acid oil

Example 4

(E)-3-(2-acetyl-7-benzhydryloxybenzofuran-4-yl)-N,N-diethyl-2-butenamide melting point: 163.3-165.2° C.

Example 5

(E)-3-[2-acetyl-7-(1-phenylethoxy)benzofuran-4-yl]-1-(4-phenylpiperazin-1-yl)-2-buten-1-one melting point: 79.0-84.6° C.

Example 6

(E)-3-(2-acetyl-7-benzhydryloxybenzofuran-4-yl)-1-(4-phenylpiperazin-1-yl)-2-buten-1-one melting point: 152-160° C.

Example 7

(E)-3-(2-acetyl-7-benzhydryloxybenzofuran-4-yl)-1-morpholino-2-buten-1-one melting point: 167.0-169.3° C.

Example 8

(E)-3-[2-acetyl-7-(1-phenylethoxy)benzofuran-4-yl]-N-[2-(3,4-dimethoxyphenyl)ethyl]-2-butenamide melting point: 155.2-156.9° C.

Example 9

(E)-3-[2-acetyl-7-(1-phenylethoxy)benzofuran-4-yl]-1-morpholino-2-buten-1-one melting point: 173.9-175.4° C.

Example 10

(E)-3-[2-acetyl-7-(1-phenylethoxy)benzofuran-4-yl]-1-(4-benzylpiperazin-1-yl)-2-buten-1-one melting point: 196.0-202.1° C.

Example 11

(E)-3-(2-acetyl-7-benzhydryloxybenzofuran-4-yl)-N-[2-(3,4-dimethoxyphenyl)ethyl]-2-butenamide melting point: 208.3-209.0° C.

Example 12

(E)-3-(2-acetyl-7-benzhydryloxybenzofuran-4-yl)-1-(4-benzylpiperazin-1-yl)-2-buten-1-one melting point: 132.1-136.5° C.

Example 13

(E)-3-[2-acetyl-7-(2-benzo[1,3]dioxol-5-yloxoethoxy)benzofuran-4-yl]-N,N-diethyl-2-butenamide melting point: 142.0-144.0° C.

Example 14

Ethyl (E)-4-[2-acetyl-4-(2-diethylcarbamoyl-1-methylvinyl)benzofuran-7-yloxy]butyrate oil

Example 15

Ethyl (E)-3-amino-5-(2-diethylcarbamoyl-1-methylvinyl)benzofurane-2-carboxylate melting point: 159.5-162.0° C.

Example 16

Ethyl (E)-3-[3-(2-acetyl-3-aminobenzofuran-5-yl)-2-butenoylamino]-4-methoxybenzoate melting point: 189.0-193.0° C.

Example 17

(E)-3-(2-acetyl-3-aminobenzofuran-5-yl)-N-[2-(3,4-dimethoxyphenyl)ethyl]-2-butenamide melting point: 168.0-173.0° C.

Example 18

(E)-3-(2-acetyl-3-aminobenzofuran-5-yl)-1(4-phenylpiperazin-1-yl)-2-buten-1-one melting point: 158.6-160.7° C.

Example 19

(E)-3-(2-acetyl-3-aminobenzofuran-5-yl)-1-(4-benzylpiperazin-1-yl)-2-buten-1-one melting point: 144.0-148.3° C.

Example 20

(E)-N-[2-acetyl-5-(l-methyl-3-morpholino-3-oxo-1-propenyl)benzofuran-3-yl]-2-(4-methoxyphenyl) acetamide melting point: 132.7-134.2° C.

Example 21

(E)-3-{2-acetyl-3-[2-(4-methoxyphenyl)acetylamino]-benzofuran-5-yl}-N,N-diethyl-2-butenamide melting point: 121.8-122.3° C.

Example 22

(E)-3-[3-amino-2-(4-cyanobenzoyl)benzofuran-5-yl]-N,N-diethyl-2-butenamide melting point: 216.4-218.4° C.

Example 23

(E)-3-(2-acetyl-3-aminobenzofuran-5-yl)-1-morpholino-2-buten-1-one melting point: 256.4-262.1° C.

Example 24

(E)-3-(2-benzoylbenzofuran-5-yl)-N-[2-(3,4-dimethoxyphenyl)ethyl]-2-butenamide melting point: 126.9-129.4° C.

Example 25

(E)-3-(2-benzoylbenzofuran-5-yl)-1-morpholino-2-buten-1-one melting point: 115.5-117.0° C.

Example 26

(E)-3-(2-acetylbenzofuran-5-yl)-N-[2-(3,4-dimethoxyphenyl)ethyl]-2-butenamide melting point: 112.7-114.3° C.

Example 27

(E)-3-(2-acetylbenzofuran-5-yl)-1-morpholino-2-buten-1-one melting point: 138.9-141.8° C.

Example 28

Synthesis of ethyl (E)-4-{2-[2-(4-methoxyphenylcarbamoyl)-1-methylvinyl]benzofuran-7-yloxy}butyrate (1). 1-(7-hydroxybenzofuran-2-yl)ethanone (compound 1) (1.0 g, 5.68 mmol), ethyl 4-bromo-n-butyrate (1.33 g, 6.82 mmol) and $K_2CO_3$ (2.35 g, 17.04 mmol) were dissolved or suspended in dry acetone, and the mixture was stirred with heating at 56° C. for 8 hr. After confirmation of disappearance of the starting materials by TLC, the mixture was air-cooled and filtered, and the solvent was evaporated. The mixture was extracted with ethyl acetate, washed with saturated brine, dried over $MgSO_4$, and purified by silica gel column chromatography (hexane:ethyl acetate=20:1) to give ethyl 4-(2-acetylbenzofuran-7-yloxy)butyrate (compound 5) (1.19 g, yield 72.2%) as colorless crystals.

melting point: 47.1-48.4° C. $^1$H-NMR (CDCl$_3$, 60 MHz) (1.30(3H, t, J=7.0 Hz, —COOCH$_2$CH$_3$), 2.10-2.40(4H, m, —OCH$_2$CH$_2$CH$_2$COOC$_2$H$_5$), 2.70(3H, s, —COCH$_3$), 4.25 (2H, q, J=7.0 Hz, —OCH$_2$CH$_3$), 4.35(2H, q, J=6.0 Hz, —OCH$_2$CH$_2$CH$_2$), 6.95-7.30(3H, m, 4-H, 5-H, 6-H), 7.60(1H, s, 3-H) EIMS(70 eV) m/s(rel. int. %) 290(M$^+$, 3.433) 245(38.10) 176(19.96) 161(38.31) 115(100) HREIMS m/z 290.1153(calcd for $C_{10}H_{18}O_5$, 290.1154)

(2) NaH (0.17 g, 60% NaH, 4.25 mmol) was suspended in water-free THF (10 ml) and the inside of the reaction container was replaced with nitrogen gas. Then, diethyl [(4-methoxyphenylcarbamoyl)methyl]phosphate (1.28 g, 4.25 mmol) was added. Ethyl 4-(2-acetylbenzofuran-7-yloxy)butyrate (1.0 g, 3.4 mmol) was dissolved in water-free THF (10 ml) and added dropwise.

After the reaction, the solvent was evaporated under reduced pressure, saturated aqueous ammonium chloride solution was added, and the mixture was extracted with ethyl acetate. The organic layer was washed with saturated brine and dried over $MgSO_4$. The solvent was evaporated under reduced pressure. The residue was purified by silica gel column chromatography (CHCl$_3$:AcOEt=5:1) and the obtained crystals were recrystallized from methanol to give ethyl (E)-4-{2-[2-(4-methoxyphenylcarbamoyl)-1-methylvinyl]benzofuran-7-yloxy}butyrate (0.59 g, yield 39.6%) as yellow needle crystals.

melting point: 141.3-141.5° C. $^1$H-NMR (CDCl$_3$, 60 MHz) (1.24(3H, t, J=7.0 Hz, —OCH$_2$CH$_3$), 2.25(2H, p, J=7.0 Hz, —CH$_3$CH$_3$CH$_3$), 2.62(3H, d, J=1.1 Hz, —C(CH$_3$)), 2.66 (2H, t, J=7.0 Hz, —CH$_3$CO), 3.80(3H, s, —OCH$_3$), 4.17(2H, q, J=7.0 Hz, OCH$_2$CH$_3$), 4.31(2H, t, J=7.0 Hz, —OCH$_2$CH$_3$), 6.78(1H, q, J=1.1 Hz, —C(CH$_3$)=CH), 6.88(1H, d, J=8.8 Hz, 3'-H, 5'-H), 6.92(1H, s, 3-H), 6.95(1H, dd, J=7.7 Hz, 0.7 Hz, 6-H), 7.11(1H, d, J=7.7 Hz, 5-H), 7.19 (1H, dd, J=7.7 Hz, 0.7 Hz, 4-H), 7.56(1H, d, J=8.8 Hz, 2'-H, 6'-H), 7.90(1H, brs, NH, Exchange with D$_2$O) EIMS(70 eV) m/s (rel. int. %): 437(M$^+$, 58.89), 315(M$^+$,—NHC$_6$H$_4$OCH$_3$, 100.00), 123(—NHC$_6$H$_4$OCH$_3$, 50.99) HREIMS m/z 437.1844(Calcd for $C_{25}H_{27}NO_6$, 437.1839)

Example 29

Synthesis of (E)-4-{2-[2-(3-methoxyphenylcarbamoyl)-1-methylvinyl]benzofuran-7-yloxy}butyric acid NaH (0.12 g, 60% NaH, 2.93 mmol) was suspended in water-free THF (10 ml), the inside of the reaction container was replaced with nitrogen gas and diethyl [(3-methoxyphenylcarbamoyl)methyl]phosphate (0.88 g, 2.93 mmol) was added. Ethyl 4-(2-acetylbenzofuran-7-yloxy)butyrate (0.8 g, 2.34 mmol) was dissolved in water-free THF (10 ml) and added dropwise.

After the reaction, the solvent was evaporated under reduced pressure, saturated aqueous ammonium chloride solution was added, and the mixture was extracted with ethyl acetate. The organic layer was washed with saturated brine and dried over water-free MgSO$_4$. The solvent was evaporated under reduced pressure. The residue was purified by silica gel column chromatography (hexane:ethyl acetate=10:1(v/v)) and the obtained crystals were recrystallized from methanol to give ethyl (E)-4-{2-[2-(3-methoxyphenylcarbamoyl)-1-methylvinyl]benzofuran-7-yloxy}butyrate as crystals.

The obtained crystals of ethyl (E)-4-{2-[2-(3-methoxyphenylcarbamoyl)-1-methylvinyl]benzofuran-7-yloxy}butyrate were hydrolyzed by a conventional method to give (E)-4-{2-[2-(3-methoxyphenylcarbamoyl)-1-methylvinyl]benzofuran-7-yloxy}butyric acid as white crystals.

melting point: 155.5-157.5° C. $^1$H-NMR (Acetone, 400 MHz) (2.19(2H, m, —OCH$_2$CH$_2$CH$_2$-), 2.61(2H, t, —OCH$_2$CH$_2$CH$_2$, J=7.3 Hz), 2.62(3H, d, CH$_3$—C=CH—, J=1.1 Hz), 3.80(3H, s, —OCH$_3$), 4.35(2H, t, —OCH$_2$CH$_2$CH$_2$—, J=6.6 Hz), 6.65(1H, ddd, m-anisidine4-H, J=1.0, 2.1, 8.5 Hz), 6.87(1H, d, CH$_3$—C=CH—, J=1.4 Hz), 7.01(1H, dd, Bf6-H, J=1.1, 7.7 Hz), 7.15(1H, d, Bf5-H, J=7.7 Hz), 7.19(1H, s, Bf3-H), 7.22(1H, d, m-anisidine5-H, J=8.0 Hz), 7.23(1H, dd, Bf4-H, J=1.1, 7.7 Hz), 7.31(1H, m, m-anisidine6-H), 7.57(1H, t, m-anisidine2-H, J=1.8 Hz), 9.43(1H, s,NH) EIMS(70 eV) m/s (ref. int. %) 409(M$^+$, 26.39), 391 (8.72), 323(5.05), 287(100), 201(35.19) HREIMS m/z 409.15133(calcd for C$_{23}$H$_{23}$O$_6$N, 419.15053)

Example 30

Synthesis of ethyl (E)-4-[2-(1-methyl-3-morpholino-3-oxo-1-propenyl)benzofuran-7-yloxy]butyrate NaH (0.16 g, 60% NaH, 4.13 mmol) was suspended in THF (10 ml), and the inside of the reaction container was replaced with nitrogen gas. After ice-cooling to 0° C., diethyl (2-morpholino-2-oxoethyl)phosphate (1.09 g, 4.13 mmol) was dissolved in THF (15 ml) and the mixture was added dropwise to the mixture. After stirring to transparency while allowing the mixture to warm to room temperature, ethyl 4-(2-acetylbenzofuran-7-yloxy)butyrate (0.4 g, 1.69 mmol) was dissolved in THF (10 ml) and added dropwise to the mixture. The mixture was stirred at 23° C. for 1 hr. After confirmation of disappearance of the starting materials by TLC, THF was evaporated under reduced pressure. Then, water was added and the mixture was extracted with ethyl acetate. The organic layer was washed with saturated brine and dried over MgSO$_4$. The solvent was evaporated to give a yellow oil. This was purified by silica gel chromatography (CHCl$_3$:ethyl acetate=10:1 (v/v)) to give ethyl (E)-4-[2-(1-methyl-3-morpholino-3-oxo-propenyl)benzofuran-7-yloxy]butyrate (0.34 g, yield 24.6%) as white crystals.

Rf=0.53(CHCl$_3$:AcOEt=5:2) melting point: 90.0-94.8° C. $^1$H-NMR (CDCl$_3$, 400 MHz) (1.25(3H, t, —CH$_2$CH$_3$, J=7.3 Hz), 2.20(2H, m, —CH$_2$CH$_2$CH$_2$—), 2.30(3H, d, —CH=C—CH$_3$, J=1.1 Hz), 2.58(2H, t, —CH$_2$COO—, J=7.3 Hz), 3.60-3.75(8H, bs, —NCH$_2$CH$_2$O— x 2), 4.15(2H, q, —COOCH$_2$, J=7.3 Hz), 4.25(2H, t, —OCH$_2$—, J=6.2 Hz), 6.83(1H, s, benzofuran 3-H), 6.84(1H, d, —C=CH—, J=1.4 Hz), 6.85-7.17(3H, m, 4-H, 5-H, 6-H) EIMS(70 eV) m/z(ref. int. %) 401(M$^+$, 52.79), 315(30.08), 115(100) HREIMS m/z 401.1838(calcd for C$_{22}$H$_{27}$NO6, 401.1839)

The compounds of Examples 31-64 were synthesized according to Examples 28-30.

Example 31

(E)-4-[4,6-dibromo-2-(2-diethylcarbamoyl-1-methylvinyl)benzofuran-7-yloxy]butyric acid melting point: 121.0-123.0° C.

Example 32

Ethyl (E)-[2-(2-diethylcarbamoyl-1-methylvinyl)-4-ethylsulfamoylbenzofuran-7-yloxy]acetate melting point: 114.9-116.9° C.

Example 33

(E)-3-(7-isopropoxybenzofuran-2-yl)-N,N-diethyl-2-butenamide oil

Example 34

(Z)-3-(7-isopropoxybenzofuran-2-yl)-N,N-diethyl-2-butenamide oil

Example 35

Ethyl (E)-4-[4-bromo-2-(2-diethylcarbamoyl-1-methylvinyl)benzofuran-7-yloxy]butyrate melting point: 53.7-59.8° C.

Example 36

(E)-4-[4-bromo-2-(2-diethylcarbamoyl-1-methylvinyl)benzofuran-7-yloxy]butyric acid melting point: 125.5-127.0° C.

Example 37

(E)-3-(7-benzhydryloxybenzofuran-2-yl)-N,N-diethyl-2-butenamide oil

Example 38

(E)-3-(7-benzhydryloxybenzofuran-2-yl)-N-(3-methoxyphenyl)-2-butenamide melting point: 167.2-168.2° C.

Example 39

(E)-3-[4-bromo-7-(2-dimethylaminoethoxy)benzofuran-2-yl]-N-(3-methoxyphenyl)-2-butenamide melting point: 176.4-181.5° C.

Example 40

Ethyl (E)-4-{2-[2-(ethoxycarbonylmethylcarbamoyl)-1-methylvinyl]benzofuran-7-yloxy}butyrate melting point: 96.2-98.5° C.

Example 41

(E)-3-(7-benzhydryloxybenzofuran-2-yl)-N-(4-methoxyphenyl)-2-butenamide melting point: 191.8-193.6° C.

Example 42

(E)-3-(7-benzhydryloxybenzofuran-2-yl)-1-morpholino-2-buten-1-one oil

Example 43

(Z)-3-(7-benzhydryloxybenzofuran-2-yl)-N-(3,4-dimethoxyphenyl)-2-butenamide melting point: 93.9-94.5° C.

Example 44

(E)-3-(7-benzhydryloxybenzofuran-2-yl)-1-morpholino-2-buten-1-one melting point: 147.4-150.2° C.

Example 45

(E)-3-(7-benzhydryloxybenzofuran-2-yl)-N-(3,4-dimethoxyphenyl)-2-butenamide melting point: 93.9-94.5° C.

Example 46

Ethyl (Z)-4-{2-[2-(3,4-dimethoxyphenylcarbamoyl)-1-methylvinyl]benzofuran-7-yloxy}butyrate melting point: 101.5-105.0° C.

Example 47

(E)-3-(7-benzhydryloxybenzofuran-2-yl)-N-[2-(3,4-dimethoxyphenyl)ethyl]-2-butenamide melting point: 70.8-73.5° C.

Example 48

Ethyl (Z)-4-[2-(2-diethylcarbamoyl-1-methylvinyl)-4-ethylsulfamoylbenzofuran-7-yloxy]butyrate oil

Example 49

Ethyl (E)-4-(2-{2-[2-(3,4-dimethoxyphenyl)ethylcarbamoyl]-1-methylvinyl}benzofuran-7-yloxy)butyrate melting point: 114.0-115.5° C.

Example 50

3-{7-(3-chloropropoxy)-4-[2-(3,4-dimethoxyphenyl)ethylsulfamoyl]benzofuran-2-yl}-N,N-diethyl-2-butenamide oil

Example 51

(E)-3-{7-(3-chloropropoxy)-4-[2-(3,4-dimethoxyphenyl)ethylsulfamoyl]benzofuran-2-yl}-N-(3-methoxyphenyl)-2-butenamide melting point: 162.2-164.5° C.

Example 52

(Z)-3-{7-(3-chloropropoxy)-4-[2-(3,4-dimethoxyphenyl)ethylsulfamoyl]benzofuran-2-yl}-N-(3-methoxyphenyl)-2-butenamide melting point: 146.1-150.0° C.

Example 53

(2E,4Z)-5-chloro-5-[7-(3-chloropropoxy)benzofuran-2-yl]penta-2,4-dienoic acid (3,4-dimethoxyphenyl)amide melting point: 167.5-169.0° C.

Example 54

(2E,4Z)-5-(5-bromobenzofuran-2-yl)-5-chloropenta-2,4-dienoic acid (3-methoxyphenyl)amide melting point: 204.3-207.1° C.

Example 55

(2E,4Z)-5-(5-bromobenzofuran-2-yl)-5-chloropenta-2,4-dienoic acid [2-(3,4-dimethoxyphenyl)ethyl]amide melting point: 161.3-162.1° C.

Example 56

(2E,4Z)-5-chloro-5-(7-methoxybenzofuran-2-yl)-penta-2,4-dienoic acid [2-(3,4-dimethoxyphenyl)ethyl]amide melting point: 151.4-153.3° C.

Example 57

(2E,4Z)-5-chloro-5-(7-methoxybenzofuran-2-yl)penta-2,4-dienoic acid (3-methoxyphenyl)amide melting point: 194.3-197.3° C.

Example 58

(2E,4Z)-5-chloro-5-[7-(3-chloropropoxy)benzofuran-2-yl]penta-2,4-dienoic acid diethylamide oil

Example 59

(2E,4Z)-5-chloro-5-[7-(3-chloropropoxy)benzofuran-2-yl]-penta-2,4-dienoic acid diethylamide melting point: 74.0-76.9° C.

Example 60

(2E,4Z)-5-chloro-5-[7-(3-chloropropoxy)benzofuran-2-yl]penta-2,4-dienoic acid [2-(3,4-dimethoxyphenyl)ethyl]amide melting point: 149.0-150.0° C.

Example 61

(2E,4Z)-5-chloro-5-(7-methoxybenzofuran-2-yl)penta-2,4-dienenitrile melting point: 98.9-101.2° C.

Example 62

Ethyl (2E,4Z)-5-chloro-5-(7-methoxybenzofuran-2-yl)penta-2,4-dienoate melting point: 113.9-117.6° C.

Example 63

Ethyl (2E,4Z)-3-benzylsulfanyl-2-{5-chloro-5-[7-(3-chloropropoxy)benzofuran-2-yl]penta-2,4-dienoylamino}propionate melting point: 116.5-118.3° C.

Example 64

Ethyl (2E,4Z)-3-benzylsulfanyl-2-[5-(5-bromobenzofuran-2-yl)-5-chloropenta-2,4-dienoylamino]propionate melting point: 133.7-135.4° C.

Example 65

Synthetic method of N-(2-acetyl-5-bromobenzofuran-3-yl)-5-methylisoxazole-4-carboxamide Thionyl chloride (4.3 ml, 39.5 mmol) was added dropwise to 5-methylisoxazole-4-carboxylic acid (0.44 g, 3.4 mmol) at 26° C. The mixture was heated at 89° C. for 1 hr and allowed to cool. Excess thionyl chloride was evaporated under reduced pressure to give an acid chloride as a brown oil, which was used in the next reaction.

To a solution (10 ml) of 1-(3-amino-5-bromobenzofuran-2-yl)ethanone (0.2 g, 0.79 mmol) in water-free THF was added dropwise a solution (5 ml) of 5-methylisoxazole-4-carbonyl chloride (0.10 g, 0.79 mmol) in water-free THF under a nitrogen gas with vigorous stirring at 26-28° C. over 5 min. The reaction solution was heated at 65° C. for 2 hr. The reaction mixture was cooled to room temperature and the precipitate was collected by filtration. The precipitate was recrystallized from ethyl acetate to give N-(2-acetyl-5-bromobenzofuran-3-yl)-5-methylisoxazole-4-carboxamide as pale-yellow needle crystals (0.19 g, yield 68.0%).

melting point: 206-208° C.

Example 66

Synthesis of (Z)-N-(2-acetylbenzofuran-3-yl)-2-cyano-3-hydroxy-2-butenamide

To a solution (30 ml) of ethyl 5-bromo-3-[(5-methylisoxazole-4-carbonyl)amino]benzofurane-2-carboxylate (compound of Example 67 described below) (0.2 g, 1.8 mmol) produced according to Example 65 in water-free THF was added triethylamine (2.4 ml, 0.18 mmol), and the reaction mixture was heated at 68° C. for 6 hr and the solvent was evaporated. The residue was poured into ice water, and the mixture was acidified 30 with 5% aqueous hydrochloric acid solution and extracted with $CHCl_3$. The extract was washed with saturated brine and dried. The solvent was evaporated. The residue was recrystallized from acetonitrile to give (Z)-N-(2-acetylbenzofuran-3-yl)-2-cyano-3-hydroxy-2-butenamide as colorless crystals (0.23 g, yield 22.6%).

melting point: 206.1-208.1° C.

The compounds of Examples 67-133 were synthesized according to Examples 65 and 66.

Example 67

Ethyl 5-bromo-3-[(5-methylisoxazole-4-carbonyl)amino]benzofurane-2-carboxylate melting point: 170.0-172.8° C.

Example 68

Ethyl 3-[(5-methylisoxazole-4-carbonyl)amino]benzofurane-2-carboxylate melting point: 166.0-168.2° C.

Example 69

N-(2-acetylbenzofuran-3-yl)-5-methylisoxazole-4-carboxamide melting point: 174-177° C.

Example 70

N-[5-bromo-2-(1-hydroxyethyl)benzofuran-3-yl]-5-methylisoxazole-4-carboxamide melting point: 125.2-128.8° C.

Example 71

N-(2-acetyl-5-cyanobenzofuran-3-yl)-5-methylisoxazole-4-carboxamide melting point: 119.8-202.0° C.

Example 72

(E)-N-(2-acetyl-5-{2-[2-(3,4-dimethoxyphenyl)ethylcarbamoyl]-1-methylvinyl}benzofuran-3-yl)-5-methylisoxazole-4-carboxamide melting point: 156.0-168.0° C.

Example 73

N-[5-bromo-2-(4-cyanobenzoyl)benzofuran-3-yl]-5-methylisoxazole-4-carboxamide melting point: 236.3-238.9° C.

Example 74

(E)-N-[2-acetyl-5-(2-diethylcarbamoyl-1-methylvinyl)benzofuran-3-yl]-5-methylisoxazole-4-carboxamide melting point: 170.3-174.1° C.

Example 75

(E)-N-{2-acetyl-5-[1-methyl-3-oxo-3-(4-phenylpiperazin-1-yl)-1-propenyl]benzofuran-3-yl}-5-methylisoxazole-4-carboxamide melting point: 201.5-204.4° C.

Example 76

1-{3-[(5-methylisoxazole-4-carbonyl)amino]benzofuran-2-yl}ethyl acetate melting point: 130.2-132.9° C.

Example 77

N-[5-bromo-2-(4-chlorobenzoyl)benzofuran-3-yl]-5-methylisoxazole-4-carboxamide melting point: 240.8-243.2° C.

Example 78

N-[2-(4-bromobenzoyl)-7-methoxybenzofuran-3-yl]-5-ethylisoxazole-4-carboxamide melting point: 241.4-243.2° C.

Example 79

N-(2-carbamoylbenzofuran-3-yl)-5-methylisoxazole-4-carboxamide melting point: 250.7-252.6° C.

Example 80

N-(2-acetyl-7-methoxybenzofuran-3-yl)-5-methylisoxazole-4-carboxamide melting point: 181.0-181.7° C.

Example 81

(E)-N-[2-(4-cyanobenzoyl)-5-(1-methyl-3-morpholino-3-oxo-1-propenyl)benzofuran-3-yl]-5-methylisoxazole-4-carboxamide melting point: 229.4-232.5° C.

Example 82

N-[2-(4-chlorobenzoyl)-7-methoxybenzofuran-3-yl]-5-methylisoxazole-4-carboxamide melting point: 237.4-239.5° C.

Example 83

N-(2-acetyl-6-methoxybenzofuran-3-yl)-5-methylisoxazole-4-carboxamide melting point: 168.2-170.1° C.

Example 84

(E)-N-[2-(4-{2-[2-(3,4-dimethoxyphenyl)ethylcarbamoyl]-1-methylvinyl}benzoyl)-7-methoxybenzofuran-3-yl]-5-methylisoxazole-4-carboxamide melting point: 237.5-239.1° C.

Example 85

N-(5-bromo-2-cyanobenzofuran-3-yl)-5-methylisoxazole-4-carboxamide melting point: 239.2-241.9° C.

Example 86

N-(2-cyanobenzofuran-3-yl)-5-methylisoxazole-4-carboxamide melting point: 227.3-230.4° C.

Example 87

N-[2-(4-chlorobenzoyl)-7-methoxybenzofuran-3-yl]-5-methylisoxazole-4-carboxamide melting point: 237.4-239.5° C.

Example 88

Ethyl 3-[(5-methylisoxazole-4-carbonyl)amino]benzofurane-2-carboxylate melting point: 167.5-170.9° C.

Example 89

(E)-N-[2-(4-cyanobenzoyl)-5-(2-diethylcarbamoyl-1-methylvinyl)benzofuran-3-yl]-5-methylisoxazole-4-carboxamide melting point: 202.6-205.5° C.

Example 90

(E)-N-(2-(4-cyanobenzoyl)-5-{2-[2-(3,4-dimethoxyphenyl)ethylcarbamoyl]-1-methylvinyl}benzofuran-3-yl)-5-methylisoxazole-4-carboxamide melting point: 162.6-165.5° C.

Example 91

Ethyl (E)-5-(2-diethylcarbamoyl-1-methylvinyl)-3-[(5-methylisoxazole-4-carbonyl)amino]benzofurane-2-carboxylate melting point: 138.9-141.2° C.

Example 92

(Z)-3-(2-cyano-3-hydroxy-2-butenoylamino)benzofurane-2-carboxylic acid melting point: 196.3-196.6° C.

Example 93

(Z)-N-(2-acetyl-5-cyanobenzofuran-3-yl)-2-cyano-3-hydroxy-2-butenamide melting point: 216.0-218.0° C.

Example 94

N-{2-acetyl-5-[(E)-2-diethylcarbamoyl-1-methylvinyl]benzofuran-3-yl}-2-cyano-3-hydroxy-(Z)-2-butenamide melting point: 169.3-171.0° C.

Example 95

N-{2-acetyl-5-[1-methyl-3-oxo-3-(4-phenylpiperazin-1-yl)-(E)-1-propenyl]benzofuran-3-yl}-2-cyano-3-hydroxy-(Z)-2-butenamide melting point: 167.6-168.7° C.

Example 96

(Z)-N-(2-acetyl-5-bromobenzofuran-3-yl)-2-cyano-3-hydroxy-2-butenamide melting point: 221.9-222.4° C.

Example 97

Ethyl (Z)-5-bromo-3-(2-cyano-3-hydroxy-2-butenoylamino)benzofurane-2-carboxylate melting point: 186.3-187.2° C.

Example 98

(Z)-N-[5-bromo-2-(4-chlorobenzoyl)benzofuran-3-yl]-2-cyano-3-hydroxy-2-butenamide melting point: 263.3-265.3° C.

Example 99

(Z)-N-[2-(4-bromobenzoyl)-7-methoxybenzofuran-3-yl]-2-cyano-3-hydroxy-2-butenamide melting point: 131.7-133.4° C.

Example 100

(Z)-N-[5-bromo-2-(4-cyanobenzoyl)benzofuran-3-yl]-2-cyano-3-hydroxy-2-butenamide melting point: 269.3-271.2° C.

Example 101

(Z)-3-(2-cyano-3-hydroxy-2-butenoylamino)benzofurane-2-carboxamide melting point: 265° C.

Example 102

(Z)-N-(2-acetyl-7-methoxybenzofuran-3-yl)-2-cyano-3-hydroxy-2-butenamide melting point: 207.2-208.9° C.

Example 103

N-(2-acetyl-5-{(E)-2-[2-(3,4-dimethoxyphenyl)ethylcarbamoyl]-1-methylvinyl}benzofuran-3-yl)-2-cyano-3-hydroxy-(Z)-2-butenamide melting point: 176.7-179.7° C.

Example 104

(Z)-N-(5-bromo-2-cyanobenzofuran-3-yl)-2-cyano-3-hydroxy-2-butenamide melting point: 206.3-208.3° C.

Example 105

(Z)-N-(2-cyanobenzofuran-3-yl)-2-cyano-3-hydroxy-2-butenamide melting point: 165.8-167.2° C.

Example 106

N-[2-(4-{(E)-2-[2-(3,4-dimethoxyphenyl)ethylcarbamoyl]-1-methylvinyl}benzoyl)-7-methoxybenzofuran-3-yl]-2-cyano-3-hydroxy-(Z)-2-butenamide melting point: 202.9-205.8° C.

Example 107

Ethyl (Z)-3-(2-cyano-3-hydroxy-2-butenoylamino) benzofurane-2-carboxylate melting point: 147.5-150.1° C.

Example 108

N-[2-acetyl-5-(1-methyl-3-morpholino-3-oxo-(E)-1-propenyl)benzofuran-3-yl]-2-cyano-3-hydroxy-(Z)-2-butenamide melting point: 206.9-208.6° C.

Example 109

N-[2-(4-cyanobenzoyl)-5-((E)-2-diethylcarbamoyl-1-methylvinyl)benzofuran-3-yl]-2-cyano-3-hydroxy-(Z)-2-butenamide melting point: 219.5-222.8° C.

Example 110

(Z)-N-(2-acetyl-7-methoxybenzofuran-3-yl)-2-cyano-3-hydroxy-2-butenamide melting point: 207.2-208.9° C.

Example 111

N-(2-acetyl-7-methoxybenzofuran-4-yl)-5-methyl-isoxazole-4-carboxamide melting point: 201.8-205.9° C.

Example 112

(Z)-N-(2-acetyl-7-methoxybenzofuran-4-yl)-2-cyano-3-hydroxy-2-butenamide melting point: 243.4-246.4° C.

Example 113

(E)-N-[5-bromo-2-(4-chlorobenzoyl)benzofuran-3-yl]-3-phenylacrylamide melting point: 171.2-171.8° C.

Example 114

(E)-N-(2-acetyl-5-bromobenzofuran-3-yl)-3-phenylacrylamide melting point: 180.2-181.1° C.

Example 115

(E)-N-[5-bromo-2-(4-chlorobenzoyl)benzofuran-3-yl]-2-butenamide melting point: 210.4-212.8° C.

Example 116

(E)-N-(2-acetyl-6-methoxybenzofuran-3-yl)-2-butenamide melting point: 153.8-155.7° C.

Example 117

(E)-N-(5-bromo-2-cyanobenzofuran-3-yl)-2-butenamide melting point: 206.5-208.2° C.

Example 118

Ethyl (E)-3-methyl-acryloylaminobenzofurane-2-carboxylate melting point: 143.2-145.6° C.

Example 119

Ethyl (E)-3-(3-phenylacryloylamino)benzofurane-2-carboxylate melting point: 162.4-163.8° C.

Example 120

(E)-N-(2-acetyl-6-methoxybenzofuran-3-yl)-3-phenylacrylamide melting point: 142.0-144.5° C.

Example 121

(E)-3-(3-phenylacryloylamino)benzofurane-2-carboxylic acid melting point: 197.8-200.2° C.

Example 122

(E)-N-(5-bromo-2-cyanobenzofuran-3-yl)-3-phenylacrylamide melting point: 240.2-242.0°° C.

Example 123

(E)-N-(2-acetyl-5-bromobenzofuran-3-yl)-2-butenamide melting point: 127.8-130.0° C.

Example 124

Methyl (2-{1-[(5-methylisoxazole-4-carbonyl)amino]ethyl}benzofuran-7-yloxy)acetate melting point: 111.8-114.6° C.

Example 125

Ethyl 4-(4-ethylsulfamoyl-2-{1-[(5-methylisoxazole-4-carbonyl)amino]ethyl}benzofuran-7-yloxy)butyrate melting point: 88.1-90.0° C.

Example 126

(Z)-4-{2-[1-(2-cyano-3-hydroxy-2-butenoylamino)ethyl]benzofuran-7-yloxy}butyric acid melting point: 147.9-148.6° C.

Example 127

(E)-{2-[1-(2-cyano-3-hydroxy-2-butenoylamino)ethyl]benzofuran-7-yloxy}acetic acid melting point: 169.9-173.2° C.

Example 128

Ethyl (E)-4-{2-[1-(2-cyano-3-hydroxy-2-butenoylamino)ethyl]-4-ethylsulfamoylbenzofuran-7-yloxy}butyrate melting point: 121.0-122.1° C.

Example 129

(E)-4-{2-[1-(2-cyano-3-hydroxy-2-butenoylamino)ethyl]-4-ethylsulfamoylbenzofuran-7-yloxy}butyric acid melting point: 169.3-170.2° C.

Example 130

(E)-[1-(7-methoxybenzofuran-2-yl)ethyl]-2-butenamide melting point: 128.7-130.2° C.

Example 131

(E)-N-{1-[7-(3-chloropropoxy)benzofuran-2-yl]ethyl}-3-phenylacrylamide melting point: 132.2-139.7° C.

Example 132

(E)-N-[1-(7-methoxybenzofuran-2-yl)ethyl]-3-phenylacrylamide melting point: 154.5-156.5° C.

Example 133

(E)-N-{1-[7-(3-chloropropoxy)benzofuran-2-yl]ethyl}-2-butenamide melting point: 104.7-107.7° C.

The following compounds were synthesized according the aforementioned methods.

Example 134

(E)-3-(2-acetylbenzofuran-5-yl)-2-butenoic acid melting point: 220.4-223.5° C.

Example 135

(2E,4Z)-5-(2-butylbenzofuran-3-yl)-5-chloropenta-2,4-dienoic acid (4-methoxyphenyl)amide melting point: 91.3-93.2° C.

Example 136

(E,E)-3-[5-(1-methyl-3-morpholin-4-yl-3-oxopropenyl)benzofuran-2-yl]-2-butenoic acid melting point: 202.6-204.4° C.

Example 137

(E)-3-[2-acetyl-7-(3-chloropropoxy)benzofuran-4-yl]-2-butenoic acid diethylamide melting point: 80.6-82.1° C. pale-yellow white crystal

Example 138

(2E,4Z)-5-chloro-5-(7-methoxybenzofuran-2-yl)-1-morpholin-4-ylpenta-2,4-dien-1-one melting point: 185.4-186.6° C.

Example 139

(E)-3-{2-acetyl-7-(3-(4-chlorophenylsulfanyl)propoxy)benzofuran-4-yl}-2-butenoic acid diethylamide melting point: 110.5-113.5° C.

Example 140

Ethyl 4-[2-(1-chloro-3-oxopropenyl)benzofuran-7-yloxy]-butyrate melting point: 67.0-69.5° C.

Example 141

(E)-3-[3-(4-chlorophenyl)-5-methoxybenzofuran-2-yl]-N-(4-methoxyphenyl)acrylamide melting point: 194.0-195.1° C.

Example 142

(2E,4Z)-5-chloro-5-(7-methoxybenzofuran-2-yl)penta-2,4-dienoic acid diisopropylamide melting point: 140.1-142.0° C.

Example 143

(E)-3-[7-chloro-3-(4-chlorophenyl)benzofuran-2-yl]-2-butenoic acid (4-methoxyphenyl)-amide melting point: 168.9-170.0° C.

Example 144

(2E,4Z)-5-chloro-5-(7-methoxybenzofuran-2-yl)-1-piperidin-1-ylpenta-2,4-dien-1-one melting point: 142.2-144.4° C.

Example 145

Ethyl 4-[2-(1-chloro-5-morpholin-4-yl-5-oxo-penta-(1Z,3E)-1,3-dienyl)benzofuran-7-yloxy]butyrate oil $^1$H-NMR(CDCl$_3$, 500 MHz) δ1.26 (3H, t, J=6.9, CH$_2$CH$_3$), δ2.22 (2H, m, OCH$_2$CH$_2$CH$_2$), δ2.60 (2H, t, OCH$_2$CH$_2$CH$_2$), δ3.72 (8H, bs, NCH$_2$CH$_2$O×2), δ4.16 (2H, dd, J=6.9, CH$_2$CH$_3$), δ4.25 (2H, t, OCH$_2$CH$_2$CH$_2$), δ6.68 (1H, d, J=14.7, C(Cl)=CHCHCH), δ6.85 (1H, dd, J=7.55, J=0.9 Hz, 6-H), δ7.08 (1H, s, 3-H), δ7.13 (1H, dd, J=12.3, 5-H), δ7.18 (1H, dd, J=8.05, J=0.9, 4-H), δ7.30 (1H, d, J=11.0, C(Cl)=CHCHCH), δ7.81(1H, dd, J=14.7, J=11.5, C(Cl)=CHCHCH)

EIMS(70 eV)m/z(rel, int, %): 447 (M+,9.56), 412(84.08), 247(4.0 0), 115(100.00), 87(71.57), 29(22.23)

HREIMSm/z447.1447(calcd for C$_{21}$H$_{26}$ClNO$_6$, 447.1448)

Example 146

Ethyl 3-[2-(1-chloro-3-oxo-(Z)-propenyl)benzofuran-5-yl]-(E)-2-butenoate melting point: 99.5-101.0° C.

Example 147

(2E,4Z)-4-[2-(1-chloro-5-morpholin-4-yl-5-oxopenta-1,3-dienyl)benzofuran-7-yloxy]butyric acid melting point: 152.5-154.8° C.

Example 148

Ethyl 3-[2-(1-chloro-5-morpholin-4-yl-5-oxo-penta-(1Z,3E)-1,3-dienyl)benzofuran-5-yl]-(E)-2-butenoate melting point: 194.6-196.5° C.

Example 149

(E)-3-(2-butylbenzofuran-3-yl)-2-methyl-1-morpholin-4-ylpropenone oil $^1$H-NMR(CDCl$_3$, 400 MHz,) δ0.94(3H, t, J=7.5, CH$_2$CH$_2$CH$_2$CH$_3$), δ1.40 (2H, m, CH$_2$CH$_2$CH$_2$CH$_3$), δ1.73 (2H, m, CH$_2$CH$_2$CH$_2$CH$_3$), δ2.36 (3H, d, J=1.1, CH$_3$=CH), δ2.83 (2H, t, J=7.7, CH$_2$CH$_2$CH$_2$CH$_3$), δ3.73 (8H, m, NCH$_2$CH$_2$O×2), δ6.10 (1H, m, CH$_3$=CH), δ7.22 (2H, m, 5-H and 6-H), δ7.41 (1H, dd, J=7.5, J=1.6 Hz, 7-H), δ7.50 (1H, dd, J=6.8, J=2.0 Hz, 4-H)

EIMS (70 eV) m/z (rel. int, %): 327(M$^+$, 100.00), 241(87.89), 198(85.03), 270(44.19)

HREIMS m/z 327.1834(calcd for C$_{20}$H$_{25}$O$_3$N, 327.1834)

Example 151

(Z)-3-(5-bromo-2-methylbenzofuran-3-yl)-3-chloro-propenal melting point: 99.8-104.0° C.

Example 152

(E)-3-(5-bromo-3-methylbenzofuran-2-yl)-2-butenoic acid diethylamide oil $^1$H-NMR(CHCl$_3$, 400 MHz) δ1.21 (6H, t, J=7.24, CH$_2$CH$_3$), δ2.35 (3H, d,J=1.1, CH=CCH$_3$), δ2.37 (3H,s, CH$_3$), δ3.42 (2H, t,J=7.3, CH$_2$CH$_3$), δ3.49 (2H, t, J=7.3, CH$_2$CH$_3$), δ6.58 (1H, d, J=1.1,C=CH), δ7.27 (1H, d, J=9.2, 7-H), δ7.37 (1H, dd, J=8.4, 2.2, 6-H), δ7.61 (1H, d, J=1.1,4-H)

EIMS(70 eV)m/z(ref. int. %)351(52.43), (M$^+$, 54.08), 334 (14.02), 279 (100), 277 (99.32)

HREIMSm/z 349.0678(calcd for C$_{17}$H$_{20}$O$_2$NBr, 349.0677)

Example 153

(Z)-3-(5-bromo-3-methylbenzofuran-2-yl)-2-butenoic acid diethylamide melting point: 60.1-62.0° C.

Example 154

(2E,4Z)-5-(5-bromobenzofuran-2-yl)-5-chloropenta-2,4-dienenitrile melting point: 179-185° C.

Example 155

(E)-3-(2-butylbenzofuran-3-yl)-2-butenoic acid diethylamide

1H-NMR (CDCl$_3$,400 MHz) δ0.94 (3H, t, J=7.32, CH$_2$CH$_2$CH$_2$CH$_3$), δ1.20 (6H, m, N(CH$_2$CH$_3$)$_2$), δ1.40 (2H, m, CH$_2$CH$_2$CH$_2$CH$_3$), δ1.73 (2H, m, CH$_2$CH$_2$CH$_2$CH$_3$), δ2.37 (3H, d, J=1.46, C(CH$_3$)=CH), δ2.83 (2H,t, J=7.7, CH$_2$CH$_2$CH$_2$CH$_3$), δ3.41 (2H, q, J=7.3, NCH$_2$CH$_3$), δ3.49 (2H, q, J=7.3, NCH$_2$CH$_3$), δ6.14 (1H, q, J=1.1, C(CH$_3$)=CH), δ7.22 (2H, m, 5-H, 6-H), δ7.41 (1H, dd, J=7.35, J=2.25 Hz, 7-H), δ7.52 (1H, dd, J=6.65, J=1.5 Hz, 4-H)

EIMS(70 eV)m/z(rel., int., %)313(M$^+$,100),284(29.53), 256(52.9 2),241(59.18),213(20.81),198(42.54)

HREIMSm/z313.2045 (calcd for C$_{20}$H$_{27}$O$_2$N, 313.2042)

Example 157

(E)-3-(2-butylbenzofuran-3-yl)-2-butenoic acid [2-(3,4-dimethoxyphenyl)ethyl]amide melting point: 95-99° C.

Example 158

(E)-3-amino-5-(2-diethylcarbamoyl-1-methylvinyl)benzofurane-2-carboxylic acid (3-methoxyphenyl)amide melting point: 155-157° C.

Example 159

Ethyl (2E,4Z)-5-(5-bromobenzofuran-2-yl)-5-chloro-penta-2,4-dienoate melting point: 109-113° C.

Example 160

(E)-3-[7-(1-phenylethoxy)benzofuran-2-yl]-2-butenoic acid (3-methoxyphenyl)amide oil δ1.77(3H, d, J=6.2, OCH(CH$_3$)), δ2.60(3H, d, J=1.5, C(CH$_3$)=CH), δ3.83(3H, s, OCH$_3$), δ5.55(1H, q, OCH(CH$_3$), J=6.6 Hz), δ6.70(1H, dd, J=1.9, 4'-H), δ6.75(1H, dd, J=0.8, J=1.1, 4-H or 6-H,), δ6.94(1H, s, 3-H), δ7.00(1H, s, J=8.0, 5-H), δ7.12(1H, dd, J=7.7, 1.1, 4-H or 6-H), δ7.22-7.48(8H, m, NH, 5'-H, 6'-H, phenyl-H), δ7.41(1H, bs, 2'-H)

EIMS(70 eV)m/z(rel., int., %)427(M$^+$, 16.13)323(50.94) 201(100)105(85.10)

HREIMSm/z427.1787(cald for C$_{27}$H$_{25}$O$_4$N,427.1784)

Example 161

(Z)-3-[7-(1-phenylethoxy)benzofuran-2-yl]-2-butenoic acid (3-methoxyphenyl)amide oil δ1.47(3H, d, J=6.5, OCH(CH$_3$)), δ2.28(3H, d, J=1.5, C(CH$_3$)=CH), δ3.75(3H, s, OCH$_3$), δ5.46(1H, q, J=6.6, OCH(CH$_3$)), δ6.08(1H, d, J=1.5, C(CH$_3$)=CHCO), δ6.64(1H, dd, J=2.5, 1.1, 3'-H), δ6.66(1H, d, J=7.3, 4-H or 6-H), δ6.96 (1H, dd, J=2.5, 1.1, 5-H), δ7.02(1H, s, 3-H), δ7.08(1H, dd, J=0.8, 7.7, 4-H or 6-H), δ7.36(1H, bs, 2'-H), δ7.15-7.38(8H, m, 5'-H,6'-H, phenyl-H)

EIMS(70 eV)m/z(rel., int., %)427(M$^+$, 14.40)323(17.64) 201(100)105(43.67)

HREIMSm/z427.1782(cald for C$_{27}$H$_{25}$O$_4$N,427.1784)

Example 162

(E)-1-morpholin-4-yl-3-[7-(1-phenylethoxy)benzofuran-2-yl]-2-buten-1-one oil $^1$H-NMR(CHCl$_3$,400 MHz) δ1.73 (3H, d, J=6.59, OCH(CH$_3$)), δ2.29 (3H, d, J=1.46, C(CH$_3$)=CH), δ3.61-3.74(8H, m, NCH₂CH₂O×2), δ5.55(1H, q, J=6.2, OCH(CH₃)), δ6.73 (1H, dd, J=1.1, 8.1, 4-H or 6-H), δ6.81(1H, s, 3-H), δ6.84(1H, dd, J=1.1, C(CH₃)=CH), δ6.99(1H, dd, J=8.1, 5-H), δ7.10 (1H, dd, J=1.1, 8.1, 4-H or 6-H)

EIMS(70 eV)m/z(rel., int., %)391(M⁺,6.47)287(100.00) 201(47.5 2)105(60.41)

HREIMSm/z391.1785(cald for $C_{24}H_{25}O_4N$ 391.1784)

Example 163

(Z)-1-morpholin-4-yl-3-[7-(1-phenylethoxy)benzofuran-2-yl]-2-buten-1-one oil

¹H-NMR(CHCl₃,400 MHz), δ1.70(3H, d, J=6.59, OCH(CH₃)), δ2.21(3H,d, J=1.46, C(CH₃)=CH), δ3.46-3.79(8H,m, NCH₂CH₂O×2), δ5.56(1H, q, J=6.5, OCH(CH₃)), δ5.96(1H, d, J=1.5, C(CH₃)=CH), δ6.70(1H, dd, J=0.7, 4-H or 6-H), δ6.76(1H, s, 3-H), δ6.97(1H, dd, J=7.7, 5-H), δ7.07(1H, dd, J=0.7, 1.1, 4-H or 6-H)

EIMS(70 eV)m/z(rel., int., %)391(M+,12.12)287(100.00) 201(65.53)105(41.50)

HREIMSm/z391.1780(cald for $C_{24}H_{25}O_4N$,391.1783)

Example 164

(E)-3-[7-(1-phenylethoxy)benzofuran-2-yl]-2-butenoic acid [2-(3,4-dimethoxyphenyl)ethyl]amide melting point: 109-113° C.

Example 165

(Z)-3-[7-(1-phenylethoxy)benzofuran-2-yl]-2-butenoic acid [2-(3,4-dimethoxyphenyl)ethyl]amide ¹H-NMR(CHCl₃, 400 MHz) δ1.68(3H, d, J=6.6, OCH(CH₃)), δ2.20(3H,d, J=1.4, C(CH₃)=CH), δ2.78(2H, t, J=7.0, NHCH₂CH₂), δ3.60-3.65(2H, m, NHCH₂CH₂), δ3.69 (3H, s, OCH₃), δ3.80(3H, s, OCH₃), δ5.56(1H, q, J=6.2, OCH(CH₃)), δ5.83(1H, t, J=5.5, NH), δ5.95(1H, d, J=1.5, CH₃C=CH), δ6.60-6.69(3H, m, 2'-,5'-, 6'-H), δ6.71(1H, dd, J=1.1, 8.1, 4-H or 6-H), δ6.94(1H, s, 3-H), δ6.98(1H, dd, J=7.7, 5-H), δ7.09(1H, dd, J=8.1, 0.7, 4-H or 6-H)

EIMS(70 eV)m/z(rel., int., %)485(M+, 2.15)381(10.37) 164(100.00)105(44.40)

HREIMSm/z485.2199(cald for $C_{30}H_{31}O_5N$, 485.2202)

Example 166

(E)-3-(3-ethylbenzofuran-2-yl)-1-morpholin-4-yl-2-buten-1-one oil

δ1.30 (3H, t, J=7.32, CH₂CH₃), δ2.38 (3H, d, J=1.46, C(CH₃)=CH), δ2.90 (2H, q, J=7.4, CH₂CH₃), δ3.60-3.80 (8H, m, NCH₂CH₂O×2), δ6.56 (1H, q, J=1.1, C(CH₃)=CH), δ7.20-7.33 (2H, m, 5,6-H), δ7.41 (1H, dd, 7-H, J=8.45, J=0.7 Hz), δ7.53 (1H, dd, 4-H, J=7.55, J=1.05 Hz)

EIMS (70 eV) m/z (rel., int., %) 299 (M+,58.22), 213 (100), 185 (31.70), 270 (13.08)

Example 167

3-(3-ethylbenzofuran-2-yl)-2-butenoic acid [2-(3,4-dimethoxyphenyl)ethyl]amide melting point: 131-135° C.

Example 169

3-(5-bromo-2-methylbenzofuran-3-yl)-2-butenoic acid diethylamide oil

¹H-NMR, 400 MHz, CDCl₃ δ0.91 (3H, t, J=6.9, CH₂CH₃), δ1.02 (3H, t, J=6.9, CH₂CH₃), δ1.21 (6H, t, J=6.9, CH₂CH₃), δ2.16 (3H, d, J=1.5, Z-CH=CCH₃), δ2.34 (3H, d, J=1.1, E-CH=CCH₃), δ2.38 (3H, s, Z-CH₃), δ2.20 (3H, s, E-CH₃), δ3.23-3.31 (4H, m, CH₂CH₃×2), δ3.42 (2H, q, J=7.0, CH₂CH₃), δ3.49 (2H, d, J=6.9, CH₂CH₃), δ6.13 (1H, q, J=1.1, E-CH=CCH₃), δ6.22 (1H, q, J=1.5, Z-CH=CCH₃), δ7.23 (1H, d, J=8.8, Z-7-H), δ7.27 (1H, d, J=8.8, E-7-H), δ7.28 (1H, dd, J=8.8 and 1.9, Z-6-H), δ7.33 (1H, dd, J=8.8 and 1.9, E-6-H), δ7.46 (1H, d, J=2.2, Z-4-H), δ7.64 (1H, d, J=2.2, E-4-H), δ5.25 (1H, s, CH), δ6.92-7.59 (4H, m, Ar—H)

EIMS(70 eV)m/z(ref. int. %) 172 (M⁺, 100), 157 (64.51), 132 (85.08)

Example 170

(E)-3-(2-acetyl-5-chloro-benzofuran-7-yl)-2-butenoic acid diethylamide melting point: 116-117.5° C.

Example 171

(E)-1-(4-benzylpiperazin-1-yl)-3-(2-butylbenzofuran-3-yl)-2-buten-1-one oil

¹H-NMR (CDCl₃, 500 MHz) δ0.93 (3H, t, J=7.8, CH₂CH₂CH₂CH₃), δ1.36-1.42 (2H, m, J=7.8, CH₂CH₂CH₂CH₃), δ1.69-1.75 (2H, m, J=7.8, CH₂CH₂CH₂CH₃), δ2.32 (3H, d, J=0.9, C(CH₃)=CH), δ2.82 (2H, t, J=7.8, CH₂CH₂CH₂CH₃), δ3.55 (2H, s, CH₂C₆H₅), δ3.59-3.79 (8H, m, NCH₂CH₂N×2), δ6.10 (1H, q, J=1.35, C(CH₃)=CH), δ7.18-7.25 (2H, m, 5-H, 6-H), δ7.26-7.33 (5H, m, phenyl-H), δ7.40 (1H, m, 7-H), δ7.49 (1H, dd, J=1.8, J=7.8, 4-H)

EIMS (70 eV)m/z (rel., int., %) 416 (M⁺, 13.51) 359 (1.74) 241 (12.61) 91 (100)

Example 172

(E)-3-[7-(1-phenylethoxy)benzofuran-2-yl]-2-butenoic acid (4-methoxyphenyl)amide melting point: 120-125° C.

Example 173

(E)-5-methylisoxazole-4-carboxylic acid [5-bromo-2-(3-phenylacryloyl)benzofuran-3-yl]amide melting point: 219.6-220.3° C.

Example 174

2-cyano-3-hydroxy-(Z)-2-butenoic acid [5-bromo-2-((E)-3-phenylacryloyl)benzofuran-3-yl]amide melting point: 261.5-262.8° C.

Example 175

(E)-5-phenyl-2-penteneoic acid (2-acetyl-5-bromobenzofuran-3-yl)amide melting point: 129-131° C.

Example 176

(E,E)-N-[5-bromo-2-(3-dimethylaminoacryloyl)-benzofuran-3-yl]-3-phenylacrylamide melting point: 248.0° C.

Example 177

(E) -2-butenoic acid [5-bromo-2-(3-dimethylamino-(E)-acryloyl)benzofuran-3-yl]amide melting point: 247.5-249.5° C.

Example 178

(E)-N-(2-acetyl-5-bromobenzofuran-3-yl)-3-(4-methoxyphenyl)acrylamide melting point: 182.5-184.7° C.

Example 179

(E)-N-[2-(4-bromobenzoyl)-7-methoxybenzofuran-3-yl]-3-phenylacrylamide melting point: 236.5-237.8° C.

Example 180

(E)-N-(5-bromo-2-chlorobenzofuran-3-yl) -3-phenylacrylamide melting point: 248.7-250.3° C.

Example 181

(E)-N-(2-chloro-7-methoxybenzofuran-3-yl)-3-phenylacrylamide melting point: 220.0-221.3° C.

Example 182

(E)-N-(2-acetyl-7-methoxybenzofuran-3-yl)-3-phenylacrylamide melting point: 160.6-161.1° C.

Example 183

5-methyl-isoxazole-4-carboxylic acid [5-bromo-2-(3-methoxyphenylcarbamoyl)benzofuran-3-yl]amide melting point: 223-229° C.

Example 184

(E)-2-butenoic acid (5-bromo-2-chlorobenzofuran-3-yl)amide melting point: 200-202° C.

Example 185

(E)-2-butenoic acid (2-acetyl-7-methoxybenzofuran-3-yl)amide melting point: 165.7-168.0° C.

Example 186

(E)-5-methyl-isoxazole-4-carboxylic acid [5-((E)-2-diethylcarbamoyl-1-methylvinyl)-2-(3-methoxyphenylcarbamoyl)benzofuran-3-yl]amide melting point: 204-206° C.

Example 187

(E)-2-butenoic acid (2-chloro-7-methoxybenzofuran-3-yl)amide melting point: 216-217° C.

Example 188

(Z)-5-bromo-3-(2-cyano-3-hydroxy-2-butenoylamino)benzofurane-2-carboxylic acid (3-methoxyphenyl)amide melting point: 234.5-241.5° C.

Example 189

3-(2-cyano-3-hydroxy-(Z)-2-butenoylamino)-5-((E)-2-diethylcarbamoyl-1-methylvinyl)-benzofurane-2-carboxylic acid(3-methoxyphenyl)amide melting point: 172-174° C.

Example 190

N-(1-benzofuran-2-ylethyl)acetamide melting point: 128-130° C.

Example 191

N-[1-(7-methoxybenzofuran-2-yl)ethyl]acetamide melting point: 90-91.8° C.

Example 192

(E)-2-butenoic acid (1-(benzofuran-2-yl)ethyl)amide melting point: 98-100° C.

Example 193

N-(2-acetyl-5-bromobenzofuran-3-yl)-2-cyanoacetamide melting point: 214.4-215.1° C.

Example 194

(E)-N-[5-bromo-2-(3-dimethylaminoacryloyl)benzofuran-3-yl]acetamide melting point: 221.1-222.0° C.

Example 195

(E)-N-{5-bromo-2-[3-(4-methoxyphenyl)-acryloyl]benzofuran-3-yl}-3-chloropropionamide melting point: 170.7-172.0° C.

Example 196

(E)-2-benzylamino-N-{5-bromo-2-[3-(4-methoxyphenyl)acryloyl]benzofuran-3-yl}acetamide melting point: 174.2-176.5° C.

Example 197

N-[5-bromo-2-(4-chlorobenzoyl)benzofuran-3-yl]-2-cyanoacetamide melting point: 245.4-249.5° C.

Example 198

N-[2-(4-bromobenzoyl)-7-methoxybenzofuran-3-yl]-2-cyanoacetamide melting point: 312.2-348.6° C.

Example 199

Ethyl N-(2-acetyl-5-bromobenzofuran-3-yl)oxamic acid melting point: 196.4-197.9° C.

Example 200

N-(5-bromo-2-chlorobenzofuran-3-yl)-4-methoxybenzamide melting point: 195.5-197° C.

Example 201

(E)-N-[5-bromo-2-(3-phenylacryloyl)-benzofuran-3-yl]-3-chloropropionamide melting point: 204.7-206.8° C.

Example 202

N-[1-(3-acetylbenzofuran-2-yl)ethyl]acetamide

The compound becomes viscous at 102.1-106.9° C. and becomes liquid at 109.9° C.

Example 203

(E)-3-benzylamino-N-{5-bromo-2-[3-(4-methoxyphenyl)acryloyl]benzofuran-3-yl}propionamide melting point: 123.8-126.5° C.

Example 204

N-(2-acetyl-7-methoxybenzofuran-3-yl)-3-chloropropionamide melting point: 169.1-170.2° C.

Example 205

N-(2-acetyl-7-methoxybenzofuran-3-yl)-2-chloroacetamide melting point: 186.2-188.3° C.

Example 207

Ethyl N-[5-bromo-2-(4-chlorobenzoyl)-benzofuran-3-yl]oxamic acid melting point: 203-204° C.

Example 208

N-(2-acetyl-7-methoxybenzofuran-3-yl)acetamide melting point: 206.6-209.5° C.

Example 209

N-(2-acetyl-5-bromobenzofuran-3-yl)-2-methoxybenzamide melting point: 165-168° C.

Example 210

N-(2-acetyl-5-bromobenzofuran-3-yl)-3,4,5-trimethoxybenzamide melting point: 212.0-212.3° C.

Example 211

N-(2-acetyl-4-bromo-7-methoxybenzofuran-3-yl)acetamide melting point: 235.3-237.8° C.

Example 212

4-(5-bromobenzofuran-2-yl)-2-phenylthiazole melting point: 185.5-187.8° C.

Example 213

4-[7-chloro-3-(4-chlorophenyl)benzofuran-2-yl]-2-phenylthiazole melting point: 165.5-166.0° C.

Example 214

4-[7-chloro-3-(4-chlorophenyl)benzofuran-2-yl]-2-methylthiazole melting point: 156.4-158.4° C.

Example 215

4-[3-(4-chlorophenyl)-5-methoxybenzofuran-2-yl]-2-phenylthiazole melting point: 151.3-153.3° C.

Example 216

4-(5-bromobenzofuran-2-yl)-2-methylthiazole melting point: 167.4-167.9° C.

Example 217

4-[3-(4-chlorophenyl)-5-methoxybenzofuran-2-yl]-2-methylthiazole melting point: 105.8-106.5° C.

Example 218

4-[3-(4-chlorophenyl)-5-methoxybenzofuran-2-yl]thiazol-2-ylamine melting point: 196.0-197.7° C.

Example 219

N'-{4-[3-(4-chlorophenyl)-5-methoxybenzofuran-2-yl]thiazol-2-yl}-N,N-dimethylformamidine melting point: 142.7-144.3° C.

Example 220

5-methylisoxazole-4-carboxylic acid {4-[3-(4-chlorophenyl)-5-methoxybenzofuran-2-yl]thiazol-2-yl}amide melting point: 216.8-218.7° C.

Example 221

N'-{4-[3-(4-chlorophenyl)-5-methoxybenzofuran-2-yl]-5-formylthiazol-2-yl}-N,N-dimethylformamidine melting point: 203.5-205.0° C.

Example 222

(Z)-2-cyano-3-hydroxy-2-butenoic acid {4-[3-(4-chlorophenyl)-5-methoxybenzofuran-2-yl]thiazol-2-yl}amide melting point: 229.5-231° C.

Example 223

N'-{4-[3-(4-chlorophenyl)-5-methoxybenzofuran-2-yl]-5-[(2-hydroxyethylimino)methyl]thiazol-2-yl}-N,N-dimethylformamidine melting point: 167.8-169.2° C.

Example 224

Ethyl (E)-4-[2-(2-diethylcarbamoyl-1-methylvinyl)benzofuran-7-yloxy]butyrate $^1$H-NMR (CHCl$_3$, 500 MHz) δ1.20 (3H, t, CH$_2$CH$_3$,J=7.35), δ1.21 (3H, t, CH$_2$CH$_3$,J=7.3z), δ1.26(3H, t, CH$_2$CH$_3$,J=7.30) δ2.19(2H, m, OCH$_2$CH$_2$CH$_2$), δ2.30(3H, d, C=CCH$_3$,J=0.9), δ2.58(2H, t, OCH$_2$CH$_2$CH$_2$,J=7.30), δ3.45(2H, q, NCH$_2$CH$_3$,J=7.3), δ3.46(2H, q,NCH$_2$CH$_3$,J=7.3), δ4.14(2H, q, COOCH$_2$CH$_3$,J=7.3), δ4.26 (2H, t, OCH$_2$CH$_2$CH$_2$,J=6.5), δ6.80(1H, S, 3-H), δ6.48(1H, d, 4-H or 6-H, J=7.8), δ6.89(1H, d, C=CH,J=0.9), δ7.10(1H, dd, 5-H, J=7.8), δ7.15(1H, dd, 4-H or 6-H, J=7.75, J=0.9)

EIMS(70 eV)m/z(ref. int. %)387(M$^+$,44.39)342(13.84) 315(25.79) 286(17.63)115(100)

HREIMSm/z387.2046(calcd for C$_{22}$H$_{29}$O$_5$N,387.2046)

Example 225

Ethyl (Z)-4-[2-(2-diethylcarbamoyl-1-methylvinyl)benzofuran-7-yloxy]butyrate $^1$H-NMR (CHCl$_3$, 500 MHz) δ1.03 (3H, t, CH$_2$CH$_3$,J=7.30),δ1.22 (3H,t, CH$_2$CH$_3$,J=7.30 Hz),δ1.26 (3H, t, CH$_2$CH$_3$, J=7.4),δ2.16 (2H, m, OCH$_2$CH$_2$CH$_2$),δ2.22 (3H, d, C=CCH$_3$, J=1.3),δ2.56 (2H, t, OCH$_2$CH$_2$CH$_2$, J=7.7), δ3.34 (2H, q, NCH$_2$CH$_3$, J=7.3),δ3.52 (2H, q, NCH$_2$CH$_3$, J=7.3) δ4.15 (2H, q, COOCH$_2$CH$_3$, J=7.4),δ4.22 (2H, t, OCH$_2$CH$_2$CH$_2$,J=6.4),δ6.00 (1H, d, C=CH, J=1.3),δ6.77 (1H, dd, 4-H or 6-H, J=7.8 Hz, J=1.1),δ6.83 (1H, s, 3-H),δ7.07 (1H, dd, 5-H, J=7.8),δ7.11 (1H, dd, 4-H or 6-H, J=7.8, J=1.4)

EIMS (70 eV) m/z (ref.int. %) 387 (M$^+$, 53.86)342(17.68) 315(26.97) 286(24.41)115(100)

HREIMSm/z387.2046(calcd for C$_{22}$H$_{29}$O$_5$N,387.2046)

Example 226

3-chloro-3-(7-methoxy-benzofuran-2-yl)-propenal melting point: 124.3-127.2° C.

Example 227

Ethyl (E)-4-{2-[2-(3,4-dimethoxyphenylcarbamoyl)-1-methylvinyl]benzofuran-7-yloxy}butyrate melting point: 124.5-127.4° C.

EXPERIMENTAL EXAMPLES

Experimental Example 1

The LTB4 receptor antagonist activity of the test compound was examined using, as an index, thromboxane B2 (TXB2) released when stimulating eosinophil of guinea pig with LTB4.

(Test Method)

Based on the method described in Japanese Journal of Pharmacology, vol. 70, p. 337-345 (1996) etc., eosinophils of guinea pig were prepared. A cell suspension (300 μl, 1.25×10$^6$ cells/ml) was placed in a 5 ml polypropylene test tube and, after incubation at 37° C. for 5 min., 10$^{-3}$ M test compound (37.5 μl) dissolved in 0.1% DMSO aqueous solution was added and the cells were continuously cultured for 5 min. Then, 10$^{-7}$ M LTB4 (37.5 μl) was added to induce the reaction and the cells were incubated at 37° C. for 15 min. The reaction was quenched in ice water, and the culture was centrifuged at 4° C., 3000 rpm for 10 min. The obtained supernatant was prepared as a sample for TXB2 measurement, and preserved at −80° C. before use for the measurement. The quantitation of TXB2 was performed using a TXB2 enzyme immunoassay kit (manufactured by Cayman Chemical Company). The release ratio (%) of TXB2 from the eosinophils was determined by the following formula: release ratio (%) of TXB2= [(average value of test compound administration group−average value of negative control group)/(average value of positive control group−average value of negative control group)]×100

As used herein, the positive control group means a group to which stimulation with LTB4 was applied but the same volume of a medium was given instead of the test compound, and the negative control group means a group to which stimulation with LTB4 was not applied, the same volume of a medium was given instead of LTB4, and the same volume of a medium was given instead of the test compound. When the release ratio of TXB2 is smaller than 0, it means that the measured TXB2 concentration was lower than that of the negative control group. When the TXB2 concentration in the sample was the measurement limit or less, N.D. is indicated.

(Results)

The results are shown in Table 1 and Table 2.

TABLE 1

| Example No. | Amount of TXB2 release (%) |
|---|---|
| negative control group | 0 |
| positive control group | 100 |
| 1 | 0.42 |
| 2 | 5.77 |
| 4 | N.D. |
| 5 | 81.6 |
| 6 | 38.93 |
| 7 | 9.89 |
| 8 | 41.73 |
| 9 | 0.68 |
| 10 | 23.43 |
| 13 | 31.8 |
| 14 | 44.81 |
| 16 | 56.57 |
| 17 | 27.92 |
| 18 | 53.91 |
| 19 | 48.63 |
| 21 | 56.57 |
| 28 | −0.23 |
| 29 | −0.19 |
| 30 | 0.086 |
| 33 | −0.199 |
| 34 | −0.063 |
| 35 | 1.02 |
| 36 | −0.301 |
| 37 | 15.69 |

TABLE 2

| Example No. | Amount of TXB2 release (%) |
|---|---|
| 38 | 91.73 |
| 39 | N.D. |
| 40 | −0.18 |
| 42 | 13.83 |
| 46 | 45.62 |
| 48 | 53.91 |
| 49 | 2.37 |
| 51 | 38.93 |
| 52 | 60.6 |
| 54 | 60.6 |
| 55 | 53.91 |
| 56 | 52.39 |
| 57 | 78.01 |
| 72 | 84.46 |
| 75 | 27.03 |
| 94 | −0.1 |
| 97 | −0.12 |
| 114 | 51.42 |
| 117 | 54.95 |
| 118 | 73.84 |
| 119 | 9.8 |
| 120 | 1.32 |
| 121 | 5.77 |
| 130 | 35.44 |
| 131 | 2.14 |
| 132 | 14.05 |

As is clear from the results of Table 1 and Table 2, it has been demonstrated that the test compound has a superior leukotriene inhibitory action, particularly, a superior leukotriene B4 inhibitory action.

Experimental Example 2

(Test Method)

CHO cells habouring a gene encoding human BLT1 or human BLT2 and functionally expressing the receptor were seeded in a 96 well plate at $4 \times 10^4$ cells/well, and cultured at 37° C. for 60 min. The culture supernatant was removed and a loading buffer (100 µl) containing 4 µM Fluo-3 (manufactured by Dojindo), 0.04% pluoronic acid (manufactured by Sigma) and 1% serum was added. The mixture was culture at 37° C. for 30 min to introduce Fluo-3 into the cells. After culture, the cells were washed with a buffer, and a buffer containing various compounds (10 µM (final concentration)) was added, and then 100 nM (final concentration) of LTB4 was added. Changes in the intracellular calcium ion concentration were measured with Flexstation (manufactured by Molecular Devices Corporation) as increase in the fluorescence intensity (area under a curve in a time-course graph of fluorescence intensity in 10 min measurement). As a positive control of BLT1 and BLT2 antagonists, ZK158252 was used.

(Results)

Increase in the intracellular calcium ion concentration due to stimulation of CHO cells, into which BLT1 or BLT2 had been introduced, with LTB4 was significantly suppressed by ZK158252 to a similar level.

Increase in the intracellular calcium ion concentration of CHO cell, into which BLT2 had been introduced, was suppressed by each of the compounds of Example 33, Example 1, Example 40, Example 46, Example 29, Example 30, Example 49, Example 59, Example 224, Example 225, Example 7, Example 9, Example 14, Example 137, Example 142, Example 94, Example 97, Example 120, Example 131, Example 226, Example 98, Example 141, Example 144, Example 180, Example 219 and Example 222 by not less than 30% of the level of suppression by ZK158252, thereby demonstrating that the compound of the present invention has superior BLT2 competitive inhibitory activity. Particularly, each compound of Example 29, Example 30, Example 33, Example 46, Example 49, Example 59, Example 224, Example 142, Example 98, Example 141, Example 144, Example 219 and Example 222 showed a suppressive effect almost of the same level as or not less than that by ZK158252.

On the other hand, a suppressive effect of the above-mentioned compounds on the increase in the intracellular calcium ion concentration due to stimulation of CHO cell, into which BLT1 had been introduced, by LTB4 was weak as compared to the effect on BLT2, thereby suggesting that the compound of the present invention has a suppressive effect more specific to BLT 2.

The structural formulas of Example compounds of the present invention are as shown in the following Tables.

| Example No. | Structural formula |
|---|---|
| 1 | 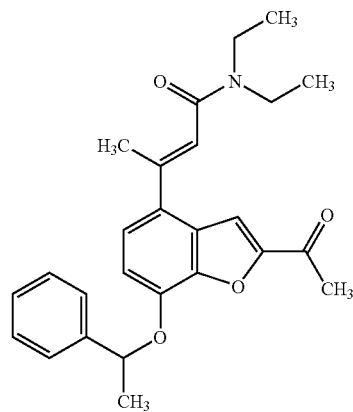 |
| 2 | 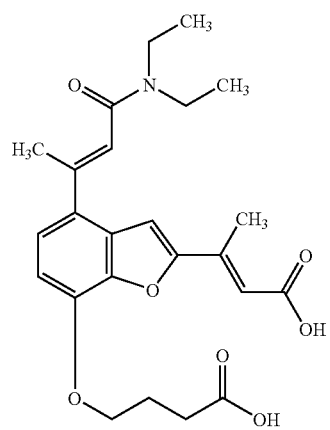 |
| 3 | 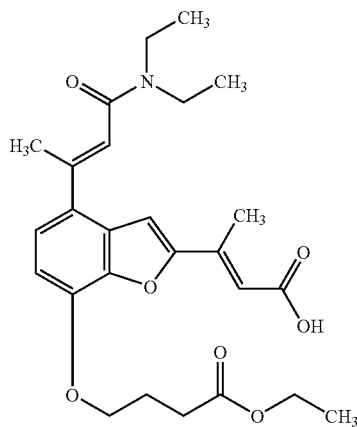 |

4
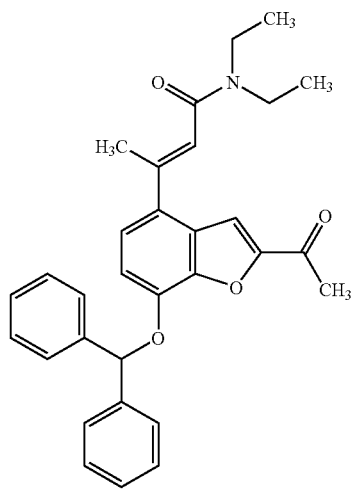
5
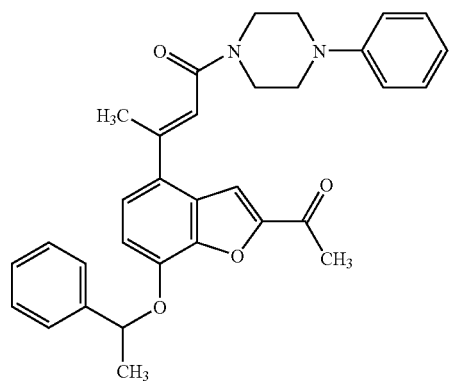
6
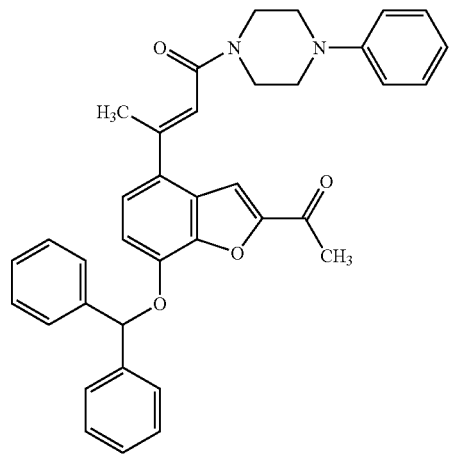

-continued
7 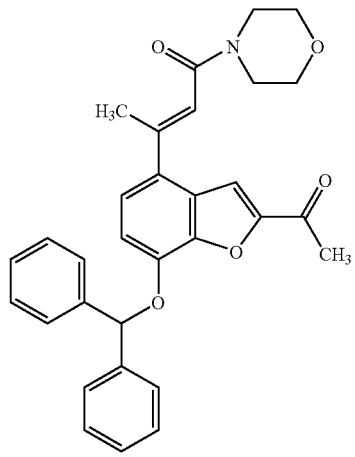
8 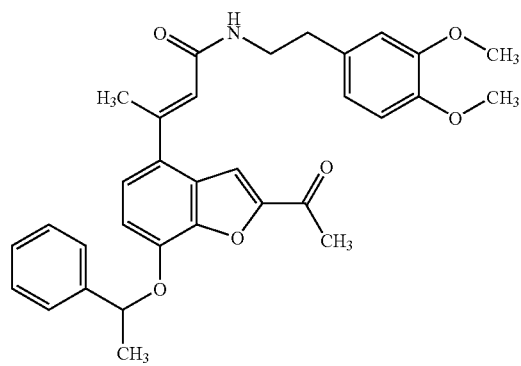
9 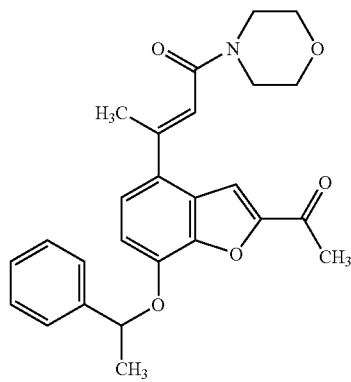
10 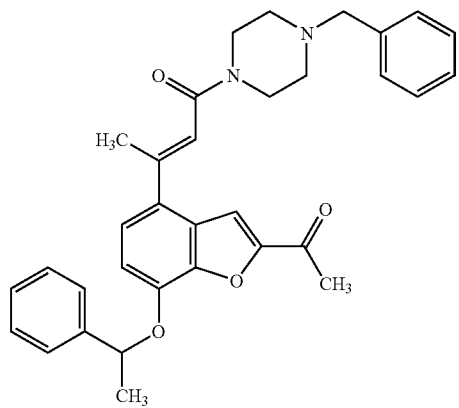

11
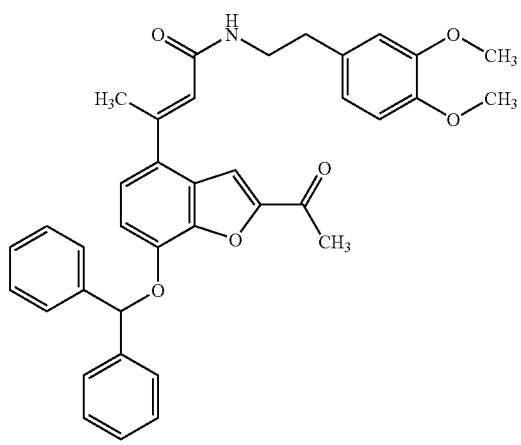
12
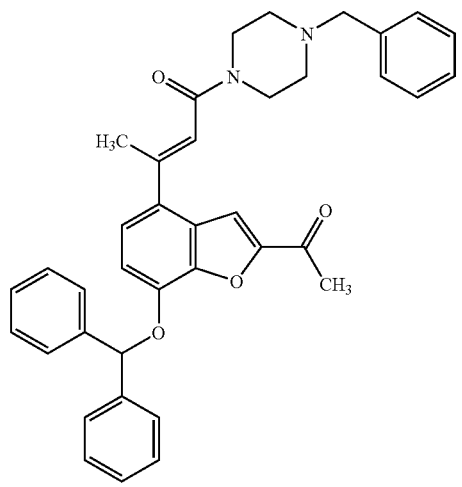
13
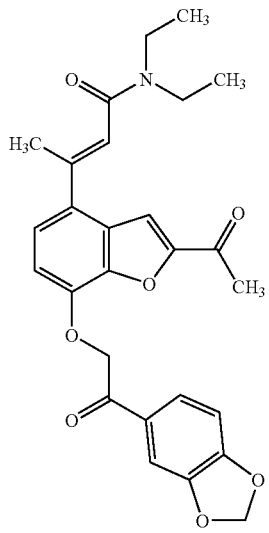

-continued
14 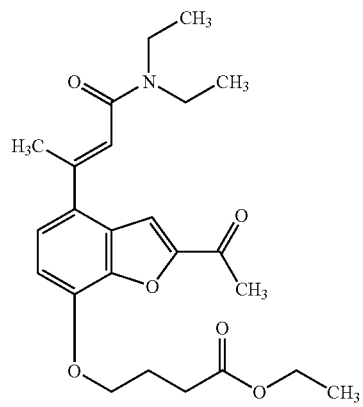
15 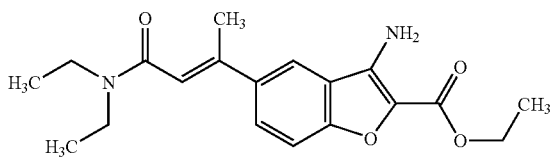
16 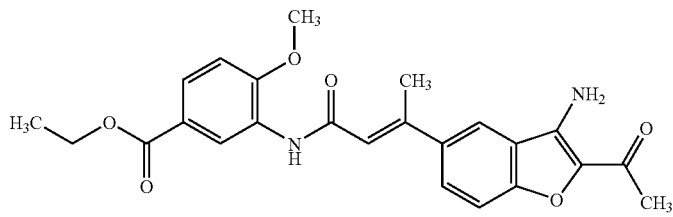
17 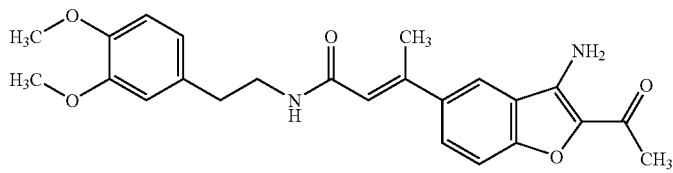
18 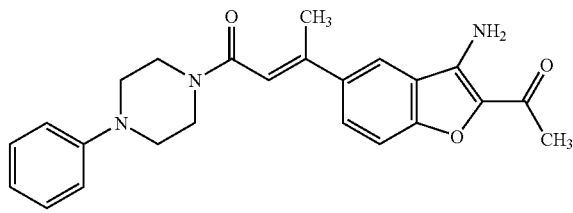
19 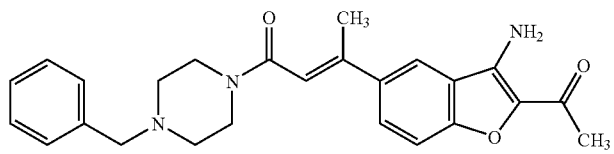

-continued
20 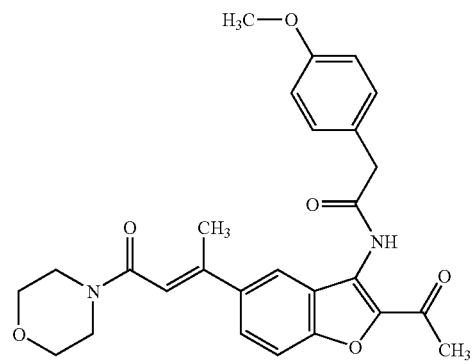
21 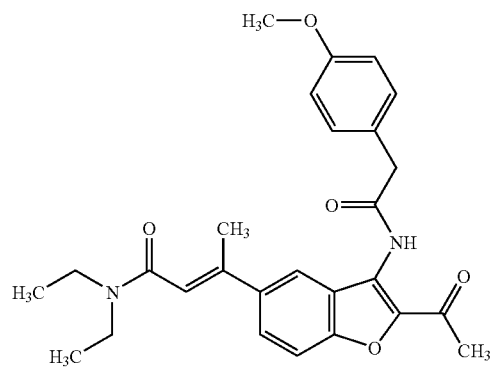
22 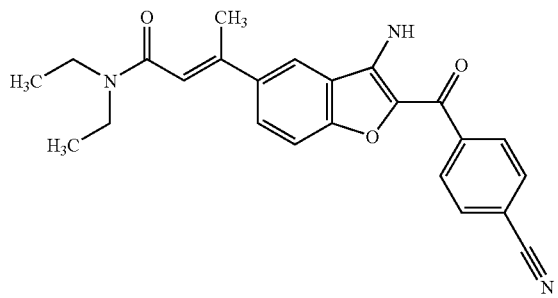
23 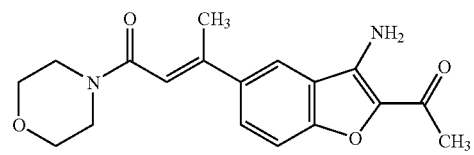
24 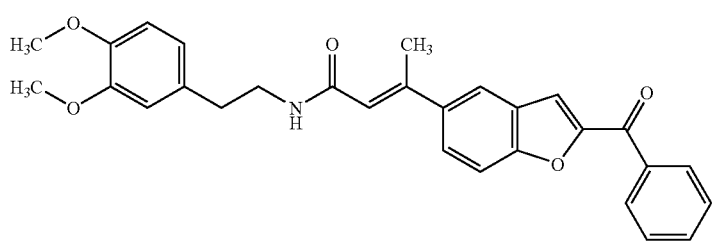

-continued
25 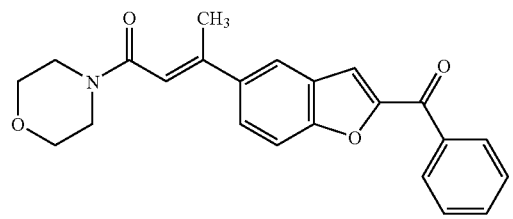
26 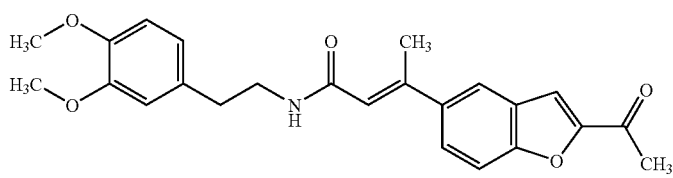
27 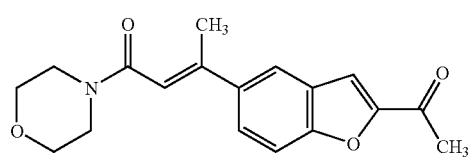
28 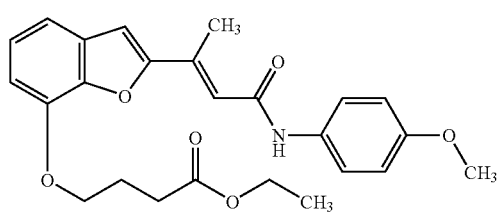
29 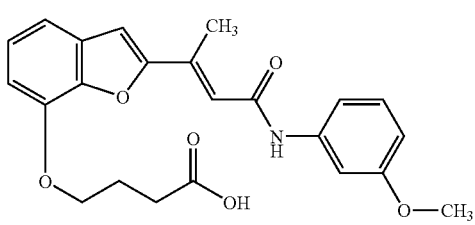
30 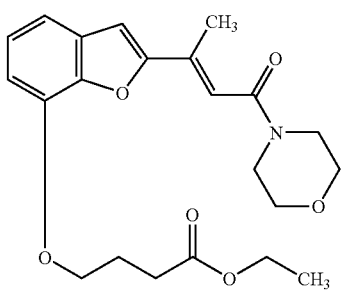
31 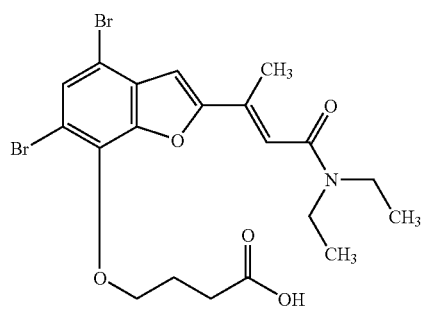

-continued
| | |
|---|---|
| 32 | 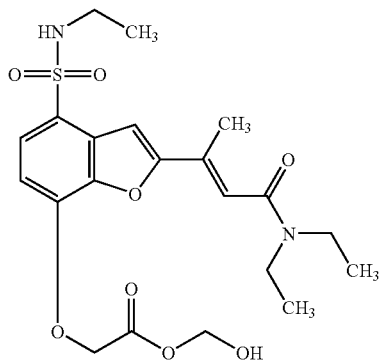 |
| 33 | 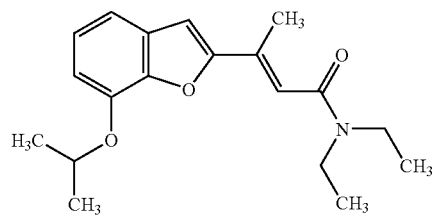 |
| 34 | 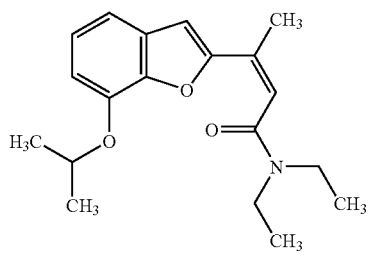 |
| 35 | 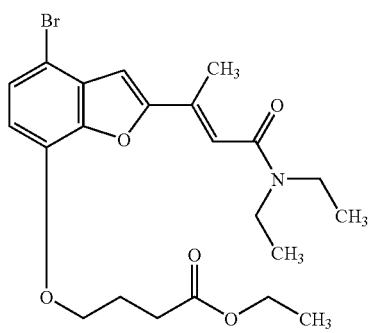 |
| 36 | 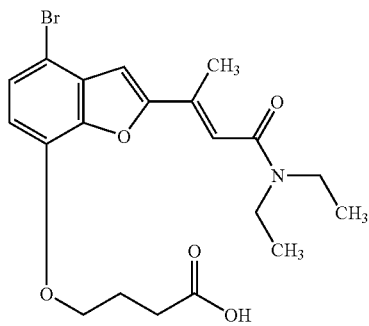 |

-continued
| | |
|---|---|
| 37 | 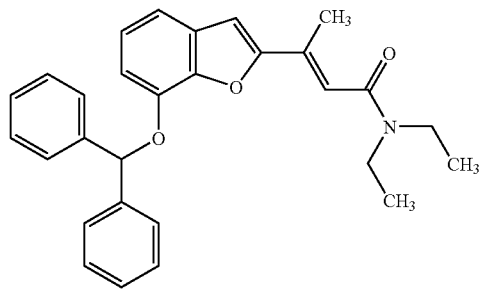 |
| 38 | 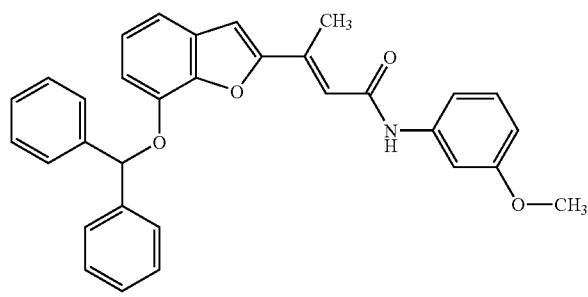 |
| 39 | 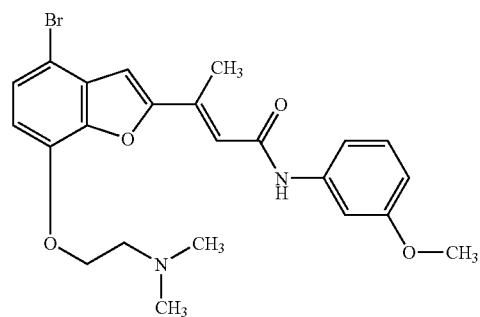 |
| 40 | 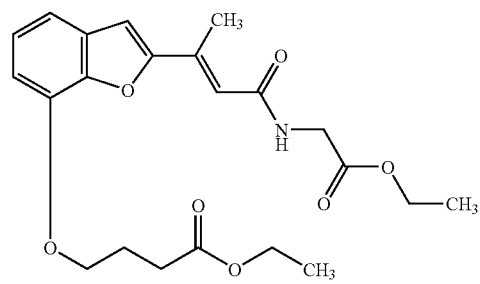 |
| 41 | 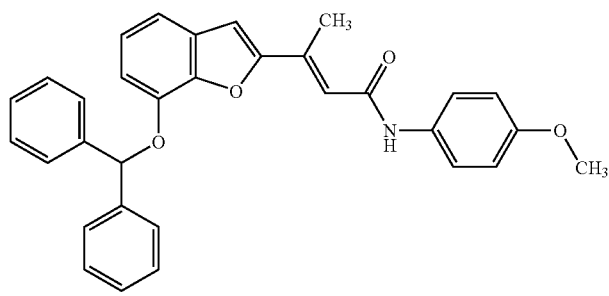 |

-continued
42 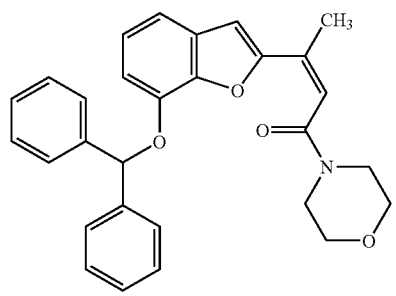
43 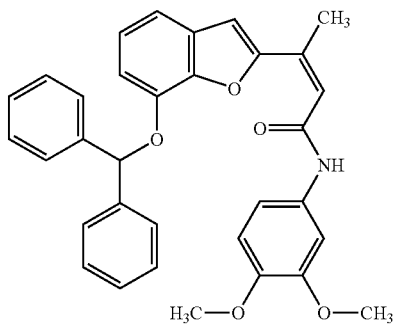
44 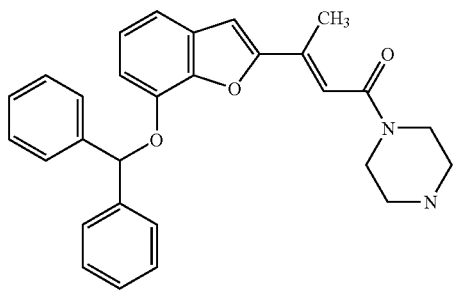
45 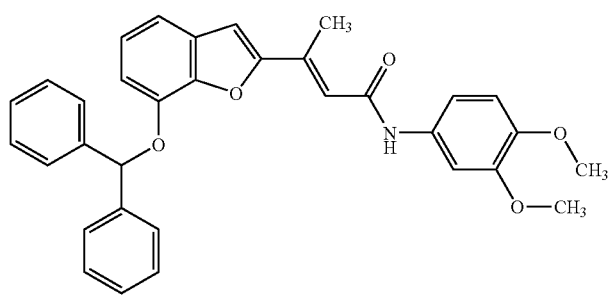
46 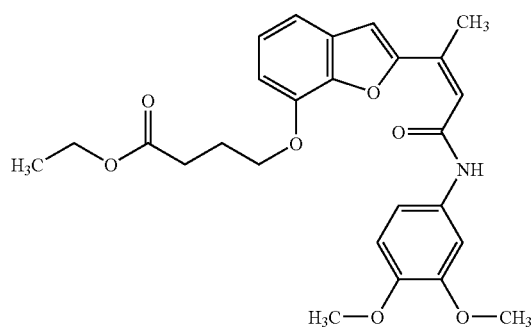

-continued
47 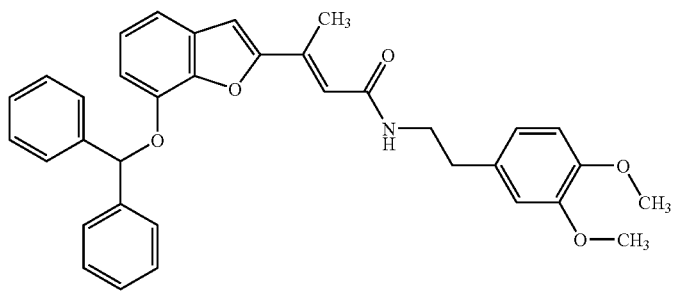
48 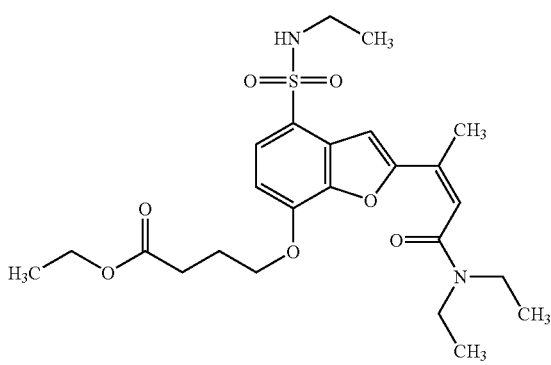
49 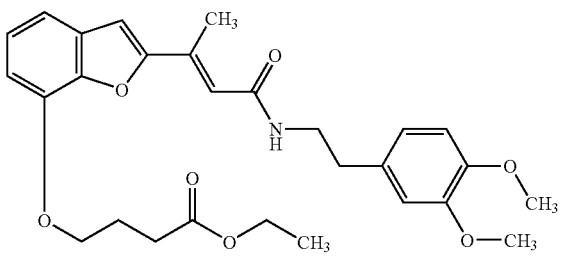
50 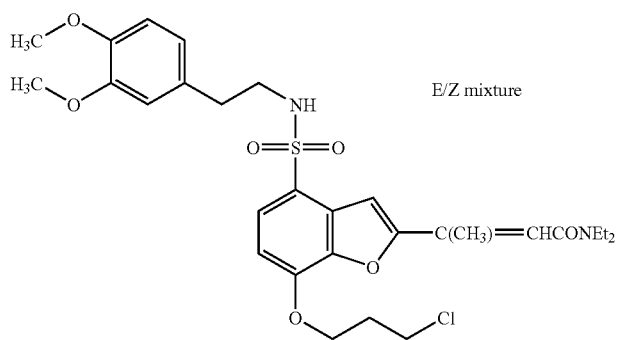
E/Z mixture 51 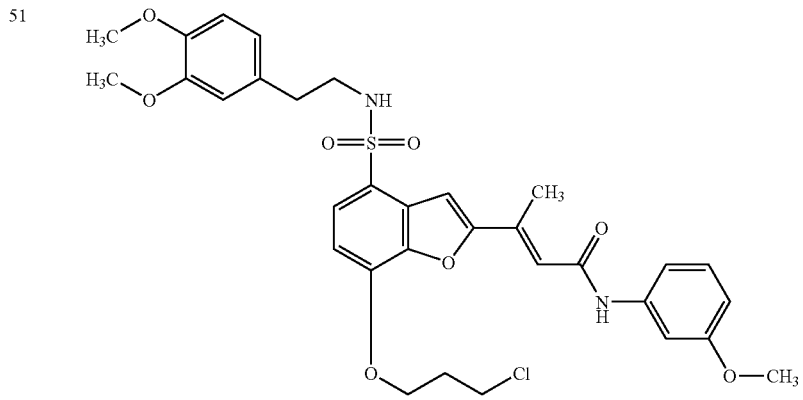
52 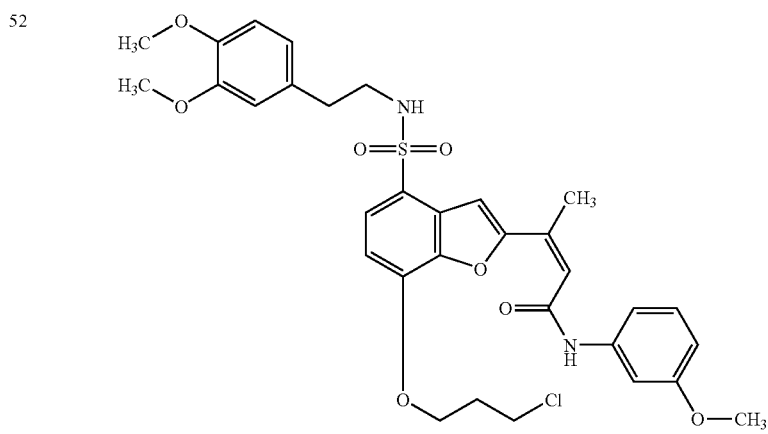
53 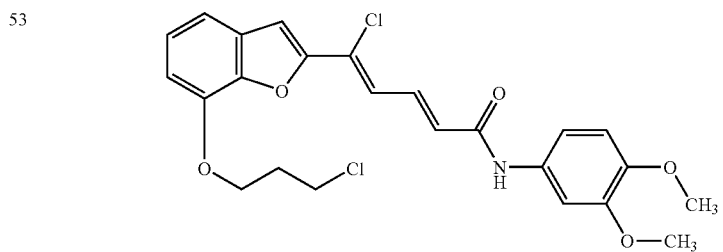
54 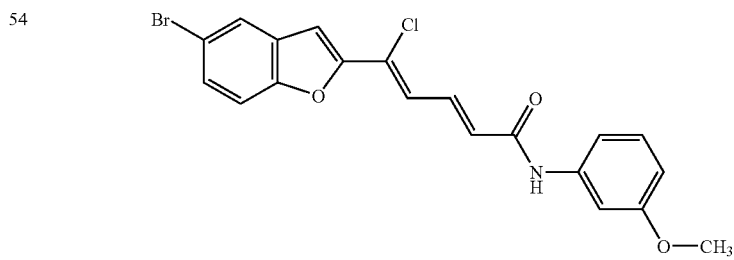

-continued
| | |
|---|---|
| 55 | 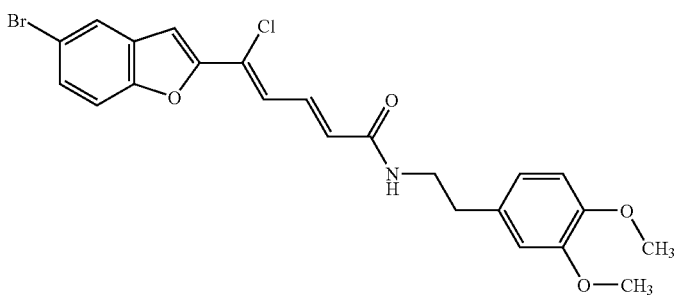 |
| 56 | 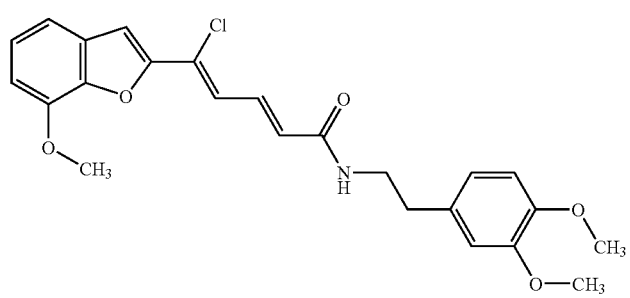 |
| 57 | 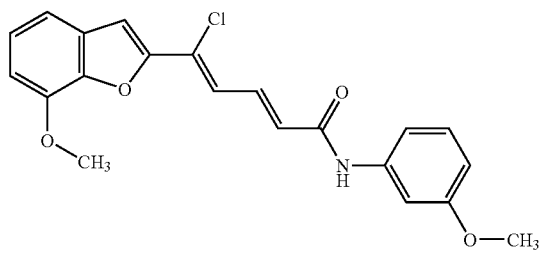 |
| 58 | 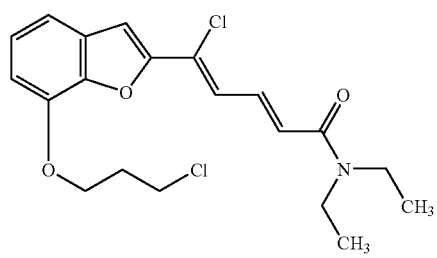 |
| 59 | 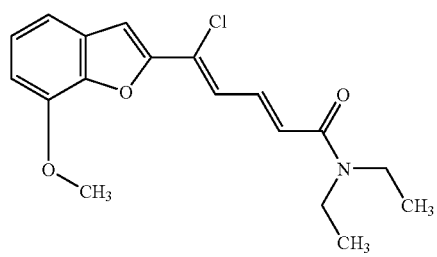 |

-continued
60 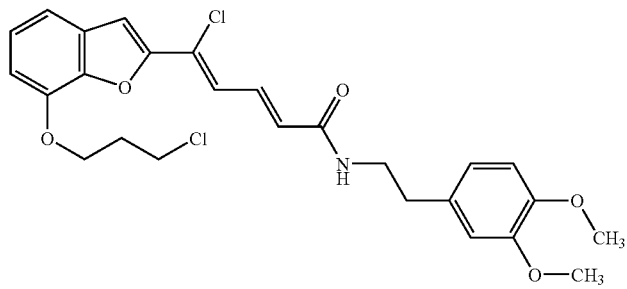
61 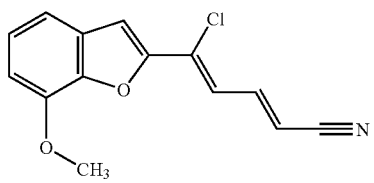
62 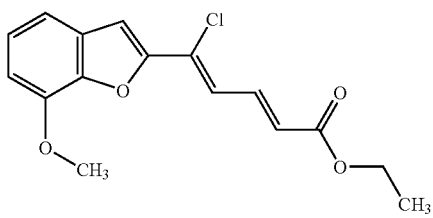
63 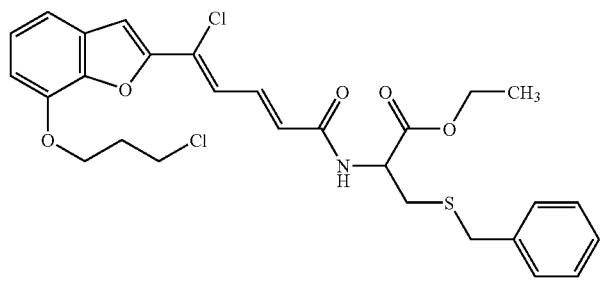
64 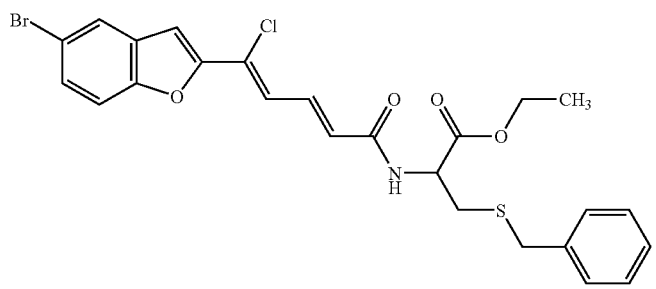
65 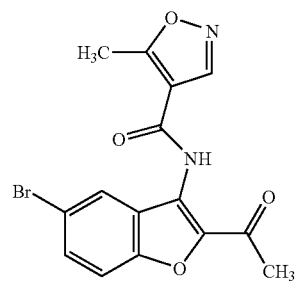

-continued
| | |
|---|---|
| 66 | 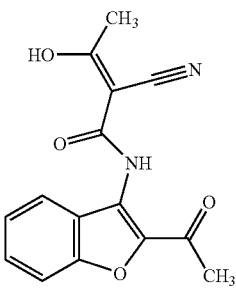 |
| 67 | 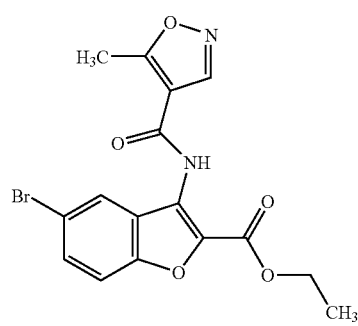 |
| 68 | 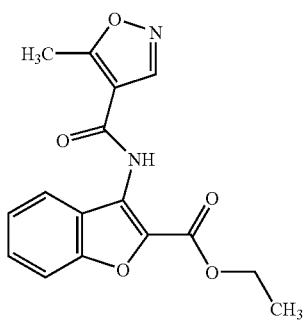 |
| 69 | 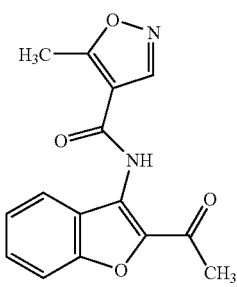 |
| 70 | 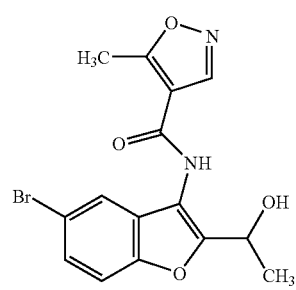 |

-continued
71 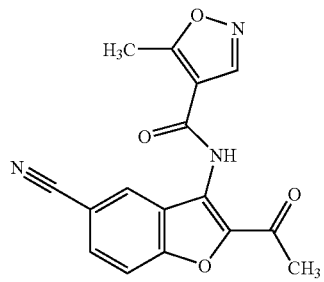
72 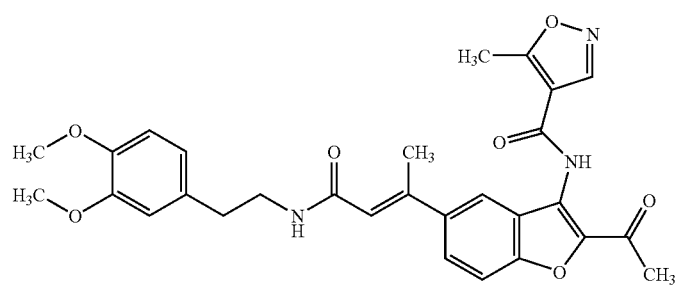
73 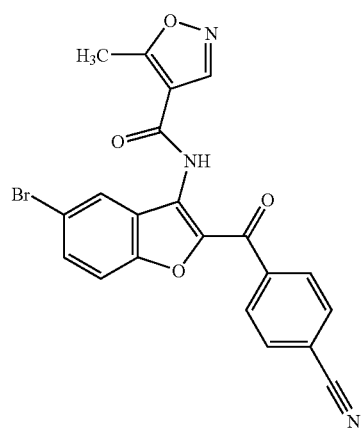
74 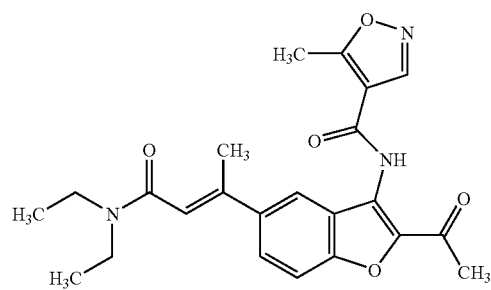

75 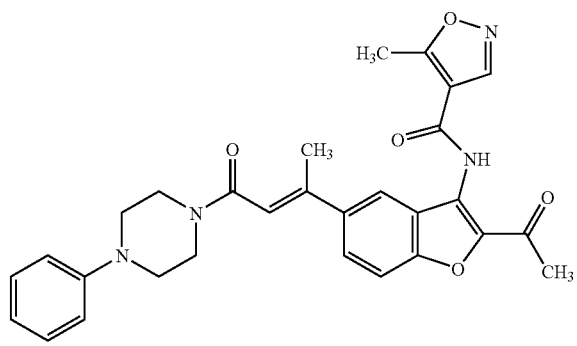
76 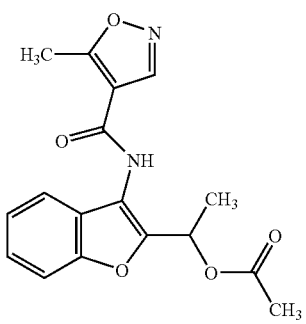
77 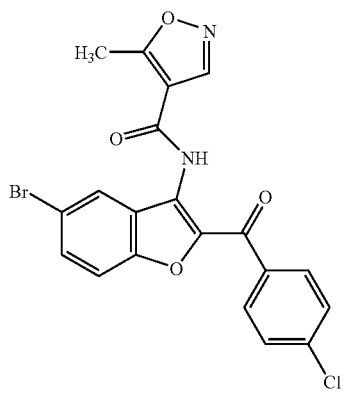
78 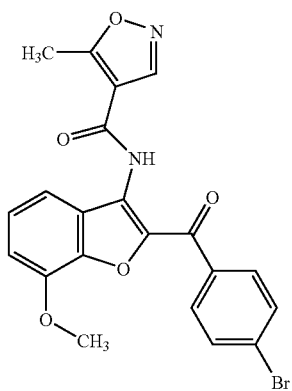

-continued
79
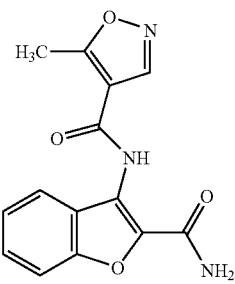
80
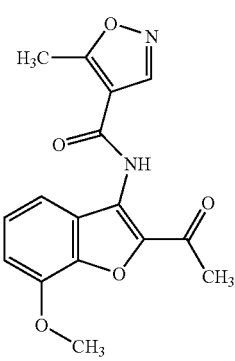
81
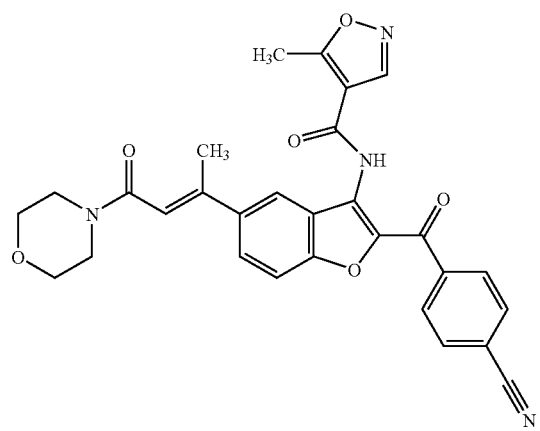
82
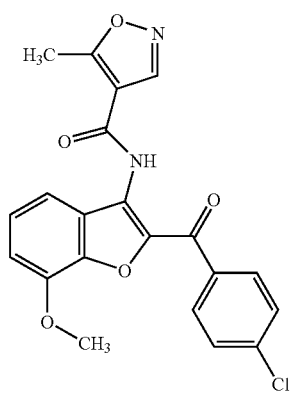

-continued
83
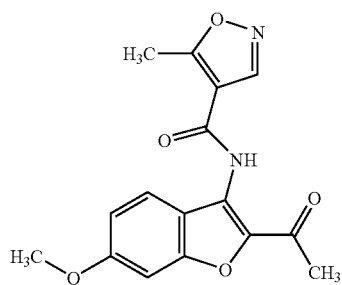
84
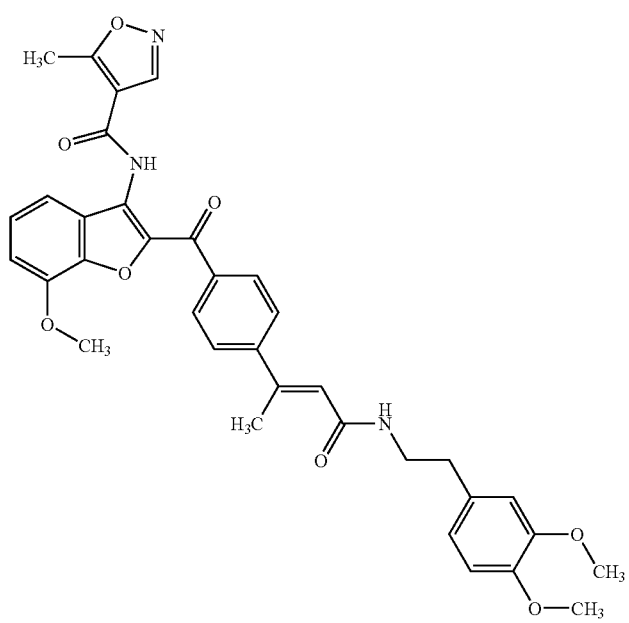
85
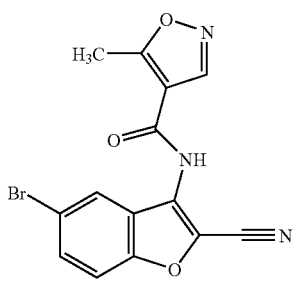
86
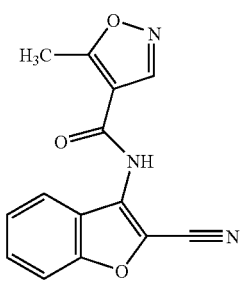

87 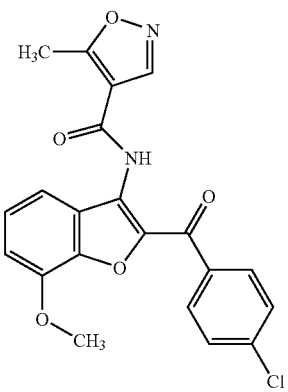
88 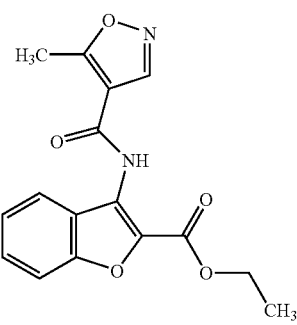
89 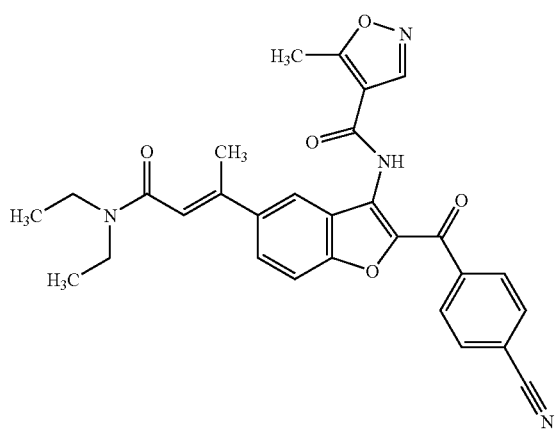
90 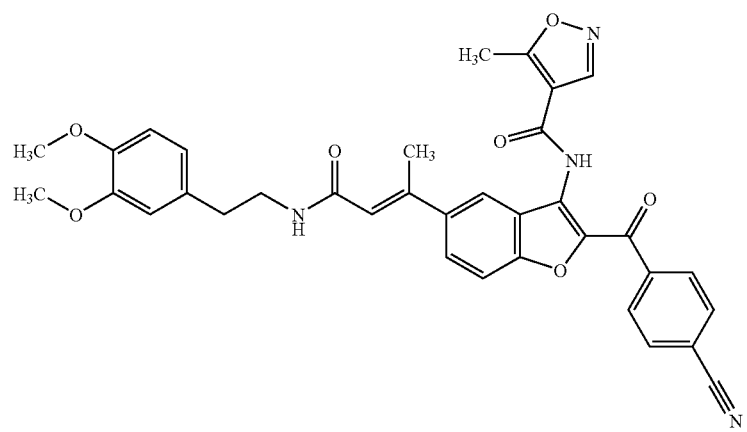

-continued
| | |
|---|---|
| 91 | 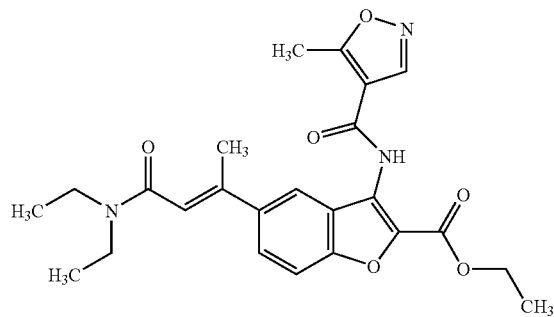 |
| 92 | 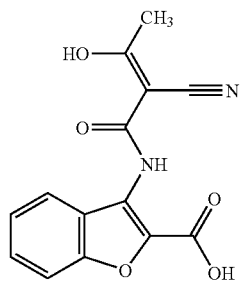 |
| 93 | 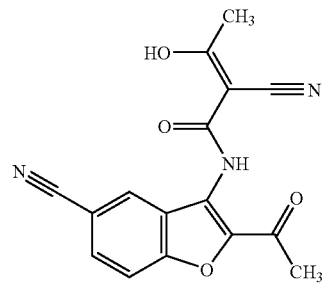 |
| 94 | 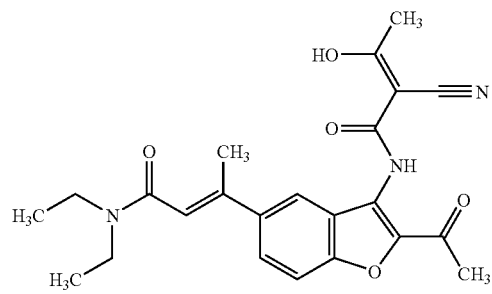 |

-continued
95
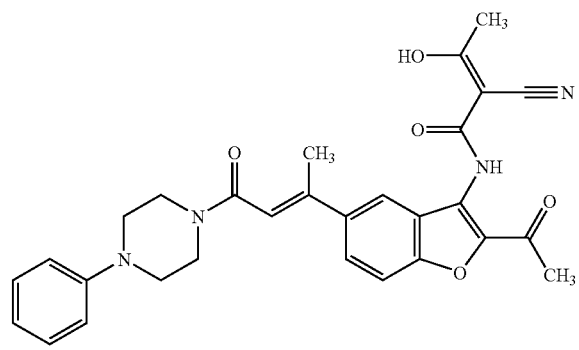
96
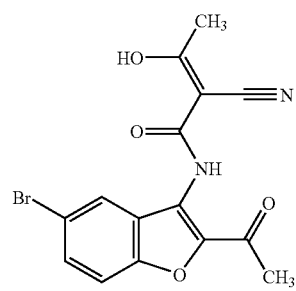
97
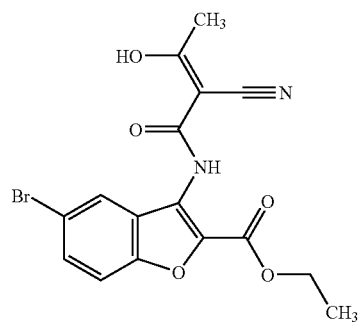
98
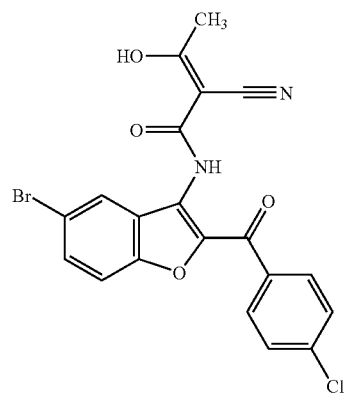

-continued
99
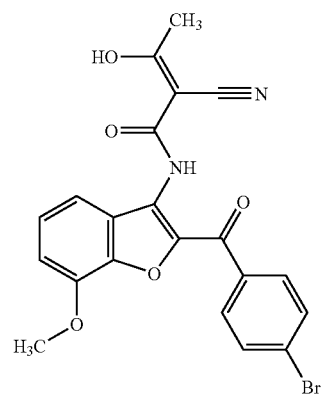
100
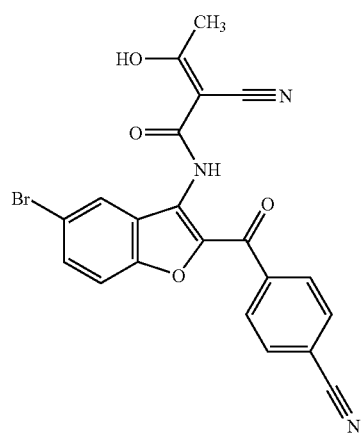
101
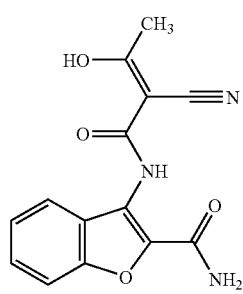
102
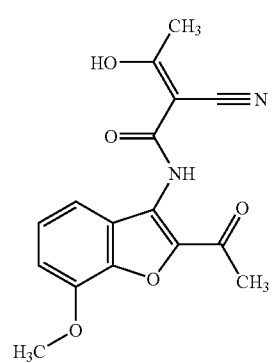

103
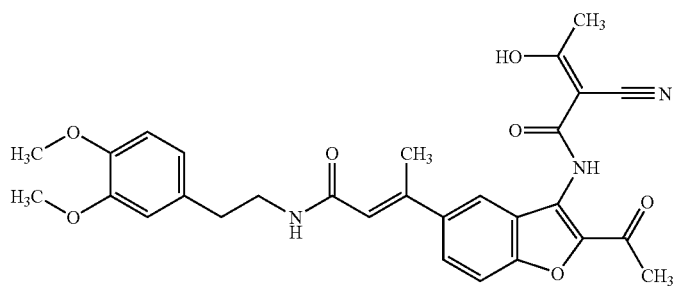
104
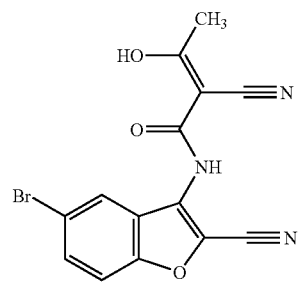
105
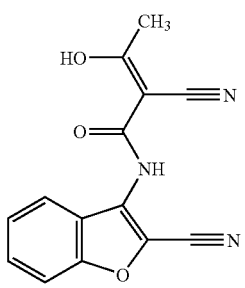
106
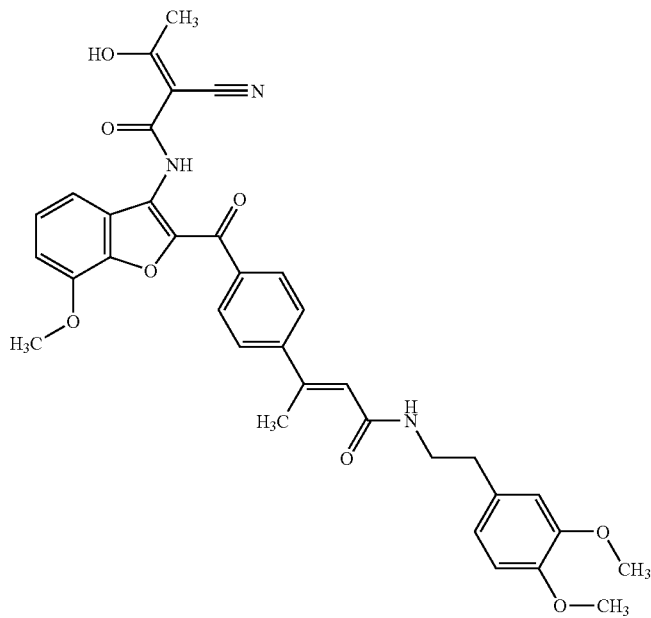

-continued
107
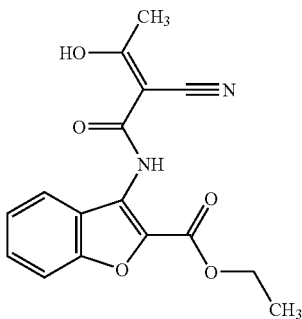
108
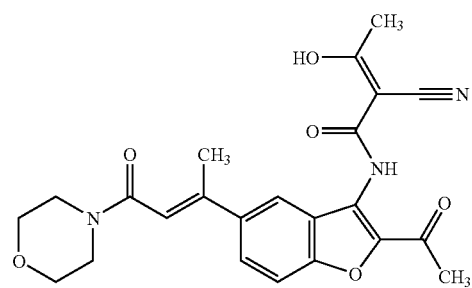
109
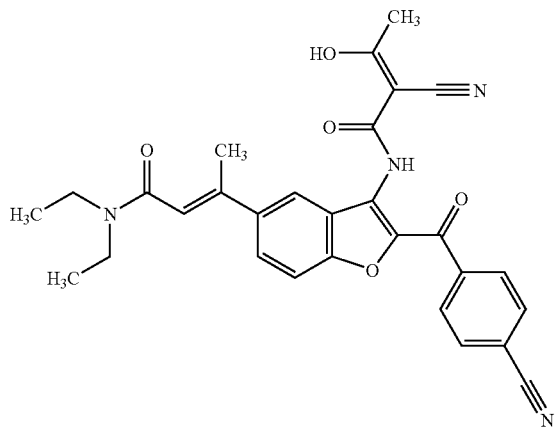
110
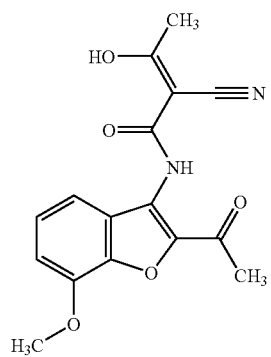

-continued
| | |
|---|---|
| 111 | 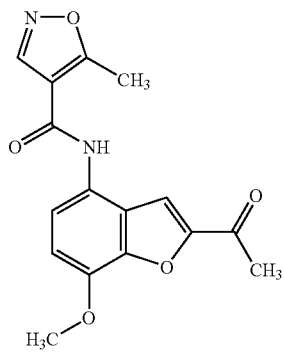 |
| 112 | 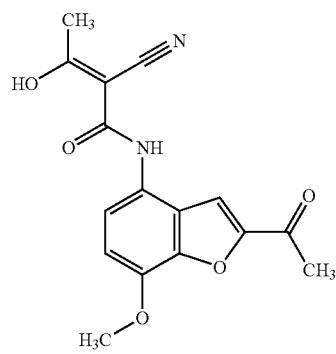 |
| 113 | 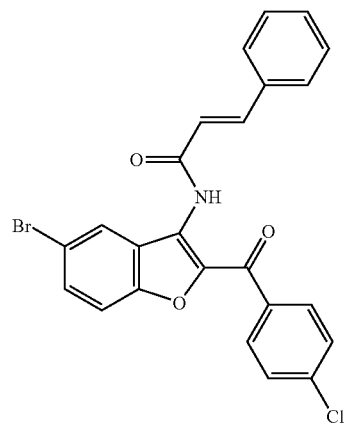 |
| 114 | 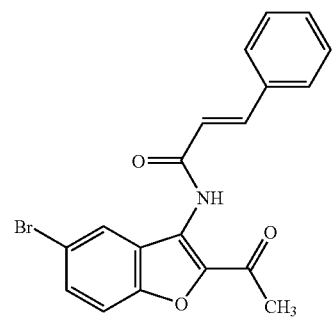 |

-continued
115 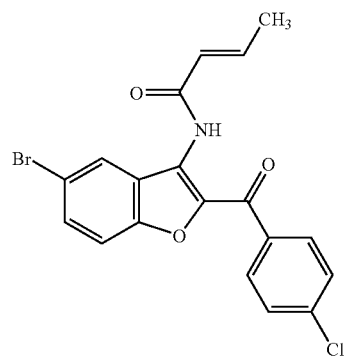
116 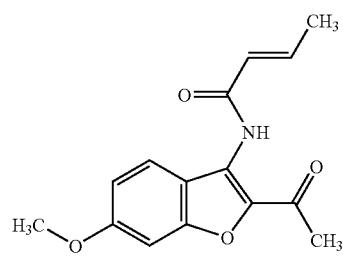
117 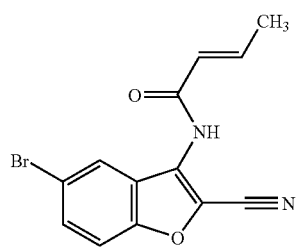
118 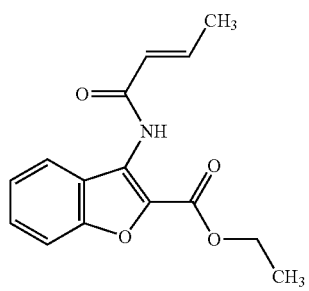
119 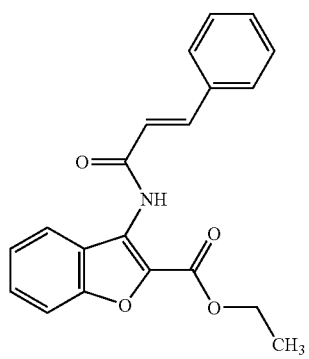

-continued
120 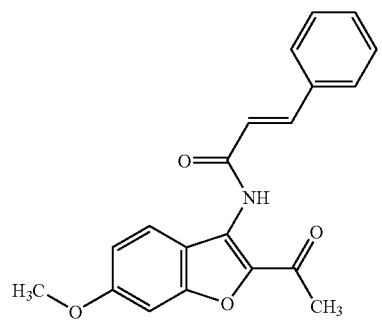
121 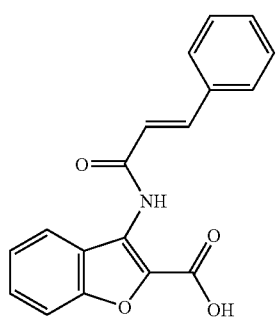
122 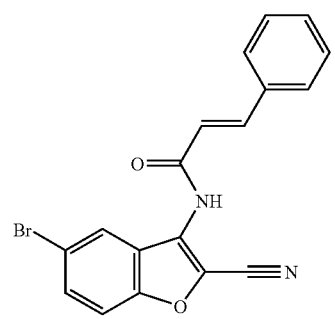
123 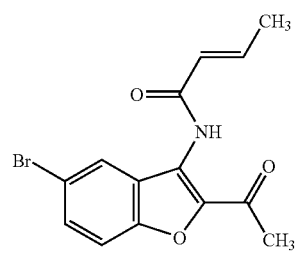
124 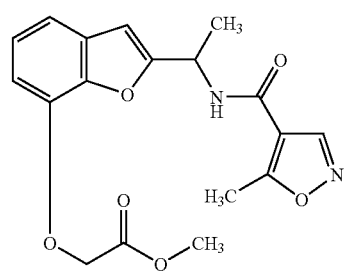

125 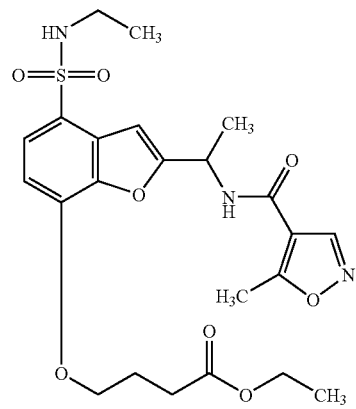
126 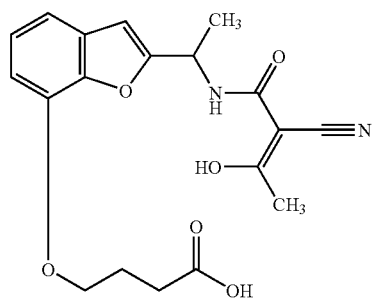
127 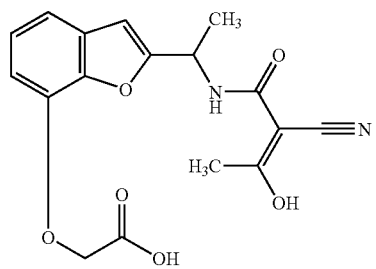
128 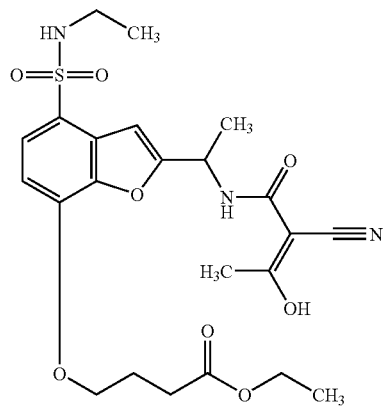

-continued
| | |
|---|---|
| 129 | 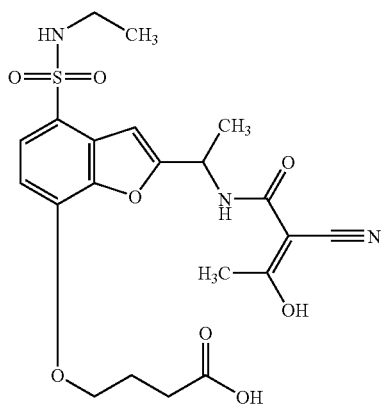 |
| 130 | 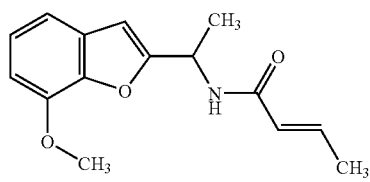 |
| 131 | 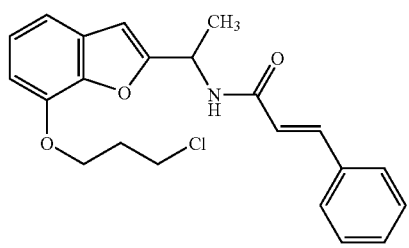 |
| 132 | 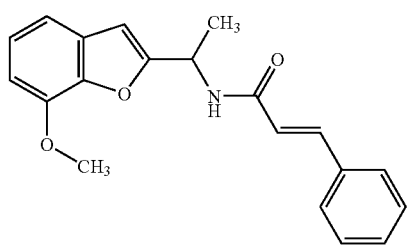 |
| 133 | 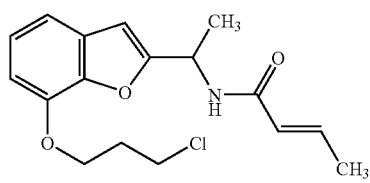 |
| 134 | 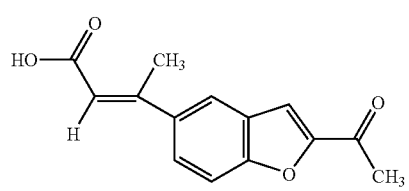 |

-continued
135 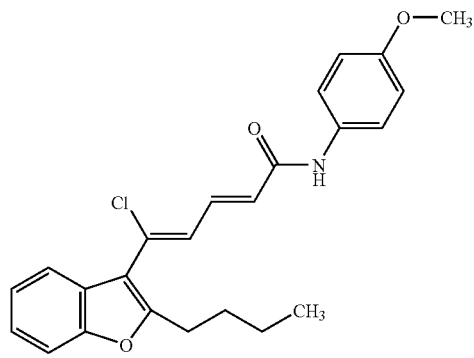
136 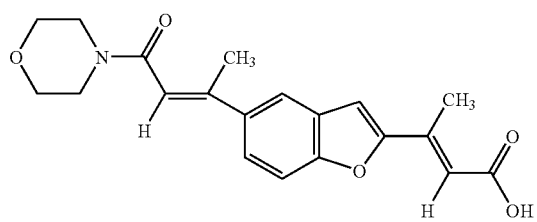
137 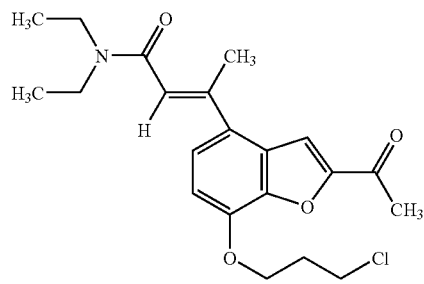
138 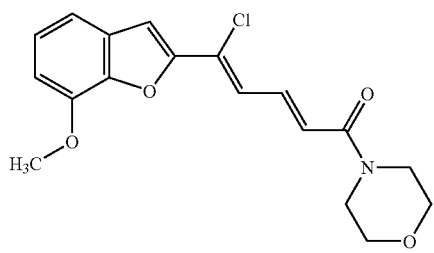
139 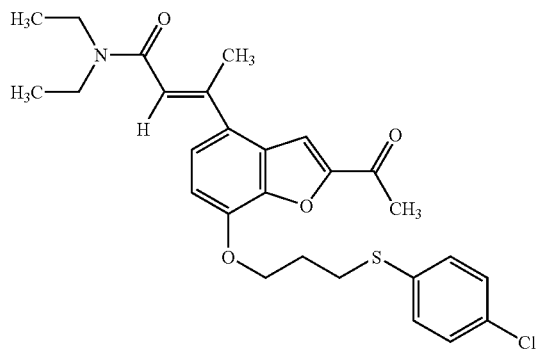

-continued
140 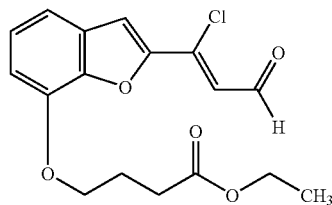
141 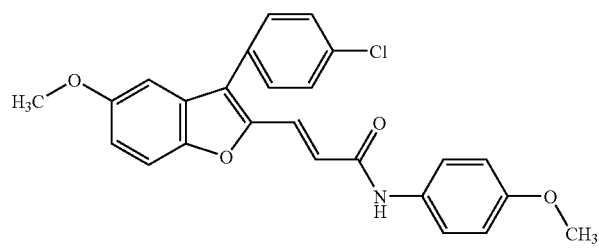
142 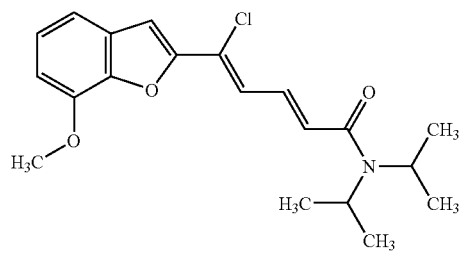
143 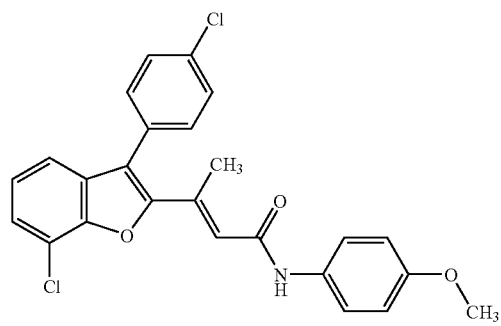
144 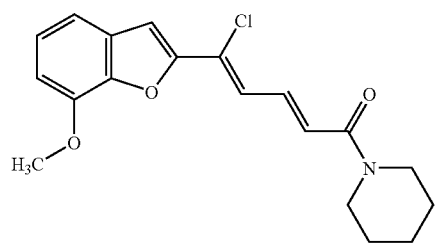

-continued
145 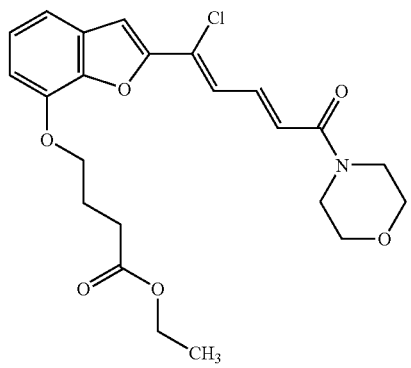
146 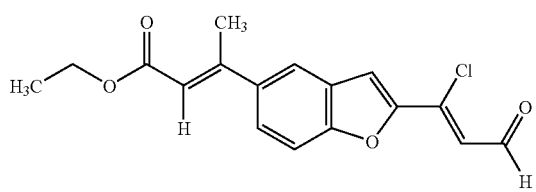
147 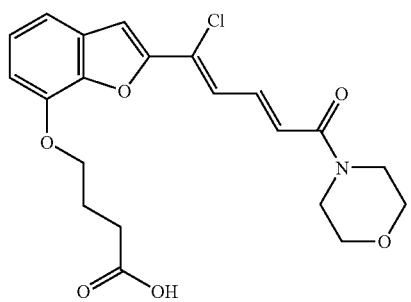
148 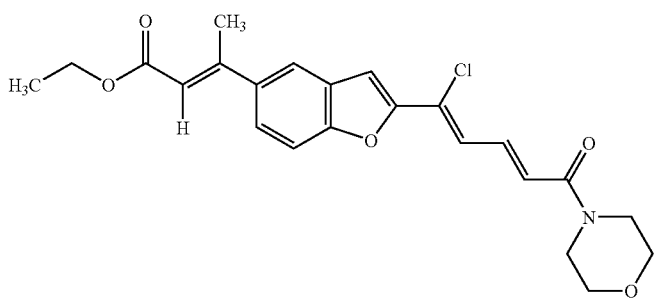
149 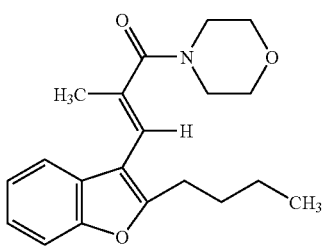
151 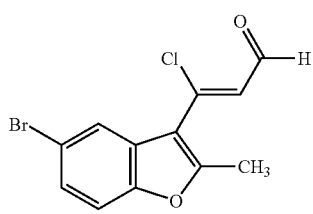

-continued
| | |
|---|---|
| 152 | 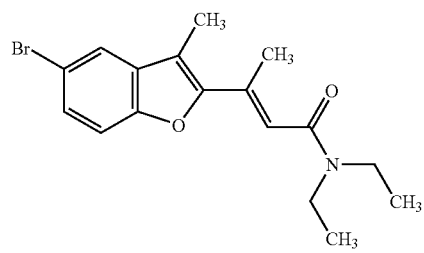 |
| 153 | 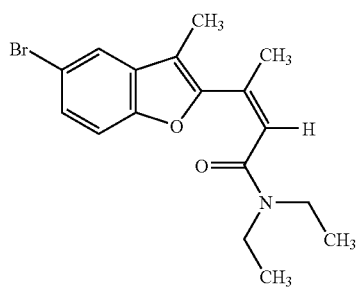 |
| 154 | 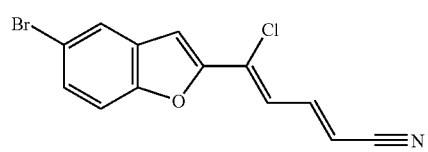 |
| 155 | 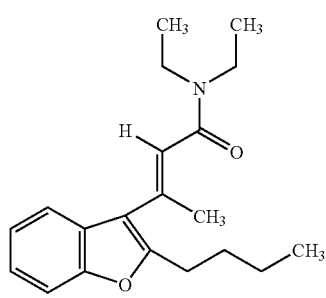 |
| 157 | 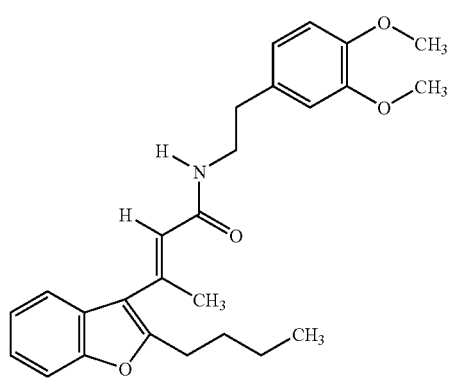 |
| 158 | 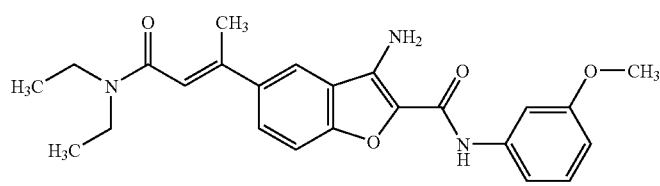 |

-continued
| 159 | 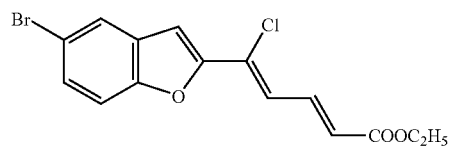 |
| --- | --- |
| 160 | 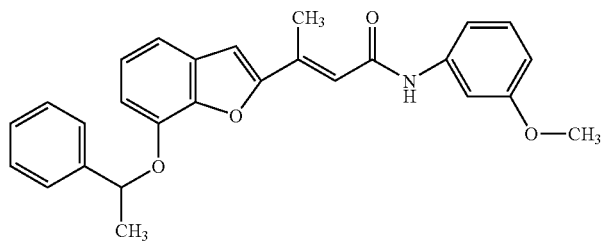 |
| 161 | 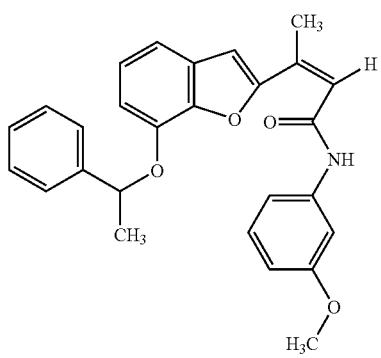 |
| 162 | 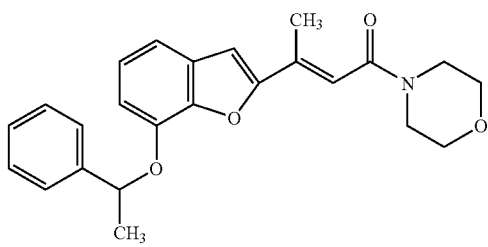 |
| 163 | 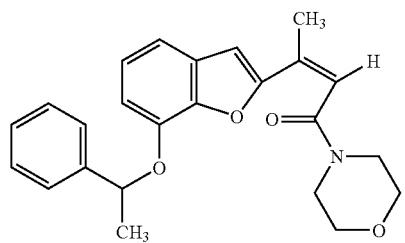 |
| 164 | 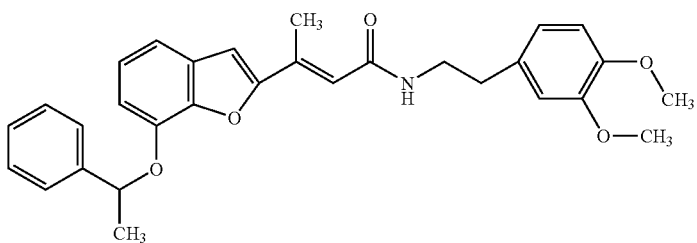 |

-continued
| | |
|---|---|
| 165 | 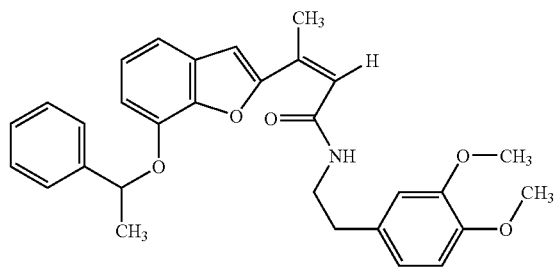 |
| 166 | 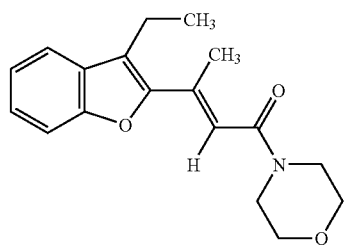 |
| 167 | 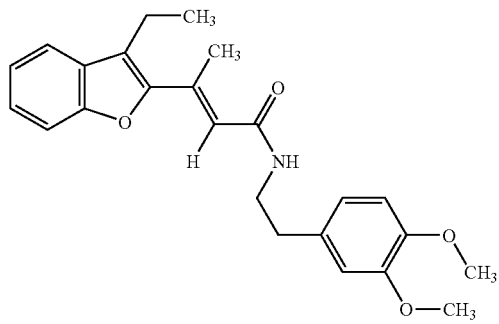 |
| 169 | 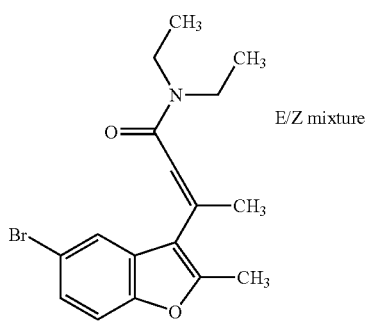 E/Z mixture |
| 170 | 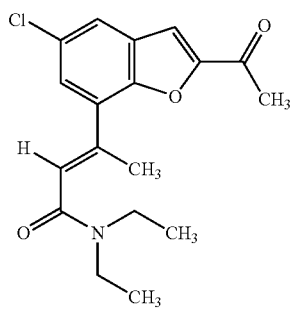 |

-continued
171 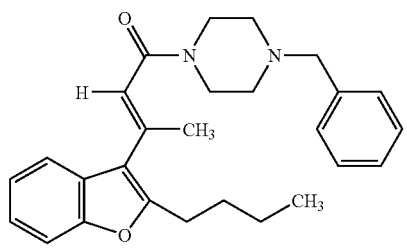
172 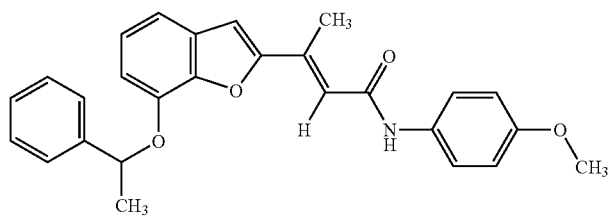
173 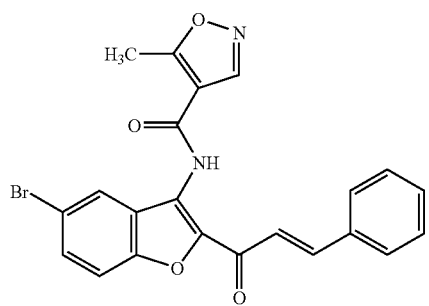
174 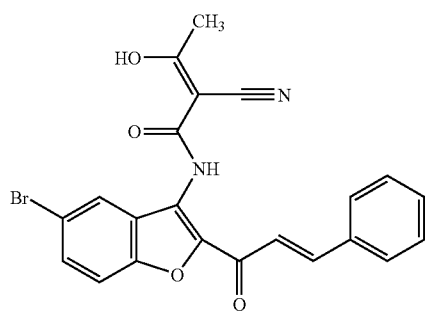
175 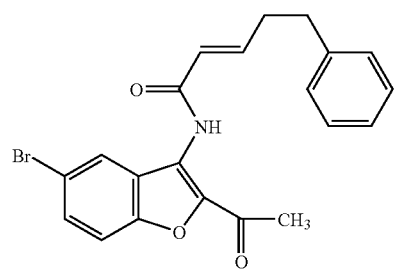

-continued
176 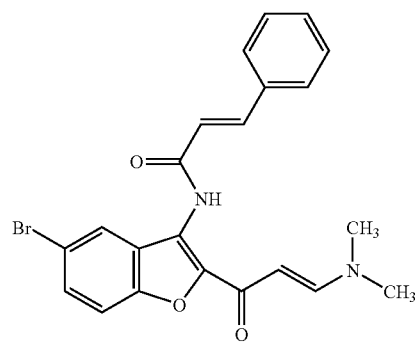
177 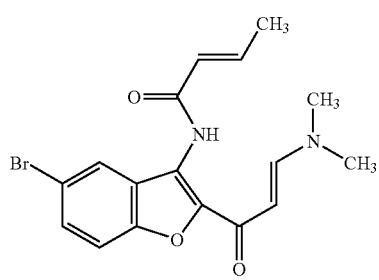
178 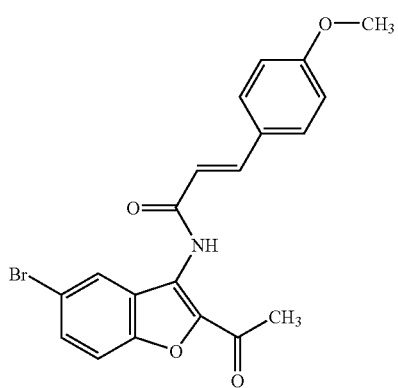
179 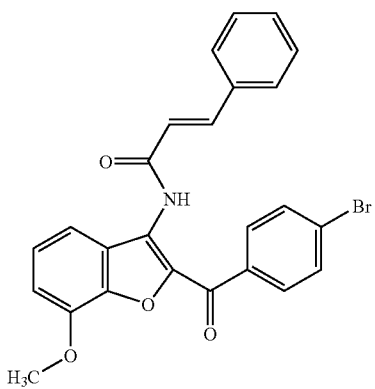

-continued
180
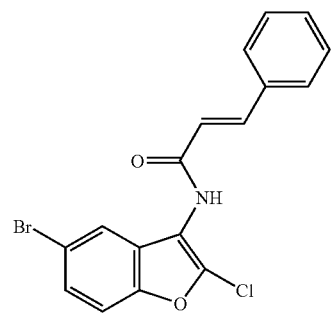
181
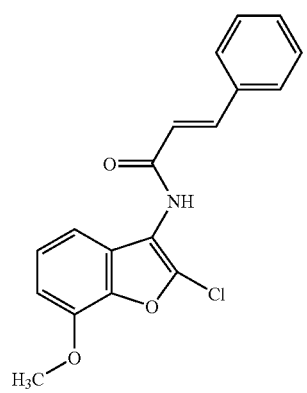
182
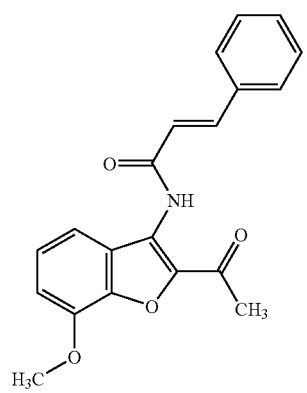
183
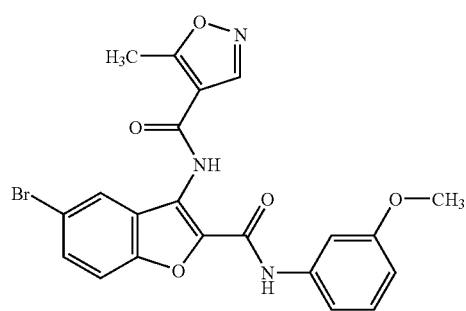

-continued
184 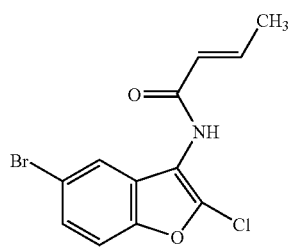
185 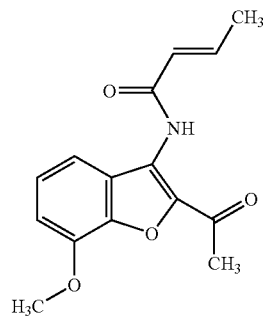
186 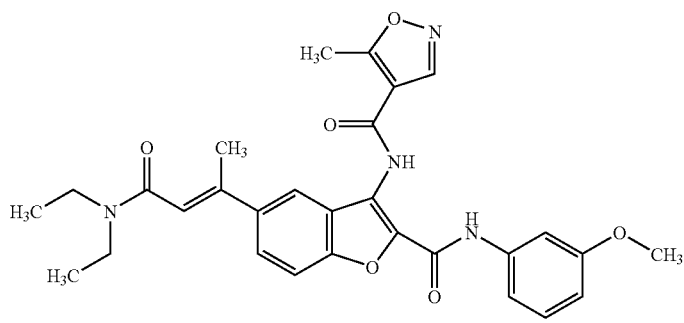
187 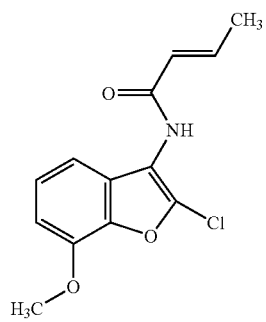
188 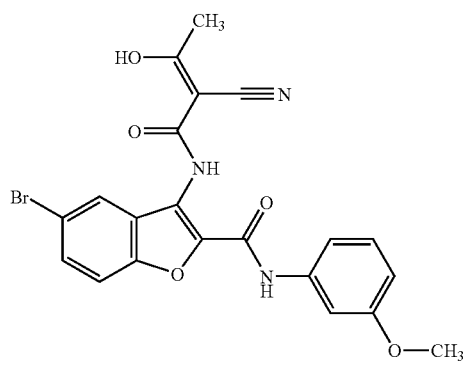

-continued
189 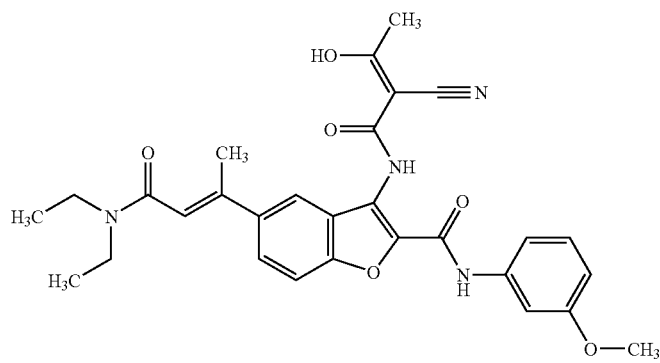
190 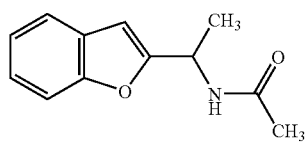
191 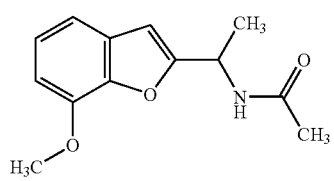
192 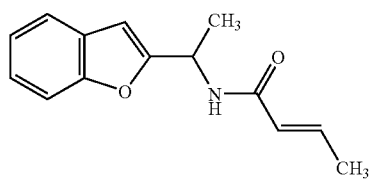
193 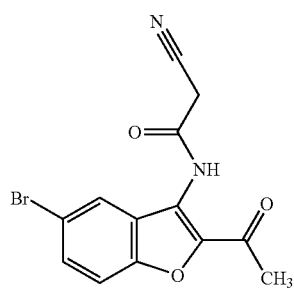
194 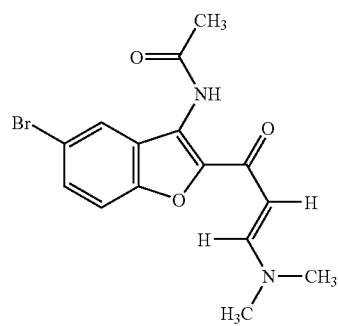

-continued
195
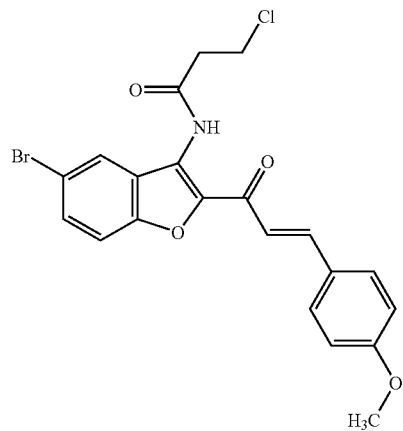
196
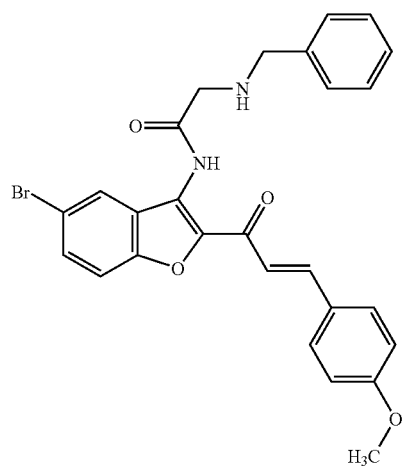
197
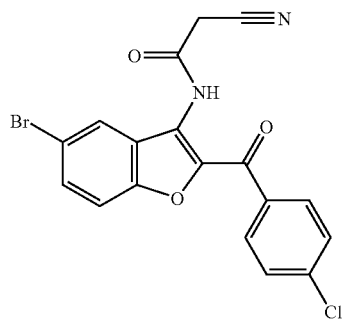
198
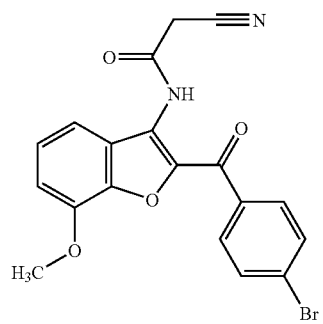

-continued
199
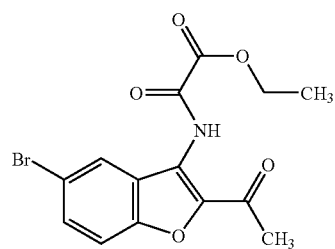
200
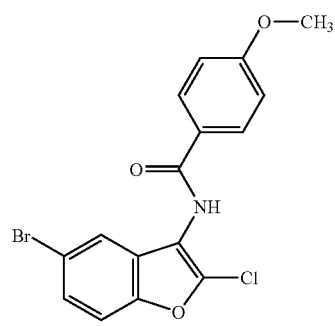
201
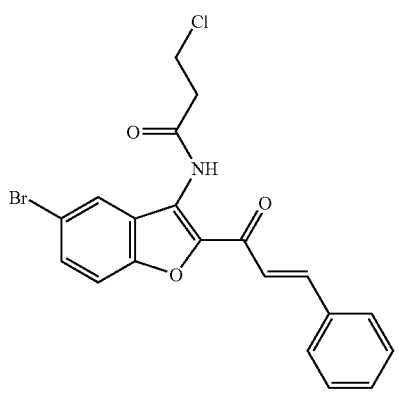
202
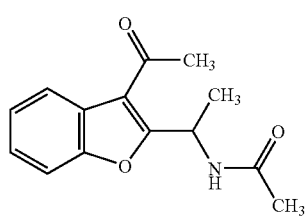

-continued
203 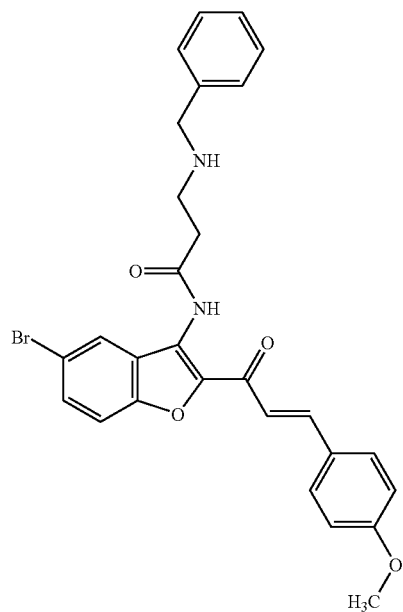
204 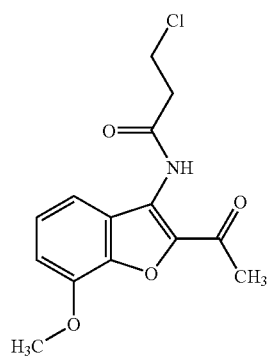
205 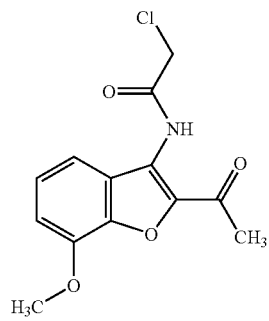

-continued
207
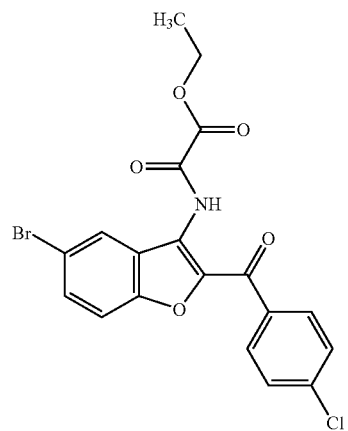
208
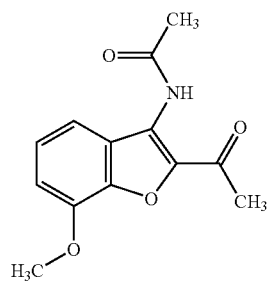
209
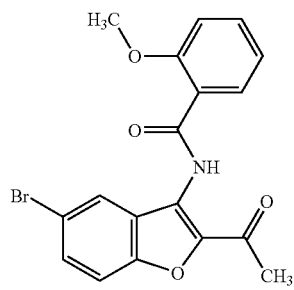
210
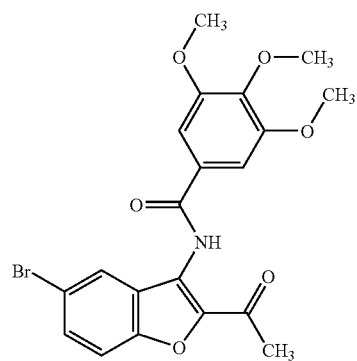

-continued
211 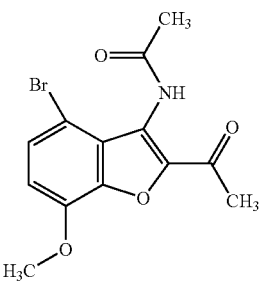
212 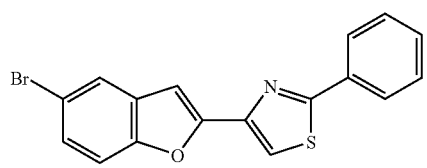
213 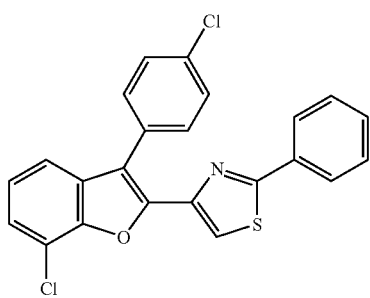
214 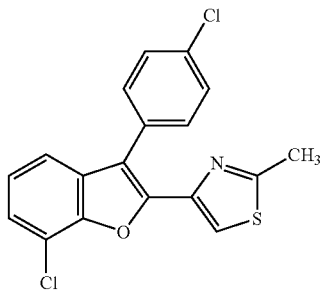
215 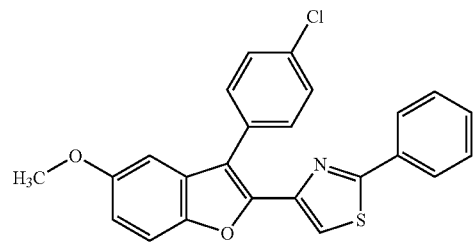
216 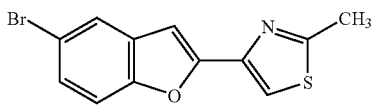

-continued
217 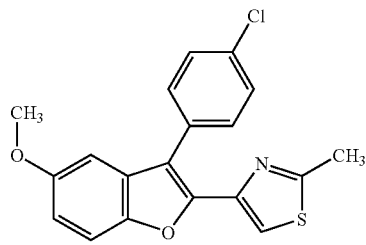
218 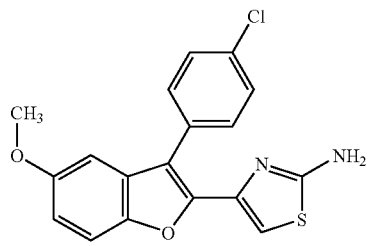
219 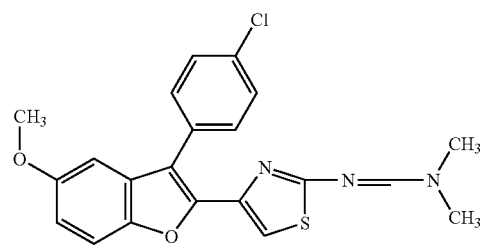
220 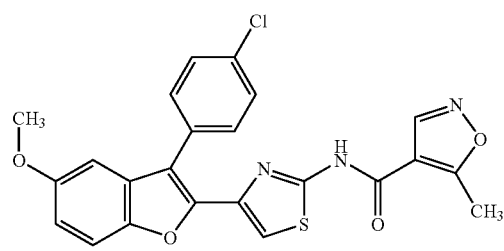
221 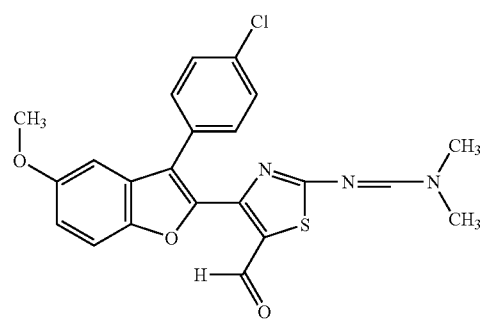
222 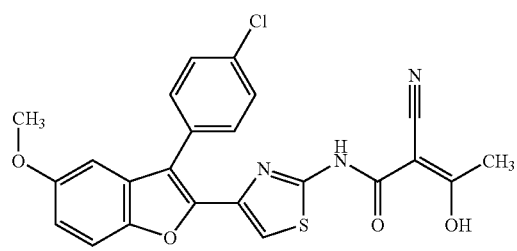

| 223 | 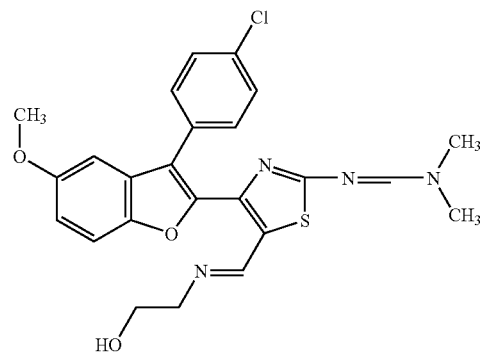 |
| --- | --- |
| 224 | 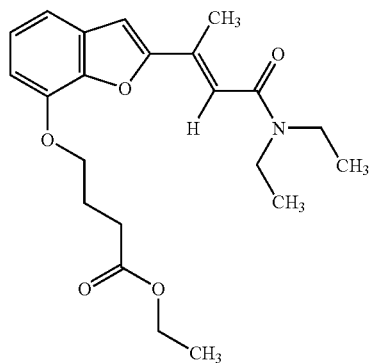 |
| 225 | 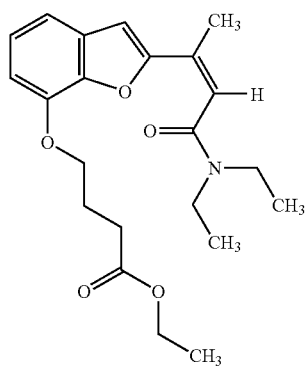 |
| 226 | 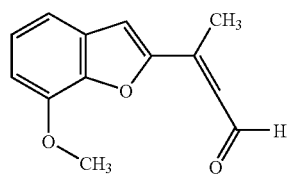 |

227 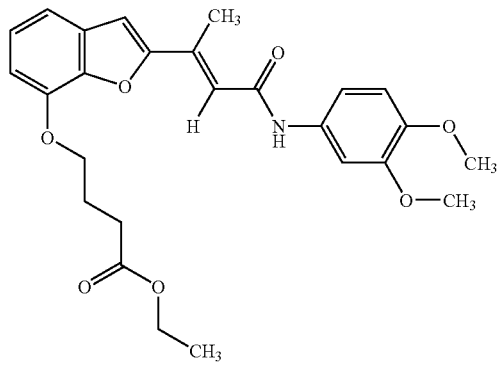

INDUSTRIAL APPLICABILITY

The benzofuran compound of the present invention and a pharmaceutically acceptable salt thereof have superior leukotriene inhibitory action, BLT2 competitive inhibitory action, BLT2 blocking action, action for the prophylaxis or treatment of allergy, action for the prophylaxis or treatment of asthma and action for the prophylaxis or treatment of inflammation, and are useful as agents for the prophylaxis or treatment of diseases such as allergic disease, asthma, inflammation and the like, and other diseases.

This application is based on a patent application No. 2003-153563 filed in Japan on May 29, 2003, the contents of which are hereby incorporated by reference.

The invention claimed is:

1. A compound represented by the formula (I) having a benzofuran ring:

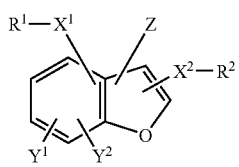

wherein

Z is a group selected from the following formulas $Z^b$ and $Z^d$

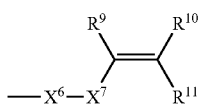 $Z^b$

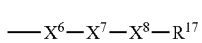 $Z^d$ wherein
$X^6$ is

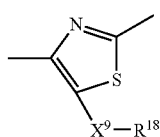

wherein $R^{18}$ is a hydrogen atom, a hydroxyl group, —CHO, —COOAlk or a $C_{1-6}$ alkyl group (the alkyl group is optionally substituted by one or more hydroxyl groups), and $X^9$ is a bond, —CH=N— or —CO—NH—;

$X^7$ is a bond, —HN—CO— or —N=CH—;

$R^9$ is a hydrogen atom or a cyano group;

$R^{10}$ is a hydrogen atom, a hydroxyl group, a $C_{1-6}$ alkyl group, a $C_{6-14}$ aryl group (the aryl group is optionally substituted by one or more $C_{1-6}$ alkoxy groups) or a $C_{6-14}$ aryl-$C_{1-6}$ alkyl group, or $R^9$ and $R^{10}$ optionally form, together with the carbon atoms bonded thereto, a heteroaromatic ring, whereby $Z^b$ becomes

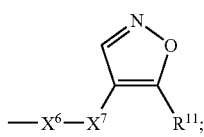

$R^{11}$ is a hydrogen atom, a hydroxyl group, a $C_{1-6}$ alkyl group, a $C_{6-14}$ aryl group (the aryl group is optionally substituted by one or more substituents selected from the group consisting of hydroxyl group and $C_{1-6}$ alkoxy group) or a $C_{6-14}$ aryl-$C_{1-6}$ alkyl group;

$X^8$ is a bond or a $C_{1-6}$ alkylene group; and $R^{17}$ is a hydrogen atom, a $C_{1-6}$ alkyl group, a $C_{6-14}$ aryl group or an amino group (the amino group is optionally mono- or di-substituted by $C_{1-6}$ alkyl group(s));

$X^1$ is a bond or —O—;

$R^1$ is a hydrogen atom, a halogen atom, a $C_{6-14}$ aryl group (the aryl group is optionally substituted by one or more halogen atoms) or a $C_{1-6}$ alkyl group;

$X^2$ is a bond;

$R^2$ is a $C_{6-14}$ aryl group (the aryl group is optionally substituted by one or more halogen atoms); and $Y^1$ and $Y^2$ are the same or different and each is a hydrogen atom, a halogen atom, a hydroxyl group, a $C_{1-6}$ alkoxy group, a $C_{6-14}$ aryl group (the aryl group is optionally substituted by one or more halogen atoms), or a pharmaceutically acceptable salt thereof.

2. A pharmaceutical composition comprising a compound of claim 1 or a pharmaceutically acceptable salt thereof, and a pharmaceutically acceptable carrier.

3. The pharmaceutical composition of claim 2, which is a leukotriene inhibitor.

4. The pharmaceutical composition of claim 2, which is a BLT2 inhibitor.

5. The pharmaceutical composition of claim 2, which is an agent for the treatment of allergy.

6. The pharmaceutical composition of claim 2, which is an agent for the treatment of asthma.

7. The pharmaceutical composition of claim 2, which is an agent for the treatment of inflammation.

8. A method for inhibiting a BLT2 receptor, which comprises contacting the BLT2 receptor with the compound according to claim 1.

* * * * *